US011739381B2

(12) United States Patent
Chew et al.

(10) Patent No.: US 11,739,381 B2
(45) Date of Patent: Aug. 29, 2023

(54) MULTIPLEX CAPTURE OF GENE AND PROTEIN EXPRESSION FROM A BIOLOGICAL SAMPLE

(71) Applicant: 10x Genomics, Inc., Pleasanton, CA (US)

(72) Inventors: Jennifer Chew, Pleasanton, CA (US); Joseph Francis Shuga, Pleasanton, CA (US); Patrick Roelli, Stockholm (SE); Denise Cheung, Pleasanton, CA (US); Alexander Hermes, Pleasanton, CA (US); Yifeng Yin, Pleasanton, CA (US); Naishitha Anaparthy, Pleasanton, CA (US); Ryo Hatori, Pleasanton, CA (US); Marlon Stoeckius, Stockholm (SE); Rapolas Spalinskas, Pleasanton, CA (US); Anna-Maria Katsori, Stockholm (SE); Cedric Uytingco, Pleasanton, CA (US); Mesruh Turkekul, Stockholm (SE); David Sukovich, Pleasanton, CA (US); Christina Galonska, Stockholm (SE); Aleksandra Jurek, Pleasanton, CA (US); Octavian Marian Bloju, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/867,223

(22) Filed: Jul. 18, 2022

(65) Prior Publication Data
US 2022/0389504 A1    Dec. 8, 2022

Related U.S. Application Data

(63) Continuation of application No. PCT/US2022/020985, filed on Mar. 18, 2022.
(Continued)

(51) Int. Cl.
*C12Q 1/6874* (2018.01)
*C12N 15/10* (2006.01)
*C12Q 1/6837* (2018.01)

(52) U.S. Cl.
CPC ....... *C12Q 1/6874* (2013.01); *C12N 15/1065* (2013.01); *C12Q 1/6837* (2013.01)

(58) Field of Classification Search
CPC .. C12Q 1/6874; C12Q 1/6837; C12Q 1/6841; C12Q 2521/501; C12Q 2525/173;
(Continued)

(56) References Cited

U.S. PATENT DOCUMENTS

| 4,683,195 A | 7/1987 | Mullis |
| 4,683,202 A | 7/1987 | Mullis |

(Continued)

FOREIGN PATENT DOCUMENTS

| CN | 1680604 | 10/2005 |
| EP | 1712623 | 10/2006 |

(Continued)

OTHER PUBLICATIONS

U.S. Appl. No. 63/033,348, filed Jun. 2, 2020, Bent.
(Continued)

*Primary Examiner* — Jeremy C Flinders
(74) *Attorney, Agent, or Firm* — Fish & Richardson P.C.

(57) ABSTRACT

Provided herein are methods, compositions, and kits for preparing biological samples for multiplex spatial gene expression and proteomic analysis, such as determining a location of a nucleic acid analyte and a protein analyte in a biological sample.

23 Claims, 44 Drawing Sheets
Specification includes a Sequence Listing.

RNA

PROTEIN

Related U.S. Application Data

(60) Provisional application No. 63/311,703, filed on Feb. 18, 2022, provisional application No. 63/270,230, filed on Oct. 21, 2021, provisional application No. 63/252,335, filed on Oct. 5, 2021, provisional application No. 63/245,697, filed on Sep. 17, 2021, provisional application No. 63/214,058, filed on Jun. 23, 2021, provisional application No. 63/162,870, filed on Mar. 18, 2021.

(58) Field of Classification Search
CPC ........ C12Q 2525/179; C12Q 2531/107; C12Q 2537/159; C12Q 2563/179; C12Q 2565/514; C12Q 2565/601; C12N 15/1065
See application file for complete search history.

(56) References Cited

U.S. PATENT DOCUMENTS

| | | |
|---|---|---|
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,258,568 B1 | 7/2001 | Nyren |
| 6,266,459 B1 | 7/2001 | Walt |
| 6,274,320 B1 | 8/2001 | Rothberg |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,579,695 B1 | 6/2003 | Lambalot |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,897,023 B2 | 5/2005 | Fu |
| 6,942,968 B1 | 9/2005 | Dickinson et al. |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,297,518 B2 | 11/2007 | Quake |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,582,420 B2 | 9/2009 | Oliphant et al. |
| 7,601,498 B2 | 10/2009 | Mao |
| 7,635,566 B2 | 12/2009 | Brenner |
| 7,674,752 B2 | 3/2010 | He |
| 7,700,286 B2 | 4/2010 | Stroun et al. |
| 7,709,198 B2 | 5/2010 | Luo et al. |
| 7,776,567 B2 | 8/2010 | Mao |
| 7,803,943 B2 | 9/2010 | Mao |
| 7,910,304 B2 | 3/2011 | Drmanac |
| 7,955,794 B2 | 6/2011 | Shen et al. |
| 7,960,119 B2 | 6/2011 | Chee |
| 8,003,354 B2 | 8/2011 | Shen et al. |
| 8,148,068 B2 | 4/2012 | Brenner |
| 8,206,917 B2 | 6/2012 | Chee |
| 8,207,093 B2 | 6/2012 | Szostak |
| 8,288,103 B2 | 10/2012 | Oliphant |
| 8,460,865 B2 | 6/2013 | Chee |
| 8,481,257 B2 | 7/2013 | Van Eijk |
| 8,603,743 B2 | 12/2013 | Liu et al. |
| 8,604,182 B2 | 12/2013 | Luo et al. |
| 8,815,512 B2 | 8/2014 | Van Eijk |
| 8,835,358 B2 | 9/2014 | Fodor |
| 8,911,945 B2 | 12/2014 | Van Eijk |
| 8,951,726 B2 | 2/2015 | Luo et al. |
| 9,062,348 B1 | 6/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,506,061 B2 | 11/2016 | Brown et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,727,810 B2 | 8/2017 | Fodor et al. |
| 9,777,324 B2 | 10/2017 | Van Eijk |
| 9,783,841 B2 | 10/2017 | Nolan et al. |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,990 B2 | 8/2018 | Boyden et al. |
| 10,208,982 B2 | 2/2019 | Bannish et al. |
| 10,273,541 B2 | 4/2019 | Hindson et al. |

(56) References Cited

U.S. PATENT DOCUMENTS

| | | |
|---|---|---|
| 10,357,771 B2 | 7/2019 | Bharadwaj |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,590,244 B2 | 3/2020 | Delaney et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 2002/0040275 A1 | 4/2002 | Cravatt |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0148335 A1 | 8/2003 | Shen et al. |
| 2003/0162216 A1 | 8/2003 | Gold |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0096853 A1 | 5/2004 | Mayer |
| 2004/0106110 A1 | 6/2004 | Balasubramanian |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2006/0211001 A1 | 9/2006 | Yu et al. |
| 2006/0216775 A1 | 9/2006 | Burkart et al. |
| 2006/0263789 A1 | 11/2006 | Kincaid |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0009420 A1 | 1/2008 | Schroth et al. |
| 2008/0108804 A1 | 5/2008 | Hayashizaki et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0233802 A1 | 9/2009 | Bignell et al. |
| 2009/0253581 A1 | 10/2009 | van Eijk et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0145037 A1 | 6/2010 | Brive et al. |
| 2011/0028685 A1 | 2/2011 | Purkayastha et al. |
| 2011/0059436 A1 | 3/2011 | Hardin et al. |
| 2011/0245111 A1 | 10/2011 | Chee |
| 2012/0135871 A1 | 5/2012 | van Eijk et al. |
| 2012/0202698 A1 | 8/2012 | van Eijk et al. |
| 2013/0171621 A1 | 7/2013 | Luo et al. |
| 2014/0066318 A1 | 3/2014 | Frisen et al. |
| 2014/0270435 A1* | 9/2014 | Dunn ................... G16B 45/00 382/129 |
| 2014/0274731 A1 | 9/2014 | Raymond et al. |
| 2014/0323330 A1 | 10/2014 | Glezer et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0108458 A1 | 4/2016 | Frei et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2017/0016053 A1 | 1/2017 | Beechem et al. |
| 2017/0029875 A1 | 2/2017 | Zhang et al. |
| 2017/0067096 A1 | 3/2017 | Wassie et al. |
| 2017/0089811 A1 | 3/2017 | Tillberg et al. |
| 2017/0220733 A1 | 8/2017 | Zhuang et al. |
| 2017/0241911 A1 | 8/2017 | Rockel et al. |
| 2017/0275669 A1 | 9/2017 | Weissleder et al. |
| 2018/0051322 A1 | 2/2018 | Church et al. |
| 2018/0057873 A1 | 3/2018 | Zhou et al. |
| 2018/0112261 A1 | 4/2018 | Van Driel et al. |
| 2018/0201980 A1 | 7/2018 | Chee et al. |
| 2018/0216161 A1 | 8/2018 | Chen et al. |

(56) References Cited

U.S. PATENT DOCUMENTS

| | | |
|---|---|---|
| 2018/0216162 A1 | 8/2018 | Belhocine et al. |
| 2018/0245142 A1 | 8/2018 | So et al. |
| 2018/0291439 A1 | 10/2018 | van Eijk et al. |
| 2018/0305681 A1 | 10/2018 | Jovanovich et al. |
| 2019/0032128 A1 | 1/2019 | Chen et al. |
| 2019/0055594 A1 | 2/2019 | Samusik et al. |
| 2019/0064173 A1 | 2/2019 | Bharadwaj et al. |
| 2019/0085383 A1 | 3/2019 | Church et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0233878 A1 | 8/2019 | Delaney et al. |
| 2019/0249226 A1* | 8/2019 | Bent .................. C40B 50/18 |
| 2019/0249248 A1 | 8/2019 | Beechem et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0352708 A1 | 11/2019 | Gaige et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0224244 A1 | 7/2020 | Nilsson et al. |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1* | 4/2021 | Macosko ............ C12Q 1/6841 |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0003482 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1* | 7/2022 | Ach .................. C12Q 1/6806 |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |

(56) References Cited

U.S. PATENT DOCUMENTS

| | | |
|---|---|---|
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0135010 A1 | 5/2023 | Tentori et al. |

FOREIGN PATENT DOCUMENTS

| | | |
|---|---|---|
| EP | 1923471 | 5/2008 |
| EP | 2002017 | 12/2008 |
| EP | 2881465 | 6/2015 |
| EP | 3013984 | 5/2016 |
| EP | 3511423 | 7/2019 |
| EP | 3541956 | 9/2019 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2000/063437 | 10/2000 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2005/007814 | 1/2005 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2009/152928 | 12/2009 |
| WO | WO 2010/126614 | 11/2010 |
| WO | WO 2011/068088 | 6/2011 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/210223 | 12/2014 |
| WO | WO 2014/210225 | 12/2014 |
| WO | WO 2015/031691 | 3/2015 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/019456 | 2/2017 |
| WO | WO 2017/027367 | 2/2017 |
| WO | WO 2017/075293 | 5/2017 |
| WO | WO 2017/096158 | 7/2017 |
| WO | WO 2018/064640 | 4/2018 |
| WO | WO 2018/091676 | 5/2018 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/066720 | 4/2020 |
| WO | WO 2020/076979 | 4/2020 |
| WO | WO 2020/099640 | 5/2020 |
| WO | WO 2020/112604 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |

OTHER PUBLICATIONS

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

(56) References Cited

OTHER PUBLICATIONS

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.
Eng et al., "Transcriptome-scale super-resolved imaging in tissues by RNA seqFISH+," Nature, Apr. 2019, 568(7751):235-239, 37 pages.
Goh et al., "Highly Specific Multiplexed RNA Imaging in Tissues With Split-FISH," Nat Methods, Jun. 15, 2020, 17(7):689-693, 21 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Takei et al., "Integrated Spatial Genomics Reveals Global Architecture of Single Nuclei," Nature, Jan. 27, 2021, 590(7845):344-350, 53 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
U.S. Appl. No. 16/353,937, Frisen et al., filed Mar. 14, 2019.
U.S. Appl. No. 16/876,709, Schnall-Levin et al., filed May 18, 2020.
U.S. Appl. No. 17/707,189, Chell et al., filed Mar. 29, 2022.
U.S. Appl. No. 61/902,105, Kozlov et al., filed Nov. 8, 2013.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent, possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8fl500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8fl500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hvbridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Armani et al, "2D-PCR: a method of mapping DNA in tissue sections," Lab Chip, 2009, 9(24):3526-34.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bergenstråhle et al., "Seamless integration of image and molecular analysis for spatial transcriptomics workflows," BMC Genomics, Jul. 2020, 21(1):482, 7 pages.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulator analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.

(56) References Cited

OTHER PUBLICATIONS

Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Constantine et al., "Use of genechip high-density oligonucleotide arrays for gene expression monitoring," Life Science News, Amersham Life Science, 1998, pp. 11-14.
Credle et al., "Multiplexed analvsis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Czarnik "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Duncan et al., "Affinity chromatography of a sequence-specific DNA binding protein using Teflon-linked oligonucleotides," Anal. Biochem., 1988, 169(1):104-108.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fodor et al., "Light-directed, spatially addressable parallel chemical synthesis," Science, 1995, 251(4995):767-773.
Forster et al., "A human gut bacterial genome and culture collection for improved metagenornic analyses," Nature Biotechnology, 2019, 37(2):186-192.
Fredriksson et al., "Protein detection using proximity-dependent DNA ligation assays," Nature Biotech., 20: 473-77, 2002.
Frese et al., "Formylglycine aldehyde Tag-protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy," BMC Biology, 15:50, 9 pages, 2017.
Gene@arrays[online], BeadArray Technology, available on or before Feb. 14, 2015, via Internet Archive: Wavback Machine URL <https://web.archive.org/web/20150214084616/http://genearrays.com/services/microarrays/illumina/beadarray-technology/>, [retrieved on Jan. 30, 2020], 3 pages.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hua et al., "Multi-level transcriptome sequencing identifies COLIA1 as a candidate marker in human heart failure progression," BMC Med., Jan. 2020, 18(1):2, 16 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kristensen et al., "High-Throughput Methods for Detection of Genetic Variation," BioTechniques, Feb. 2001, 30(2):318-332.

(56) References Cited

OTHER PUBLICATIONS

Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Lee et al., "Fluorescent in situ sequencing (FISSEQ) of RNA for gene expression profiling in intact cells and tissues," Nature Protocols, 2015, 10(3):442-458.
Leriche et al., "Cleavable linkers in chemical biology," Bioorganic & Medicinal Chemistry, 2012, 20:571-582.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lundberg et al., "Multiplexed homogeneous proximity ligation assays for high-throughput protein biomarker research in serological material," Mol Cell Proteomics, 2011, 10(4):M110.004978, 11 pages.
MacBeath et al., "Printing proteins as microarrays for high-throughput function determination," Science, Sep. 2000, 289(5485):1760-1763.
Maniatis et al., "Spatiotemporal Dynamics of Molecular Pathology in Amyotrophic Lateral Sclerosis", 54 pages, 2018.
Marx, "Method of the Year: spatially resolved transcriptomics," Nature Methods, 2021, 18(1):9-14.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-593.
Mizusawa et al., "A bacteriophage lambda vector for cloning with BamHI and Sau3A," Gene, 1982, 20(3):317-322.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
PCT International Search Report and Written Opinion in International Appln. No. PCT/US2022/020985, dated May 25, 2022, 15 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Polsky-Cynkin et al., "Use of DNA immobilized on plastic and agarose supports to detect DNA by sandwich hybridization," Clin. Chem., 1985, 31(9):1438-1443.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Salmén et al., "Barcoded solid-phase RNA capture for Spatial Transoriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Shalon et al., "A DNA microarray system for analyzing complex DNA samples using two-color fluorescent probe hybridization," Genome Res., Jul. 1996, 6(7):639-45.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Strell et al., "Placing RNA in context and space—methods for spatially resolved transcriptomics," The FEBS Journal, 2019, 286(8):1468-1481.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vasiliskov et al., "Fabrication of microarray of gel-immobilized compounds on a chip by copolymerization," Biotechniques, Sep. 1999, 27(3):592-606.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.

(56) References Cited

OTHER PUBLICATIONS

Walker et al., "Strand displacement amplification—an isothermal, in vitro DNA amplification technique," Nucleic Acids Research, 1992, 20(7):1691-1696.

Wang et al., "Imaging-based pooled CRISPR screening reveals regulators of lncRNA localization," Proc Natl Acad Sci USA, May 2019, 116(22):10842-10851.

Wang et al., "High-fidelity mRNA amplification for gene profiling," Nature Biotechnology, Apr. 2000, 18(4):457-459.

Wong et al., "Direct Site-Selective Covalent Protein Immobilization Catalyzed by a Phosphopantetheinyl Transferase," J. Am. Chem Soc., 2008, 130(37):12456-64.

Worthington et al., "Cloning of random oligonucleotides to create single-insert plasmid libraries," Anal Biochem, 2001, 294(2):169-175.

Yershov et al., "DNA analysis and diagnostics on oligonucleotide microchips," Proc. Natl. Acad. Sci. USA, May 1996, 93(10):4913-4918.

Yin et al., "Genetically encoded short peptide tag for versatile protein labeling by Sfp phosphopantetheinyl transferase," PNAS, 2005, 102(44):15815-20.

Zhou et al., "Genetically encoded short peptide tags for orthogonal protein labeling by Sfp and AcpS phosphopantetheinyl transferases," ACS Chemical Biol., 2007, 2(5):337-346.

Zhu et al., "Reverse transcriptase template switching: a SMART approach for full-length cDNA library construction," Biotechniques, Apr. 2001, 30(4):892-897.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Stoeckius et al., "Simultaneous epitope and transcriptome measurement in single cells," Nature Methods, Jul. 31, 2017, 14(9):865-868.

* cited by examiner

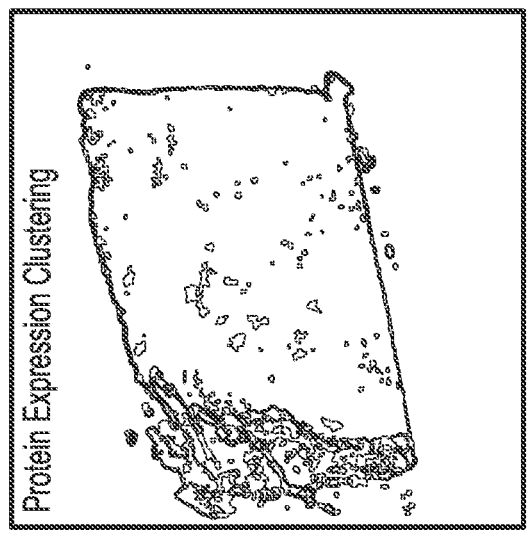
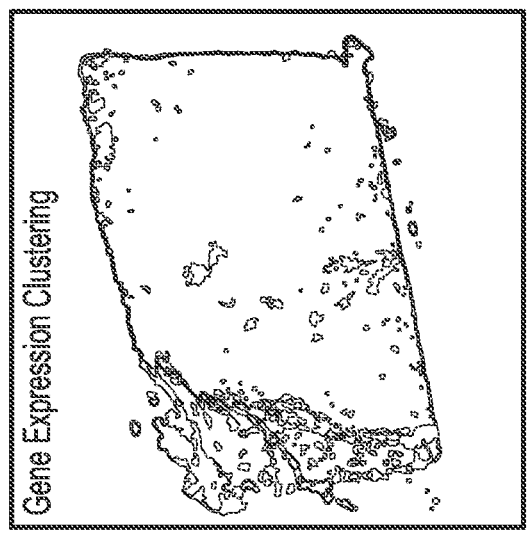
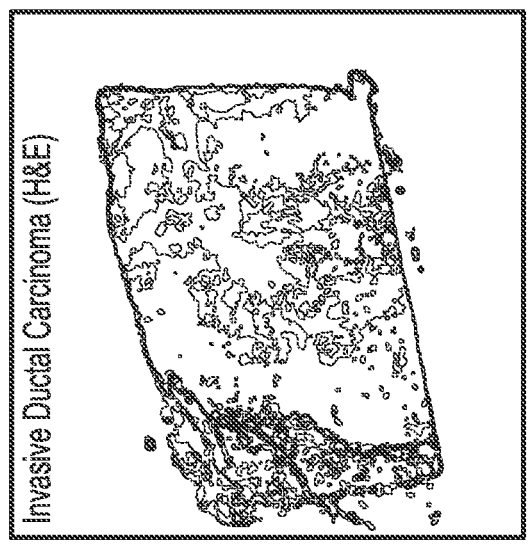
FIG. 11A
FIG. 11B
FIG. 11C

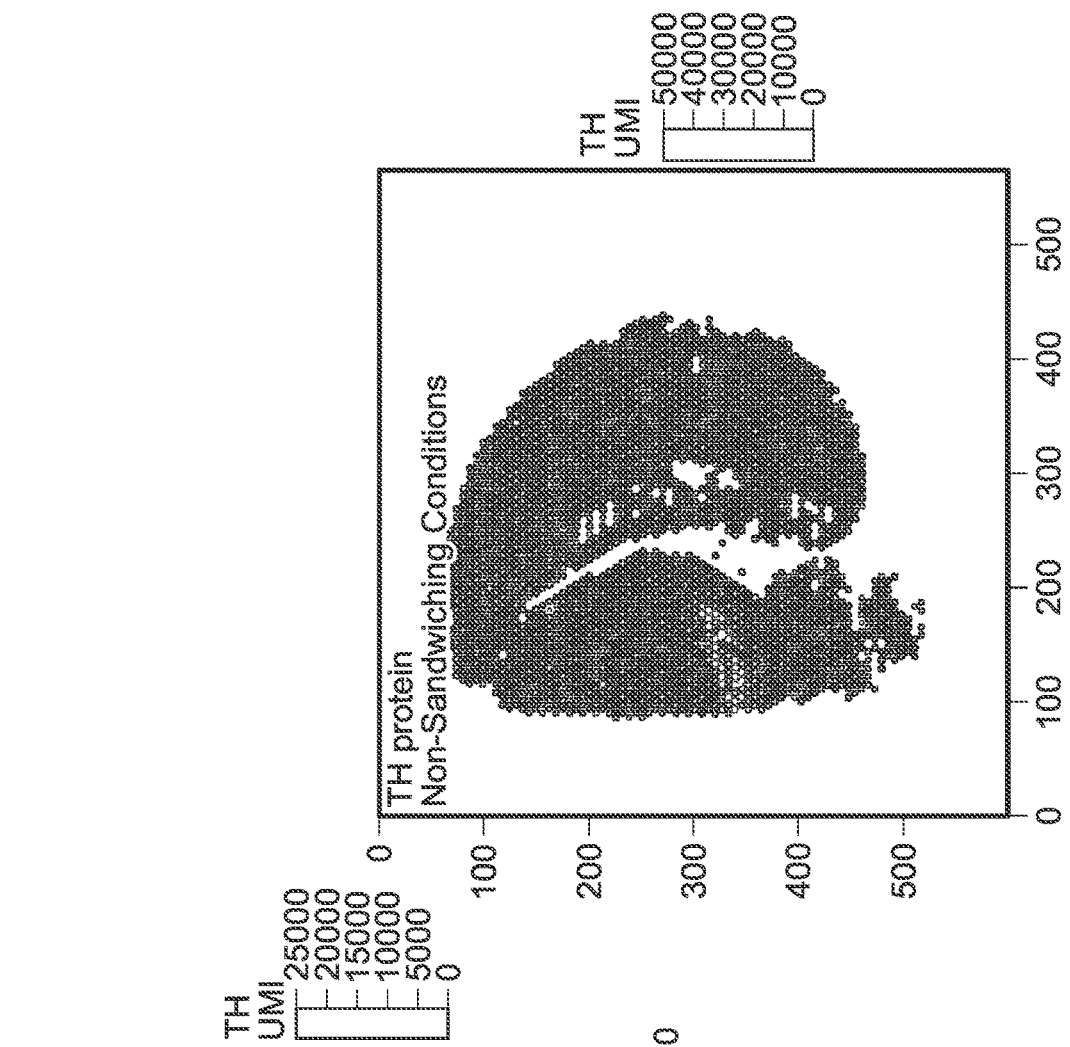
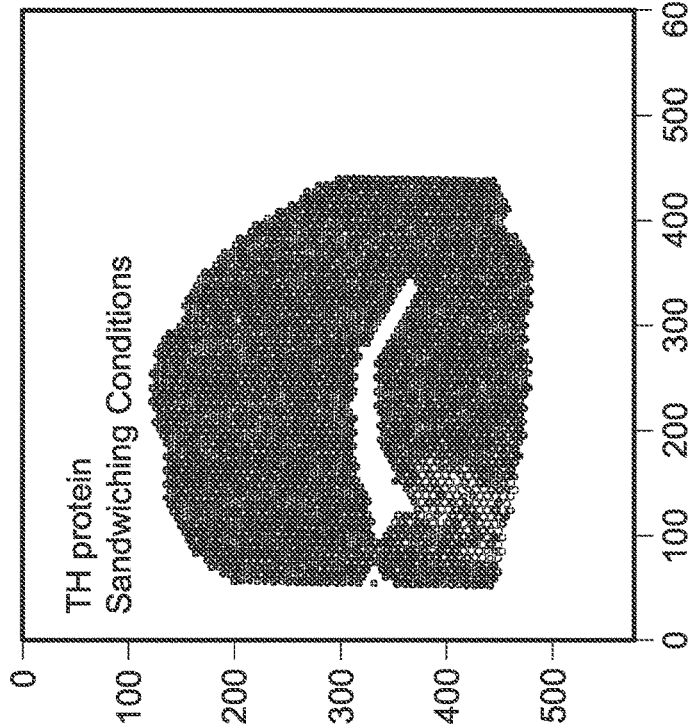
FIG. 15C
FIG. 15D

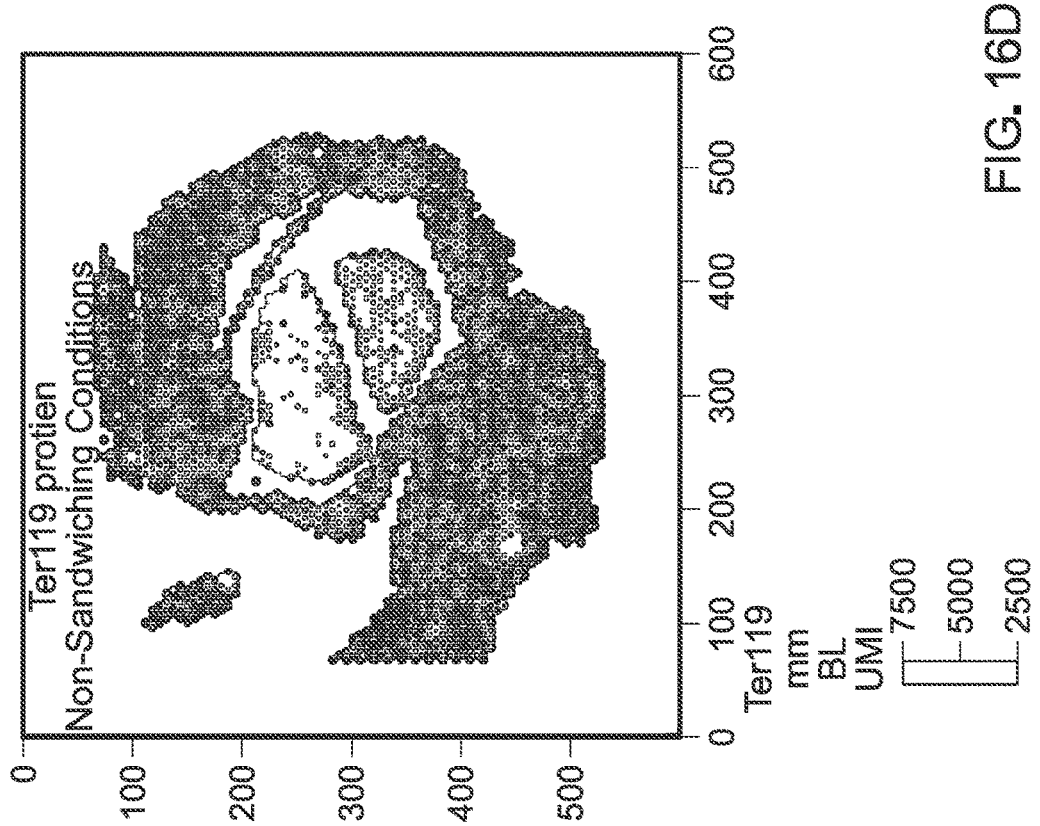
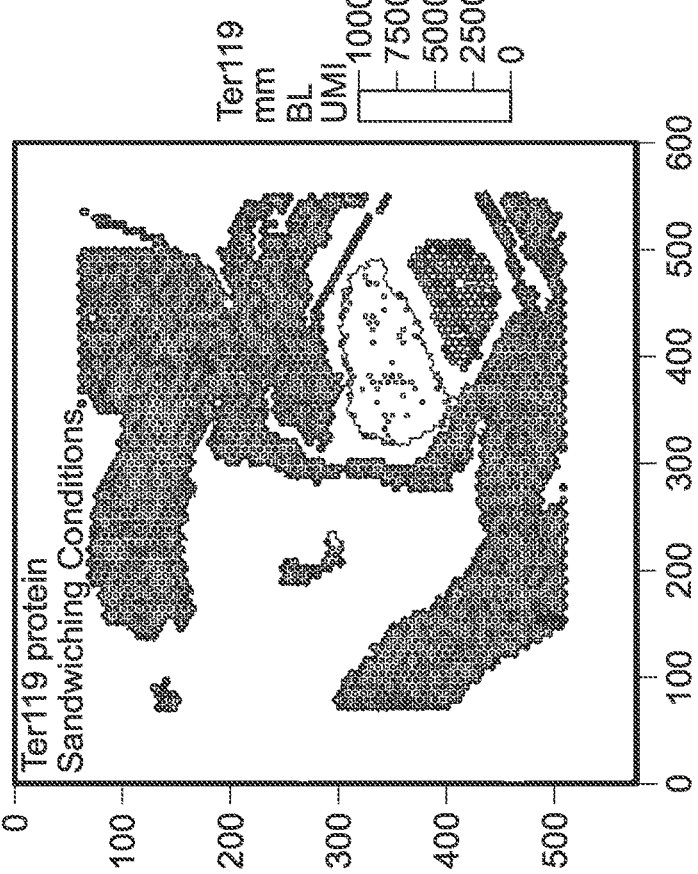
FIG. 16D
FIG. 16C

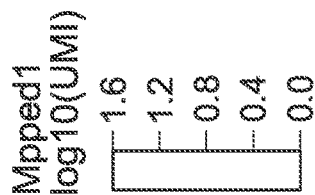
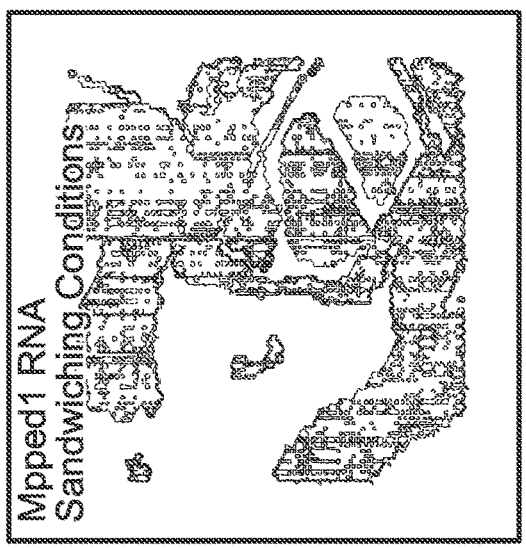
FIG. 18A
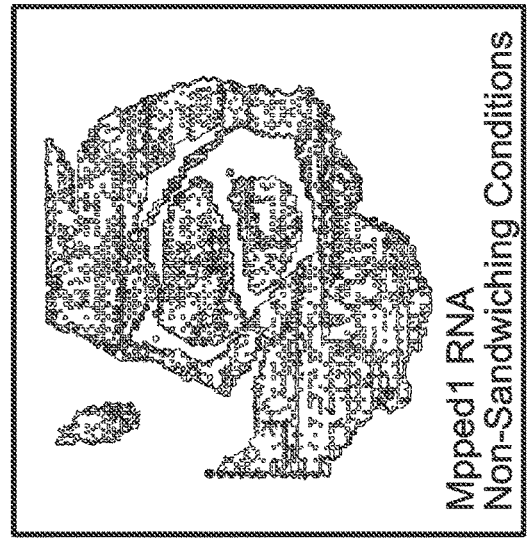
FIG. 18B
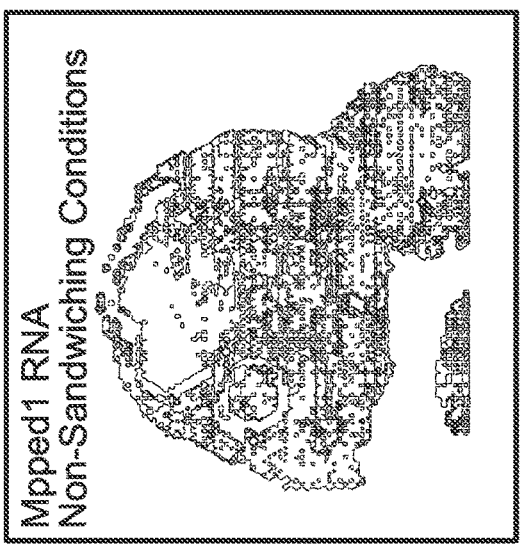
FIG. 18C
FIG. 18D

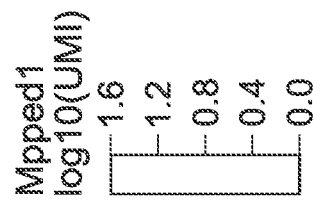
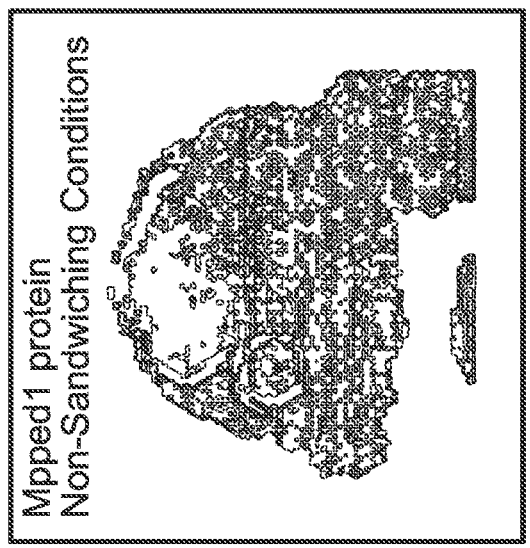
FIG. 18F
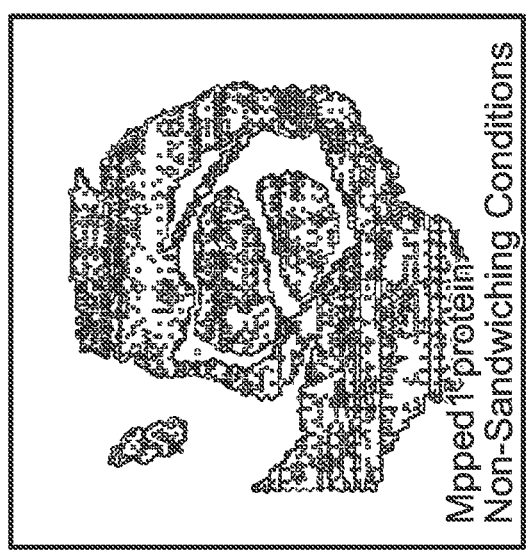
FIG. 18G
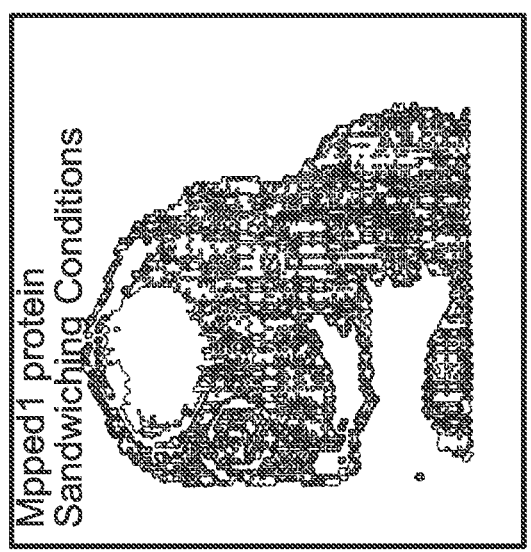
FIG. 18E

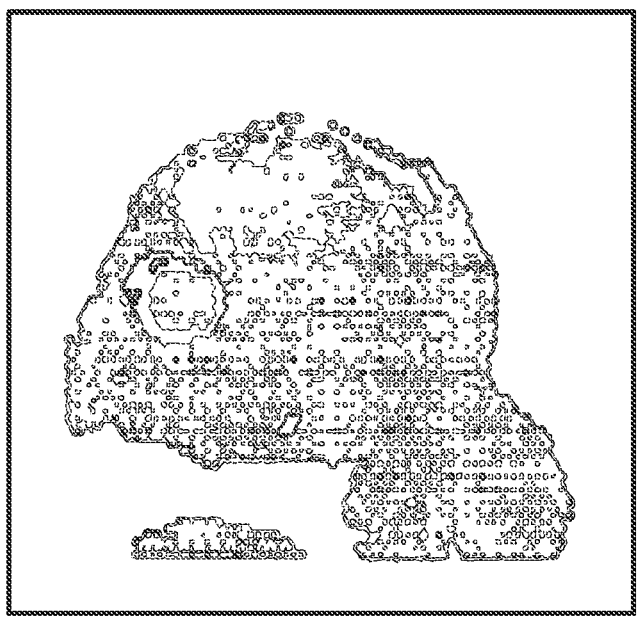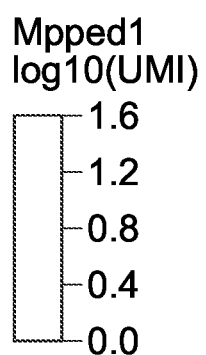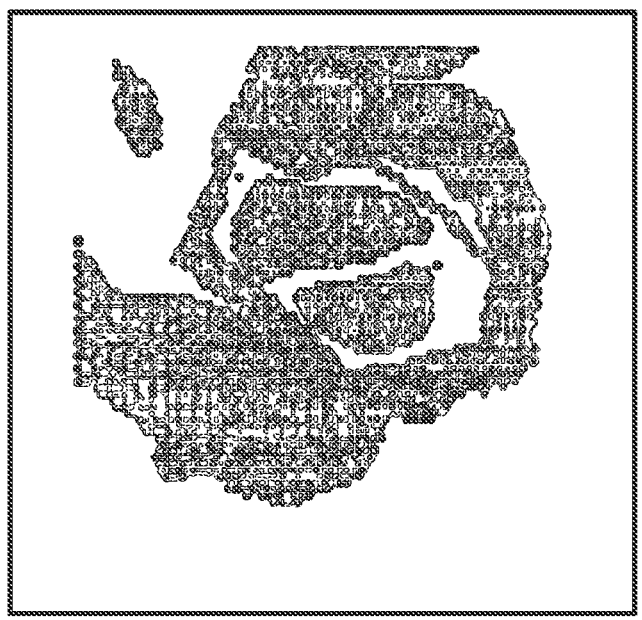
FIG. 18H
FIG. 18I

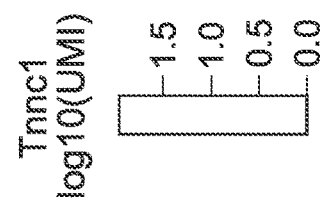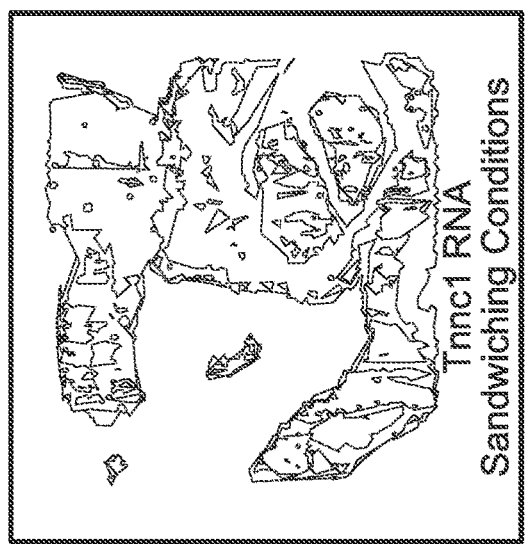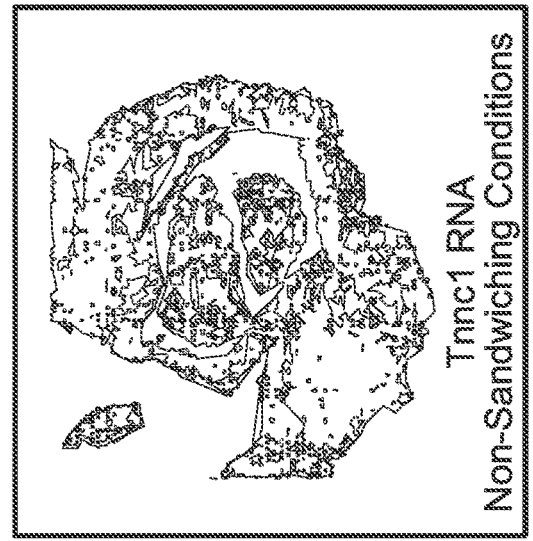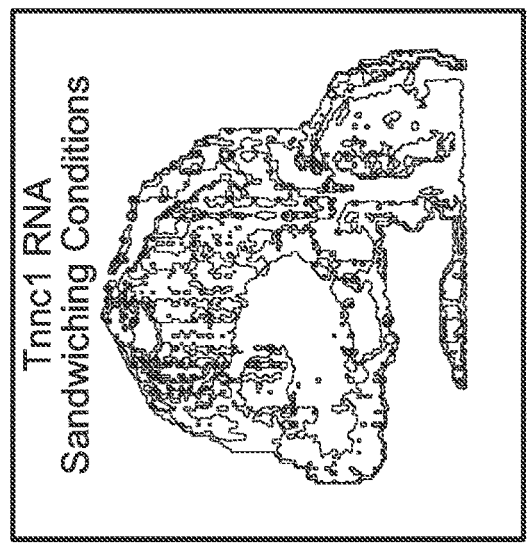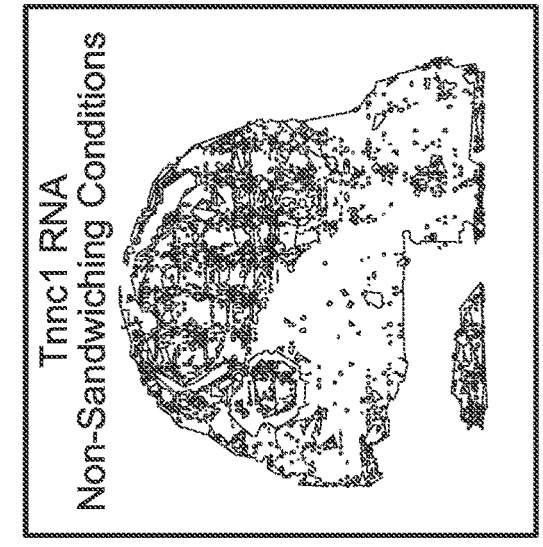
FIG. 19A  FIG. 19B  FIG. 19C  FIG. 19D

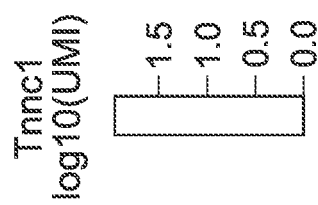
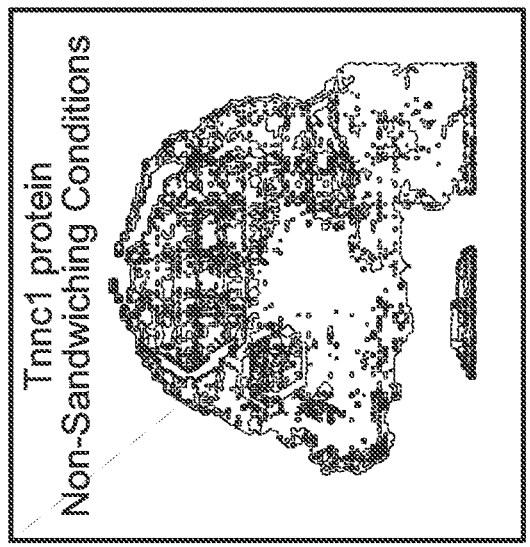
FIG. 19F
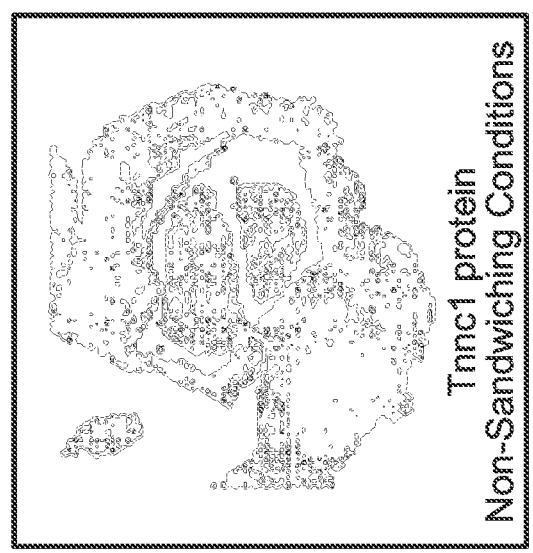
FIG. 19G
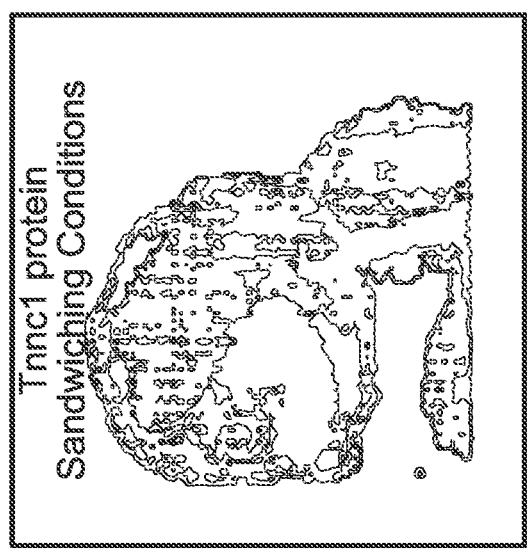
FIG. 19E

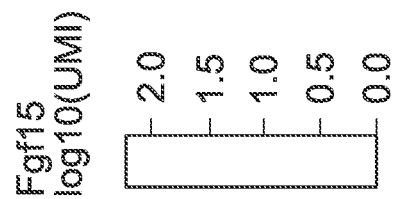
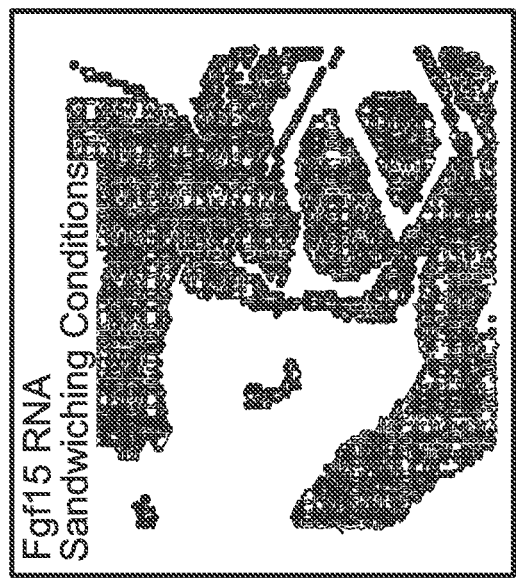
FIG. 20A
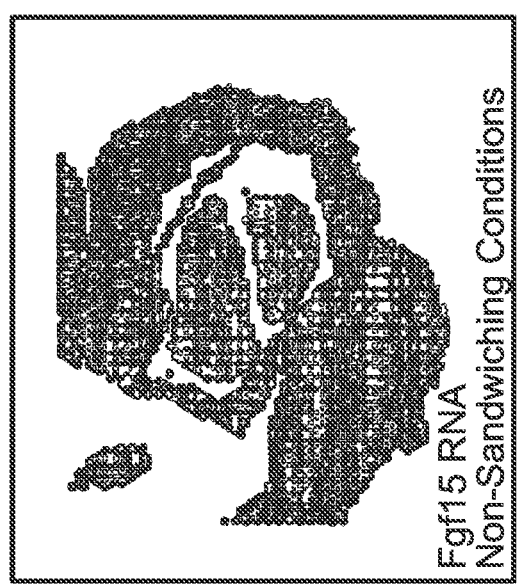
FIG. 20B
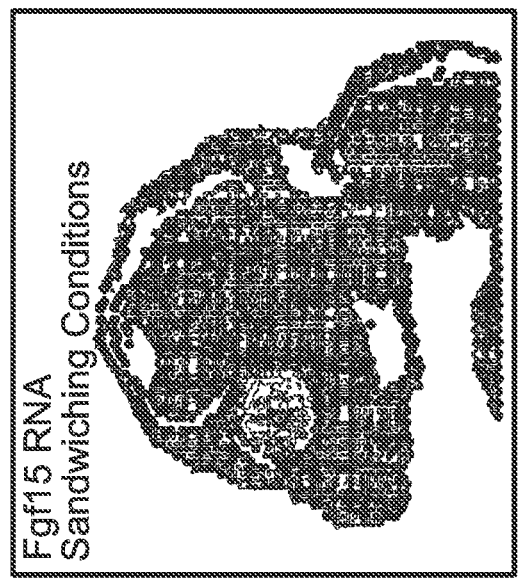
FIG. 20C
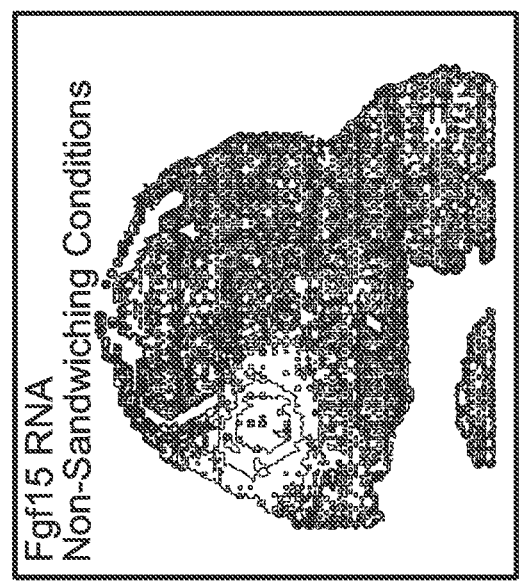
FIG. 20D

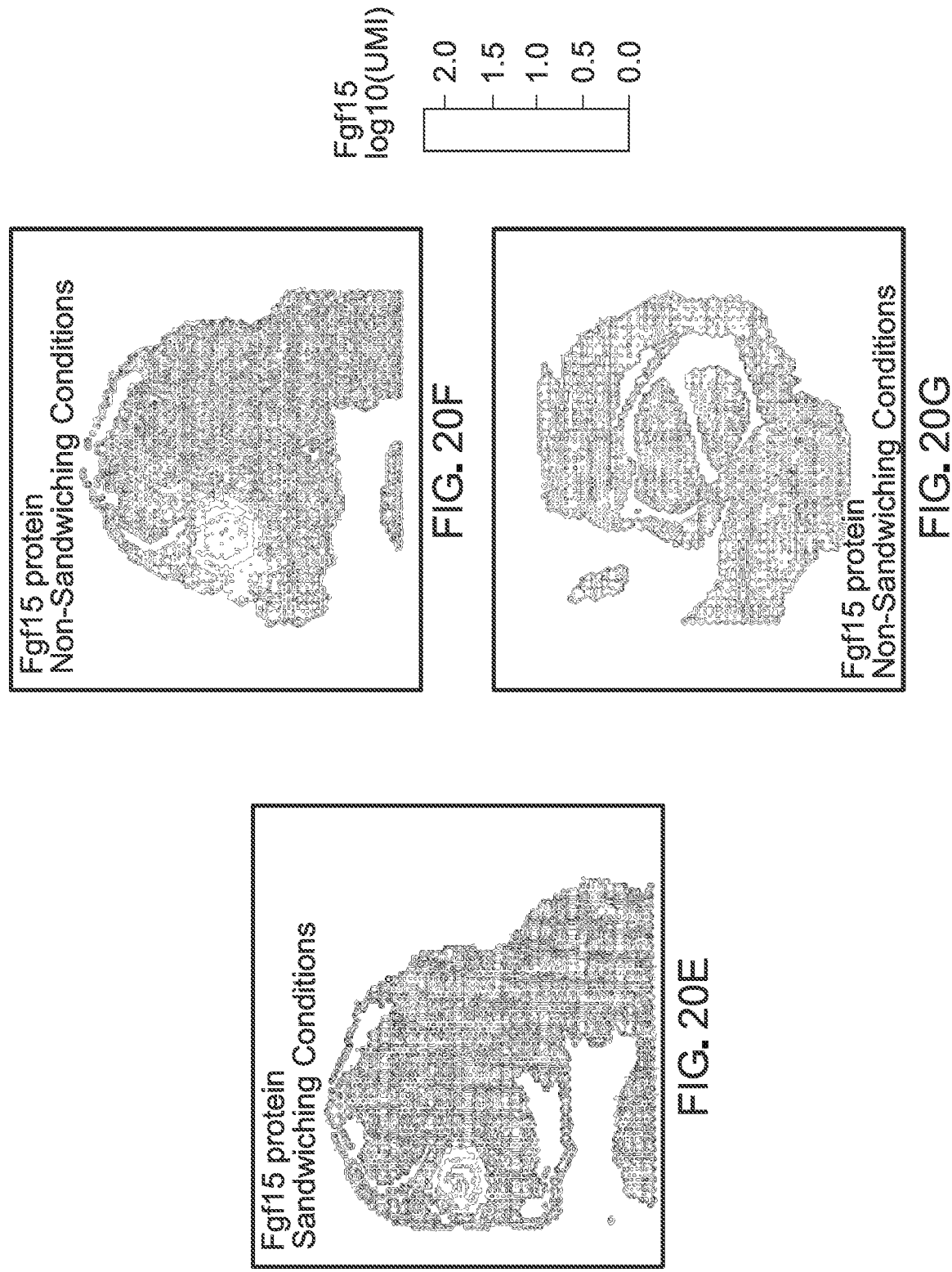

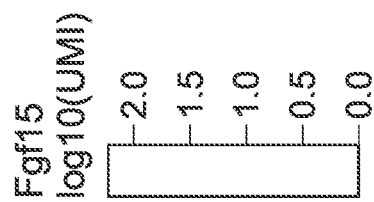
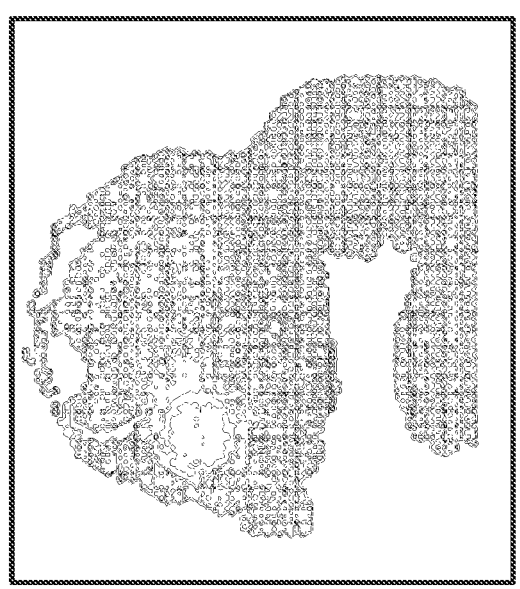
FIG. 20H
Fgf15 RNA
Non-Sandwiching Conditions
(Detection of RNA only)
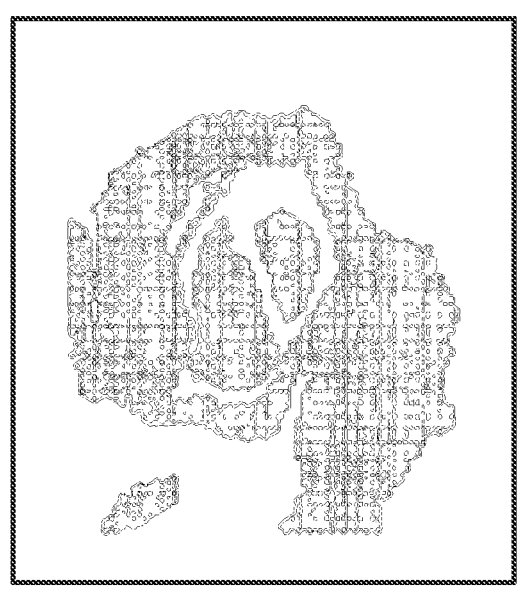
FIG. 20I
Fgf15 RNA
Non-Sandwiching Conditions
(Detection of RNA only)

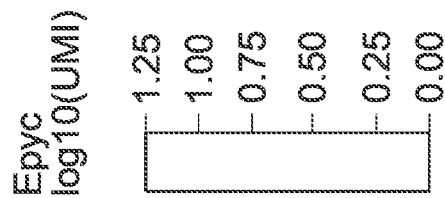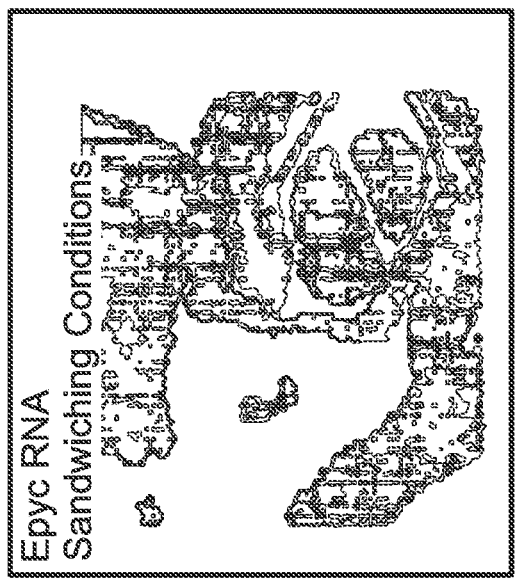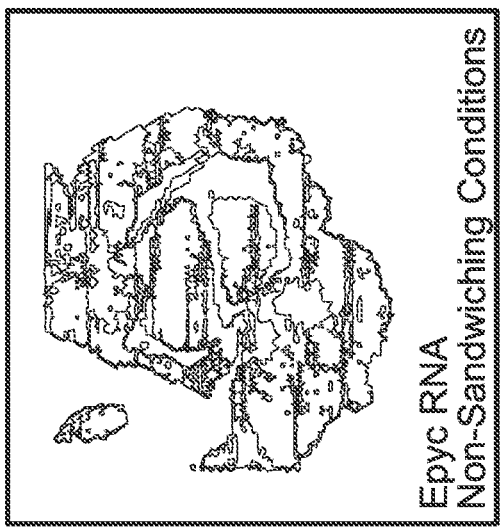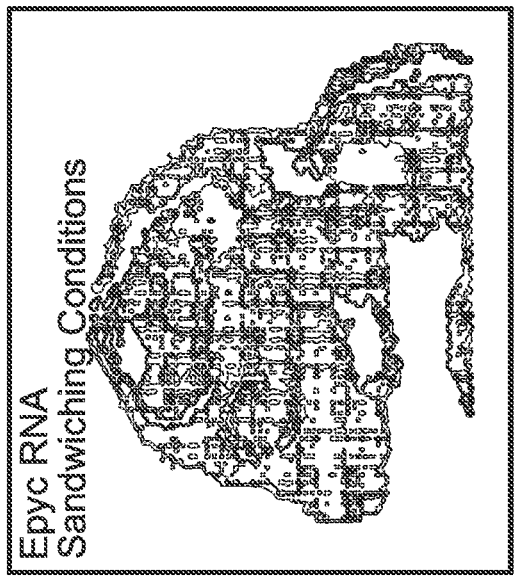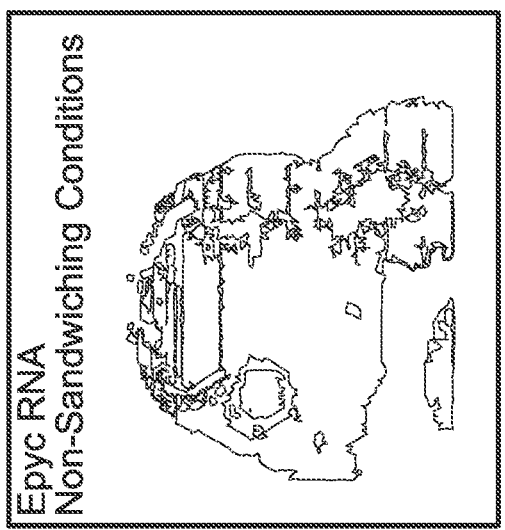
FIG. 21A  FIG. 21B  FIG. 21C  FIG. 21D

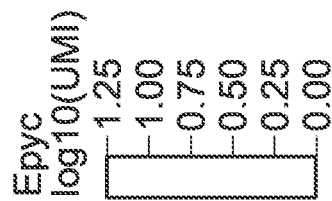
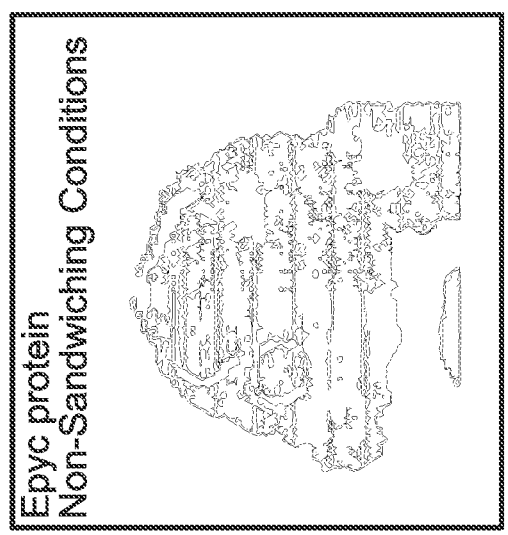
FIG. 21F
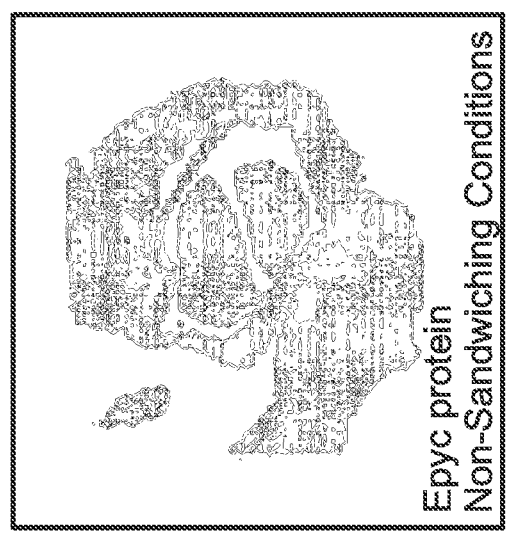
FIG. 21G
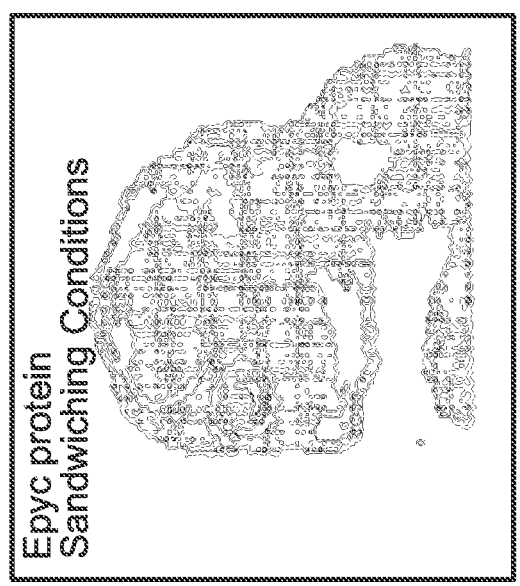
FIG. 21E

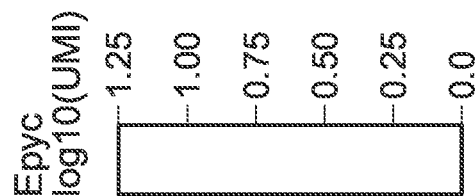
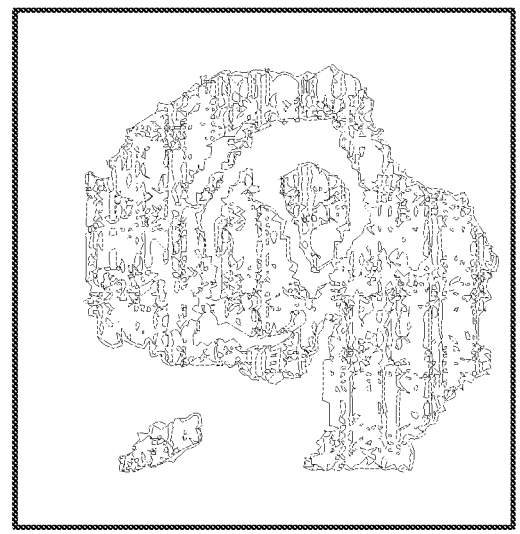
FIG. 21I
Epyc RNA
Non-Sandwiching Conditions
(Detection of RNA only)
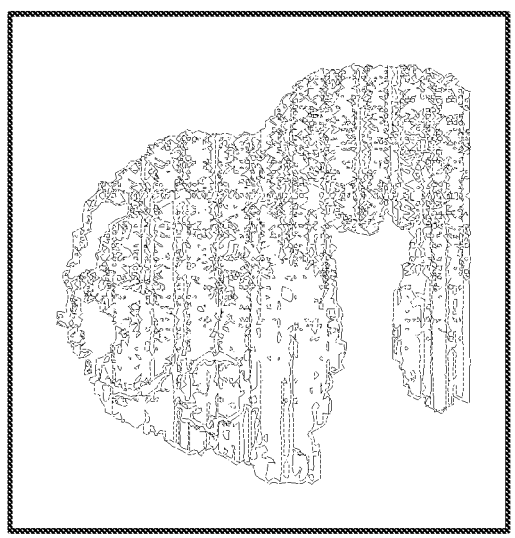
FIG. 21H
Epyc RNA
Non-Sandwiching Conditions
(Detection of RNA only)

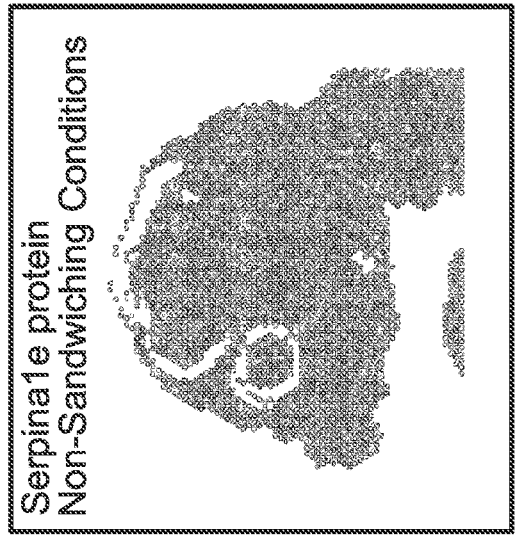
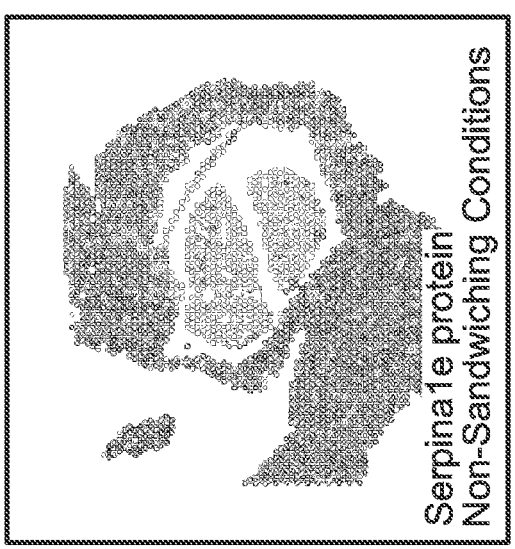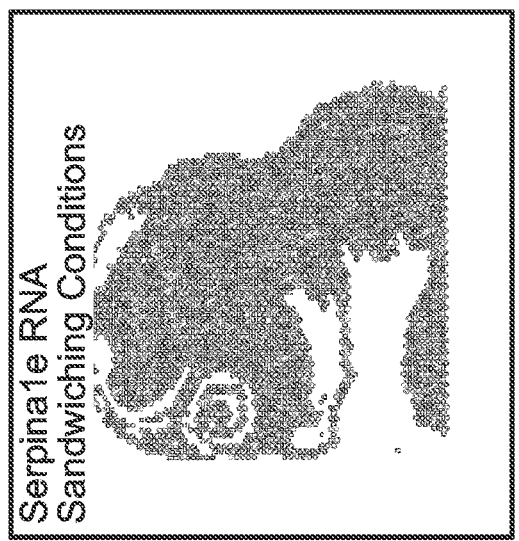

Serpina1e RNA
Non-Sandwiching Conditions
(Detection of RNA only)

Serpina1e RNA
Non-Sandwiching Conditions
(Detection of RNA only)

Pathologist Annotation

☐ Blood Vessel  ☐ DCIS
☐ Immune Cells  ☐ Invasive Carcinoma
☐ Necrosis  ☐ Normal Gland

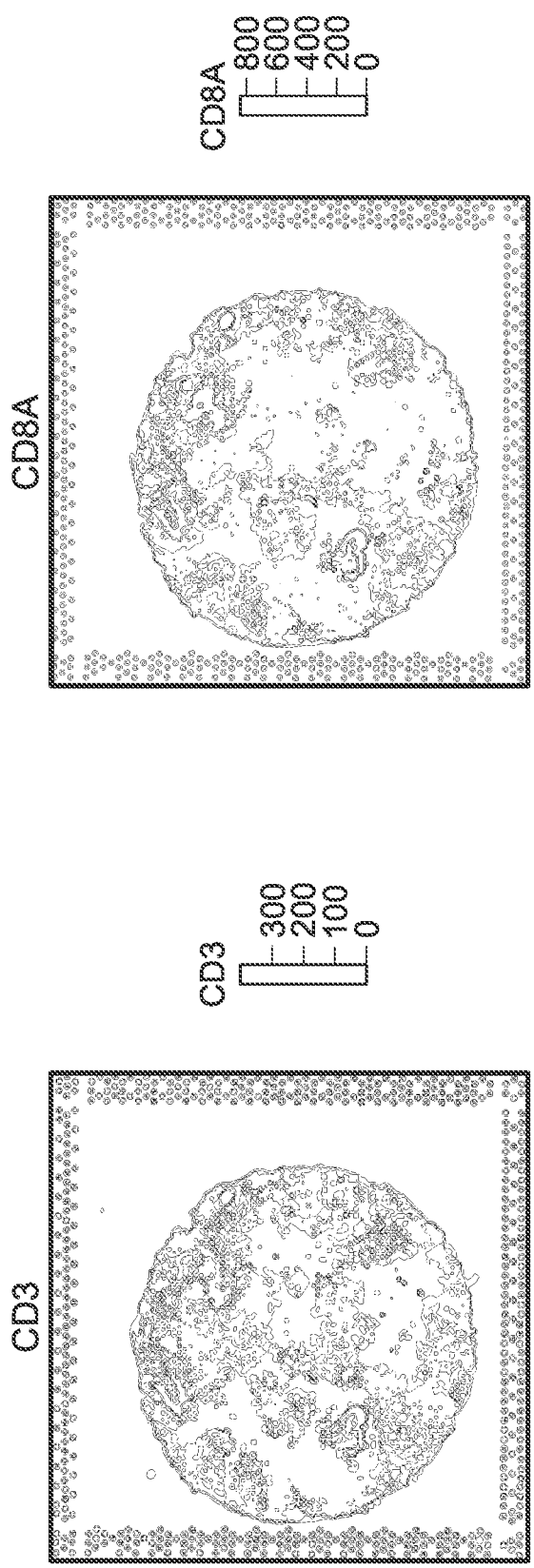
FIG. 23C
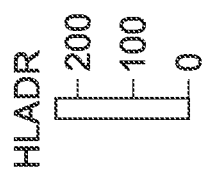
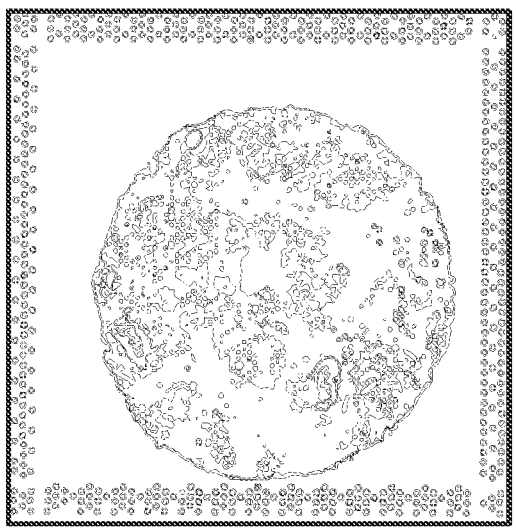
FIG. 23D
FIG. 23E

MULTIPLEX CAPTURE OF GENE AND PROTEIN EXPRESSION FROM A BIOLOGICAL SAMPLE

CROSS-REFERENCE TO RELATED APPLICATIONS

Pursuant to 35 U.S.C. § 119(e), this application is a continuation of International Application PCT/US2022/020985, with an international filing date of Mar. 18, 2022, which claims priority to U.S. Provisional Patent Application No. 63/162,870, filed on Mar. 18, 2021, U.S. Provisional Patent Application No. 63/214,058, filed on Jun. 23, 2021, U.S. Provisional Patent Application No. 63/245,697, filed on Sep. 17, 2021, U.S. Provisional Patent Application No. 63/252,335, filed on Oct. 5, 2021, U.S. Provisional Patent Application No. 63/270,230, filed on Oct. 21, 2021, and U.S. Provisional Patent Application No. 63/311,703, filed on Feb. 18, 2022. The contents of each of these applications is incorporated herein by reference in their entireties.

SEQUENCE LISTING

This application contains a Sequence Listing that has been submitted electronically as an XML file named 47706-0307001.xml. The XML file, created on Jul. 8, 2022, is 15000 bytes in size. The material in the XML file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provides substantial analyte data for dissociated tissue (i.e., single cells), but fail to provide information regarding the position of the single cell in a parent biological sample (e.g., tissue sample).

Moreover, multiplex detection of different analytes (e.g., nucleic acid, protein, etc.) in the same biological sample, while preserving spatial information remains a challenge in the field. Current methods include transcriptome wide spatial detection or various protein detection methods, however, methods that accomplish both within the spatial context of a biological sample are still needed.

SUMMARY

Multiplex detection of different analytes (e.g., nucleic acid, protein, etc.) in the same biological sample, while preserving spatial information remains a challenge in the field. As described above, current methods include transcriptome wide spatial detection or various protein detection methods, including immunofluorescence, however, methods that detect both spatial gene expression and spatial protein expression within the spatial context of a biological sample simultaneously are still needed.

Provided herein are methods for determining the spatial location of a nucleic acid and a protein from a biological sample including: a) providing a spatial array including a first and second plurality of capture probes where each plurality includes a spatial barcode and a capture domain, b) contacting the spatial array with a biological sample, c) contacting the biological sample with (i) a plurality of analyte capture agents, where an analyte capture agent includes an analyte binding moiety and an oligonucleotide including an analyte binding moiety barcode and an analyte capture sequence, where the analyte capture sequence includes a sequence complementary to a second plurality of capture domains, and (ii) a plurality of templated ligation probes, where one of the templated ligation probes includes a sequence complementary a first plurality of capture domains, d) binding the analyte binding moiety of the analyte capture agent to a target protein, e) hybridizing the templated ligation probes to a target nucleic acid and ligating the probes to produce ligation products, f) hybridizing the ligation products to the first plurality of capture domains and the analyte capture sequences of the bound analyte capture agents to the second plurality of capture domains on the spatial array, and g) determining the sequence or a portion thereof of a captured ligation product, or a complement thereof, and the sequence of the spatial barcode of the capture probe, or a complement thereof, that is associated with the ligation product, and the sequence of the analyte binding moiety barcode, or a complement thereof, of the bound analyte capture agent, thereby determining the spatial location of a nucleic acid and the protein from the biological sample.

In some embodiments, the capture domains of the first plurality of capture probes are defined non-homopolymeric capture sequences or homopolymeric sequences. In some embodiments, the capture domains of the second plurality of capture probes are defined non-homopolymeric sequences or homopolymeric capture sequences. In some embodiments, capture domains of the first plurality of capture probes are different from the capture domains of the second plurality of capture probes. In some embodiments, homopolymeric sequence includes a polyT sequence and the non-homopolymeric sequence includes a fixed sequence or a degenerate sequence. In some embodiments, the fixed sequence includes at least one sequence selected from SEQ ID NO: 1 through SEQ ID NO: 11.

In some embodiments, the nucleic acid is a RNA or DNA. In some embodiments, the RNA is a mRNA.

In some embodiments, the biological sample is a tissue sample. In some embodiments, tissue sample is a fresh-frozen tissue sample or a fixed tissue sample, where the fixed tissue sample is a formalin-fixed tissue sample, an acetone fixed tissue sample, a paraformaldehyde tissue sample, or a methanol fixed tissue sample. In some embodiments, the biological sample is a tissue section, where the tissue section is a fresh-frozen tissue section or a fixed section, and optionally, where the fixed tissue section is a formalin-fixed paraffin-embedded tissue section, an acetone fixed tissue section, a paraformaldehyde tissue section, or a methanol fixed tissue section. In some embodiments, the tissue sample is derived from a biopsy sample or a whole rodent embryo.

In some embodiments, before step (b) the biological sample is deparaffinized and decrosslinked. In some embodiments, the decrosslinking includes the use of a buffer. In some embodiments, the buffer includes Tris-EDTA buffer at a pH from about 8 to about 10 and a temperature from about 60° C. to about 80° C. In some embodiments, the buffer includes citrate buffer at a pH from about 5 to about 7 and a temperature from about 70° C. to about 100° C.

In some embodiments, the hybridizing the templated ligation products and the analyte capture sequences of the bound analyte capture agents includes permeabilizing the biological sample.

In some embodiments, the analyte capture sequence of the oligonucleotide is blocked prior to binding to the target protein. In some embodiments, the oligonucleotide of the analyte capture agent is blocked by a blocking probe. In some embodiments, the blocking probe is removed prior to hybridizing the analyte capture sequence of the oligonucleotide of the analyte capture sequence to the capture domain of the capture probe.

In some embodiments, the determining in step (g) includes: a) extending the captured ligation products and the captured oligonucleotides of the analyte capture agents, where the extension products include the spatial barcode or a complement thereof, b) releasing the extension products, or complements thereof, from the spatial array, c) producing a library from the released extension products or complements thereof, and d) sequencing the library.

In some embodiments, prior to step (c) the method includes pre-amplifying the extension products, or complements thereof.

In some embodiments, the complement of the oligonucleotide of the analyte capture agent includes an analyte binding moiety barcode specific to the analyte binding moiety of the analyte capture agent.

In some embodiments, the first and second plurality of capture probes include a cleavage domain, one or more functional domains, a unique molecular identifier, and combinations thereof.

In some embodiments, the method includes imaging the biological sample. In some embodiments, the imaging includes one or more of expansion microscopy, bright field microscopy, dark field microscopy, phase contrast microscopy, electron microscopy, fluorescence microscopy, reflection microscopy, interference microscopy and confocal microscopy.

In some embodiments, the method includes staining the biological sample. In some embodiments, the staining includes hematoxylin and eosin. In some embodiments, the staining includes the use of a detectable label selected from the group consisting of a radioisotope, a fluorophore, a chemiluminescent compound, a bioluminescent compound, or a combination thereof.

In some embodiments, the spatial array includes one or more protein dilution series.

Also provided herein are spatial array including: a) a plurality of capture probes including spatial barcodes and a first plurality of capture domains hybridized to a plurality of templated ligation products, and b) a plurality of capture probes including spatial barcodes and a second plurality of capture domains hybridized to a plurality of oligonucleotides from analyte capture agents, where the oligonucleotides include an analyte capture sequence and an analyte binding moiety barcode.

In some embodiments, the capture probes include cleavage domains, unique molecular identifiers, one or more functional sequences, or a combination thereof.

In some embodiments, the first plurality of capture domains are homopolymeric sequences or defined non-homopolymeric sequences. In some embodiments, the second plurality of capture domains are homopolymeric sequences or defined non-homopolymeric sequences. In some embodiments, the first plurality of capture domains are poly(T) sequences. In some embodiments, the spatial array includes one or more protein dilution series.

Also provided herein are kit including: a) a spatial array including a plurality of capture probes, where the capture probes include spatial barcodes and where the plurality of capture probes include a first plurality of first capture domains and a second plurality of second capture domains, b) one or more analyte capture agents, c) one or more nucleic acid templated ligation probe pairs, and d) one or more enzymes and buffers for practicing any of the methods described herein.

Also provided herein are methods for determining the spatial location of a nucleic acid and a protein in a diseased biological sample including: a) providing a spatial array including a first and a second plurality of capture probes where each plurality includes a spatial barcode and a capture domain, b) contacting the diseased biological sample with the spatial array, c) contacting the diseased biological sample with: (i) a plurality of analyte capture agents, where an analyte capture agent includes an analyte binding moiety and an oligonucleotide including an analyte binding moiety barcode and an analyte capture sequence, where the analyte capture sequence includes a sequence complementary to a second plurality of capture domains, and (ii) a plurality of templated ligation probes, where one of the templated ligation probes includes a sequence complementary a first plurality of capture domains, d) binding the analyte binding moiety of the analyte capture agent to a target protein, e) hybridizing the templated ligation probes to a target RNA and ligating the probes to produce templated ligation products, f) hybridizing the templated ligation products to the first plurality of capture domains and the analyte capture sequences of the bound analyte capture agents to the second plurality of capture domains on the spatial array, and g) determining the sequence or a portion thereof of a captured ligation product, or a complement, and the sequence of the spatial barcode of the capture probe, or a complement thereof, that is associated with the ligation product, and the sequence of the analyte binding moiety barcode, or a complement thereof, of the bound analyte capture agent, thereby determining the spatial location of a nucleic acid and the protein in the diseased biological sample.

In some embodiments, the diseased biological sample is a cancerous biological sample. In some embodiments, the cancerous biological sample is an ovarian cancer biological sample, a breast cancer biological sample, a lung cancer biological sample, or a melanoma. In some embodiments, the breast cancer sample is triple positive breast cancer or a ductal cell invasive carcinoma sample.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 4A (RNA) displays clustering with respect to gene expression of the test panel and FIG. 4B (protein) shows the clustering with respect to the protein expression of the test panel.

FIG. 6 also shows an expanded view of a section of the H&E stained FFPE tonsil tissue section (bottom left) and clustering of gene expression and protein expression of CD8a (bottom middle) and CD4 (bottom right) superimposed on the section of the H&E FFPE tonsil tissue section.

FIG. 9A shows an H&E stained FFPE triple positive breast cancer tissue section. FIG. 9B shows representative gene expression clusters and FIG. 9C shows representative protein expression clusters. The insets shown in FIGS. 9B and 9C show representative tSNE plots.

FIGS. 11A-C show exemplary spatial gene and protein expression in FFPE invasive ductal carcinoma tissue sections. FIG. 11B shows representative gene expression clusters and FIG. 11C shows representative protein expression clusters superimposed on the H&E stained (FIG. 11A) invasive ductal carcinoma tissue sections.

FIG. 15C shows an exemplary image of spatially-resolved information of protein expression of tyrosine hydroxylase protein (TH) using analyte capture agents in FFPE mouse brain tissue under sandwich configuration conditions.

FIG. 15D shows an exemplary image of spatially-resolved information of protein expression of TH using analyte capture agents in FFPE mouse brain tissue under non-sandwich configuration control conditions.

FIG. 16C shows an exemplary image of spatially-resolved information of protein expression of Ter119 using an analyte capture agent in FFPE mouse embryo torso tissue under sandwich configuration conditions.

FIG. 16D shows an exemplary image of spatially-resolved information of protein expression of Ter119 using analyte capture agents in FFPE mouse embryo torso tissue under non-sandwich configuration conditions.

FIGS. 18A, 19A, 20A, 21A, and 22A show exemplary images of spatially-resolved information of gene expression of Mpped1 (FIG. 18A), Tnnc1 (FIG. 19A), Fgf15 (FIG. 20A), Epyc (FIG. 21A), and Serpina1e (FIG. 22A) RNA using ligated probes in FFPE mouse embryo head and upper torso tissue under sandwich configuration conditions.

FIGS. 18B, 19B, 20B, 21B, and 22B show exemplary images of spatially-resolved information of gene expression of Mpped1 (FIG. 18B), Tnnc1 (FIG. 19B), Fgf15 (FIG. 20B), Epyc (FIG. 21B), and Serpina1e (FIG. 22B) RNA using ligated probes in FFPE mouse embryo torso tissue under sandwich configuration conditions.

FIGS. 18C, 19C, 20C, 21C, and 22C show exemplary images of spatially-resolved information of gene expression of Mpped1 (FIG. 18C), Tnnc1 (FIG. 19C), Fgf15 (FIG. 20C), Epyc (FIG. 21C), and Serpina1e (FIG. 22C) RNA using ligated probes in FFPE mouse embryo head and upper torso tissue under non-sandwich configuration conditions.

FIGS. 18D, 19D, 20D, 21D, and 22D show exemplary images of spatially-resolved information of gene expression of Mpped1 (FIG. 18D), Tnnc1 (FIG. 19D), Fgf15 (FIG. 20D), Epyc (FIG. 21D), and Serpina1e (FIG. 22D) RNA using ligated probes in FFPE mouse embryo torso tissue under non-sandwich configuration conditions.

FIGS. 18E, 19E, 20E, 21E, and 22E show exemplary images of spatially-resolved information of protein expression of Mpped1 (FIG. 18E), Tnnc1 (FIG. 19E), Fgf15 (FIG. 20E), Epyc (FIG. 21E), and Serpina1e (FIG. 22E) using analyte capture agents in FFPE mouse embryo head and upper torso tissue under sandwich configuration conditions.

FIGS. 18F, 19F, 20F, 21F, and 22F show exemplary images of spatially-resolved information of protein expression of Mpped1 (FIG. 18F), Tnnc1 (FIG. 19F), Fgf15 (FIG. 20F), Epyc (FIG. 21F), and Serpina1e (FIG. 22F) using analyte capture agents in FFPE mouse embryo head and upper torso tissue under non-sandwich configuration conditions.

FIGS. 18G, 19G, 20G, 21G, and 22G show exemplary images of spatially-resolved information of protein expression of Mpped1 (FIG. 18G), Tnnc1 (FIG. 19G), Fgf15 (FIG. 20G), Epyc (FIG. 21G), and Serpina1e (FIG. 22G) using analyte capture agents in FFPE mouse embryo torso tissue under non-sandwich configuration conditions.

FIGS. 18H, 19H, 20H, 21H, and 22H show exemplary images of spatially-resolved information of gene expression of Mpped1 (FIG. 18H), Tnnc1 (FIG. 19H), Fgf15 (FIG. 20H), Epyc (FIG. 21H), and Serpina1e (FIG. 22H) RNA using ligated probes in FFPE mouse embryo head and upper torso tissue under non-sandwich configuration conditions in which only RNA was detected.

FIGS. 18I, 19I, 20I, 21I, and 22I show exemplary images of spatially-resolved information of gene expression of Mpped1 (FIG. 18I), Tnnc1 (FIG. 19I), Fgf15 (FIG. 20I), Epyc (FIG. 21I), and Serpina1e (FIG. 22I) RNA using ligated probes in FFPE mouse embryo torso tissue under non-sandwich configuration conditions in which only RNA was detected.

FIGS. 23A-E show spatial immune cell infiltration in a breast cancer tissue section correlates with pathologist annotations. FIG. 23A shows an H&E stained human breast cancer FFPE tissue section. FIG. 23B shows the pathologist's annotations. FIG. 23C shows spatial protein expression of CD3 (e.g., a marker for T cells); FIG. 23D shows spatial protein expression of CD8A (e.g., a marker for cytotoxic T cells); and FIG. 23E shows spatial protein expression for HLA-DR (e.g., a marker for T cell activation).

FIG. 24A shows a pathologist's annotation for invasive carcinoma and immune cells. FIG. 24B shows spatial protein expression of CD20 (e.g., a marker for B cells); FIG. 24C shows spatial protein expression of CD68 (e.g., a marker for monocytes); and FIG. 24D shows spatial protein expression of CD8A (e.g., a marker for cytotoxic T cells).

FIG. 25A shows spatial protein expression of CD8A (e.g., a marker for cytotoxic T cells). FIG. 25B shows highly infiltrated ("hot", CD3) and not filtrated ("cold", CD8) areas of protein expression in the FFPE tissue section shown in FIG. 25A. FIG. 25C shows spatial protein expression of HLA-G and FIG. 25D shows spatial protein expression of IMPG2.

FIG. 27A shows an H&E stained lung cancer FFPE tissue and FIG. 27D shows a HLA-DR protein spatial UMI plot.

FIG. 28A shows an H&E stained melanoma cancer tissue and FIG. 28D shows a HLA-DR protein spatial UMI plot.

DETAILED DESCRIPTION

Figure 1:
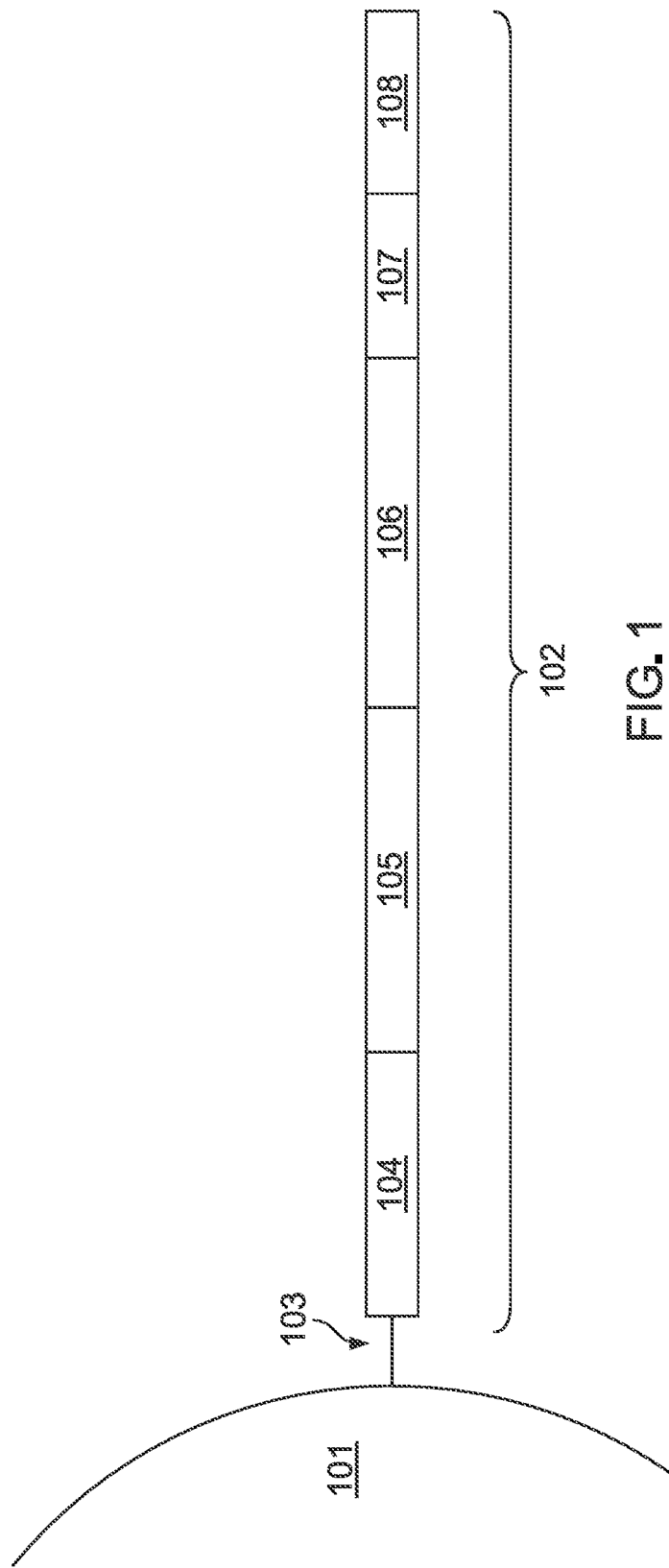
FIG. 1 is a schematic diagram showing an example of a barcoded capture probe, as described herein.

The present disclosure features methods, compositions, and kits for spatial analysis of biological samples. More specifically, the present disclosure features methods, compositions, and kits for both spatial gene expression and spatial protein expression in a biological sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

As used herein, the term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

As used herein, the term "analyte binding moiety barcode" refers to a barcode that is associated with or otherwise identifies the analyte binding moiety. In some cases, an analyte binding moiety barcode (or portion thereof) may be able to be removed (e.g., cleaved) from the analyte capture agent. In some embodiments, by identifying an analyte binding moiety and its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies or aptamers) as well as being readily detected, (e.g., using sequencing or array technologies). Additional description of analyte capture agents can be found in Section (II)(b)(ix) of WO 2020/176788 and/or Section (II)(b)(viii) U.S. Patent Application Publication No. 2020/0277663.

In some embodiments, the capture agent barcode domain of an analyte capture agent includes an analyte capture sequence. As used herein, the term "analyte capture sequence" refers to a region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

Figure 2:
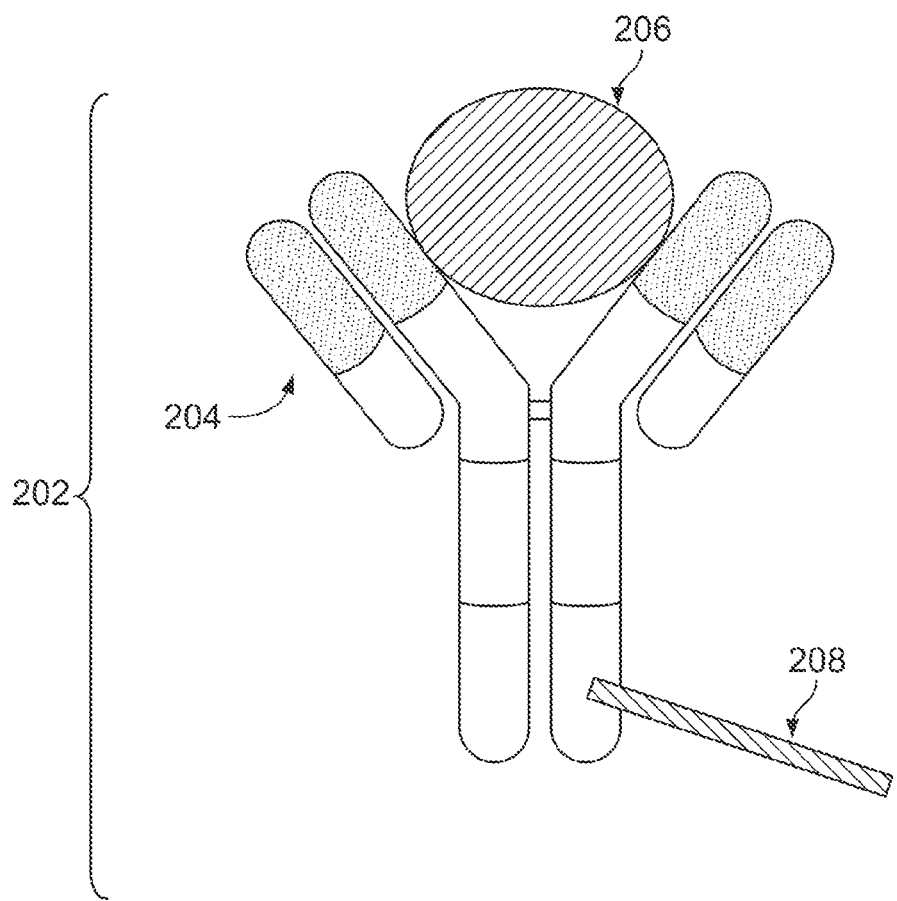
FIG. 2 is a schematic diagram of an exemplary analyte capture agent.

FIG. 2 is a schematic diagram of an exemplary analyte capture agent 202 comprised of an analyte binding moiety 204 and a capture agent barcode domain 208. An analyte binding moiety 204 is a molecule capable of binding to an analyte 206 and interacting with a spatially-barcoded capture probe. The analyte binding moiety can bind to the analyte 206 with high affinity and/or with high specificity. The analyte capture agent can include a capture agent barcode domain 208, a nucleotide sequence (e.g., an oligonucleotide), which can hybridize to at least a portion or an entirety of a capture domain of a capture probe. The analyte binding moiety 204 can include a polypeptide and/or an aptamer (e.g., an oligonucleotide or peptide molecule that binds to a specific target analyte). The analyte binding moiety 204 can include an antibody or antibody fragment (e.g., an antigen-binding fragment).

Figure 3:
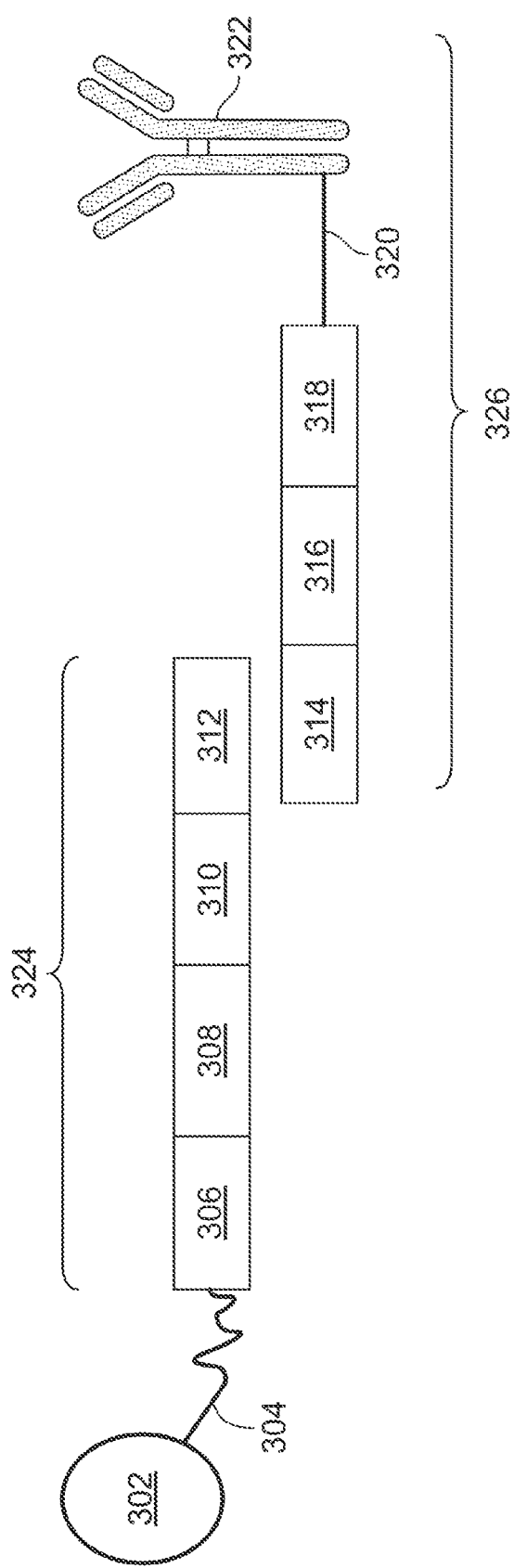
FIG. 3 is a schematic diagram depicting an exemplary interaction between a feature-immobilized capture probe 324 and an analyte capture agent 326.

FIG. 3 is a schematic diagram depicting an exemplary interaction between a feature-immobilized capture probe 324 and an analyte capture agent 326. The feature-immobilized capture probe 324 can include a spatial barcode 308 as well as one or more functional sequences 306 and 310, as described elsewhere herein. The capture probe can also include a capture domain 312 that is capable of binding to an analyte capture agent 326. The analyte capture agent 326 can include a functional sequence 318, capture agent barcode domain 316, and an analyte capture sequence 314 that is capable of binding to the capture domain 312 of the capture probe 324. The analyte capture agent can also include a linker 320 that allows the capture agent barcode domain 316 to couple to the analyte binding moiety 322.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication No. 2021/0140982A1, U.S. Patent Application No. 2021/0198741A1, and/or U.S. Patent Application No. 2021/0199660.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in WO 2021/102003 and/or U.S. patent application Ser. No. 16/951,854, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2021/102039 and/or U.S. patent application Ser. No. 16/951,864, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, WO 2021/102005, and/or U.S. patent application Ser. No. 16/951,843, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Multiplex Gene Expression and Protein Analysis

Understanding both gene and protein expression in biological systems can be helpful for gaining insights into normal, developing, and diseased tissues. While single cell RNA-seq (scRNA-seq) makes it possible to obtain high-resolution gene expression measurements, the technique requires cells to be dissociated, thereby losing anatomical and organizational information. Similarly, numerous protein detection techniques are known and can provide spatial information of proteins in a biological sample, however, methods of simultaneously detecting levels of gene expression (e.g., mRNA) of the protein, or even the entire transcriptome are still needed.

Thus, disclosed herein are "multi-omics" approaches that can provide a powerful complement to traditional methodologies, enabling a greater understanding of cellular heterogeneity and organization within biological samples. The combination of protein detection using analyte capture agents on a spatial array allows for the simultaneous examination of protein and gene expression from the same biological sample (e.g., tissue section). For example, an array comprising capture probes (e.g., any of the capture probes described herein) can be contacted with a biological sample, a plurality of templated ligation probes, and a plurality of analyte capture agents that result in simultaneous gene and protein expression analysis.

In some embodiments, the plurality of templated ligation probes include a pair of probes for a target nucleic acid (e.g., DNA, RNA). The probes are complementary to portions of the target nucleic acid, however, when both probes hybridize to the target nucleic acid a gap is present between the two probes. In some embodiments, the gap is ligated, thereby generating a templated ligation product (e.g., DNA or RNA templated ligation product). In some embodiments, one of the pair of probes includes a flanking sequence complementary to a capture domain of the array. In some embodiments, the sequence complementary to the capture domain of the templated ligation product hybridizes to the capture domain of the capture probe.

In some embodiments, analyte capture agents, as described herein, can also be contacted with the biological sample. In some embodiments, the analyte capture agents are contacted with the biological sample before the biological sample is contacted with an array. In some embodiments, the analyte capture agents are contacted with the biological sample after the biological sample is contacted with the array. In some embodiments, the analyte binding moiety of the analyte capture agent interacts (e.g., binds) to an analyte (e.g., protein) in a biological sample. In some embodiments, the analyte binding moiety is an antibody or antigen-binding fragment.

Analyte capture agents can also include a conjugated oligonucleotide that can comprise one or more domains. For example, the conjugated oligonucleotide can include an analyte binding moiety barcode and an analyte capture sequence. In some embodiments, the analyte binding moiety barcode, or a complement thereof, refers to (e.g., identifies) a barcode that is associated with or otherwise identifies the analyte binding moiety. In some embodiments, the conjugated oligonucleotide can include an analyte capture sequence. In some embodiments, the analyte capture sequence is capable of interacting with (e.g., hybridizing) to a capture domain of a capture probe on a substrate.

In some embodiments, the templated ligation probes are allowed to bind the target nucleic acid before the analyte capture agents are delivered to the biological sample. In some embodiments, the templated ligation probes can be ligated together before, concurrently, or after the analyte capture agents are delivered to the biological sample. In some embodiments, the analyte capture agents are delivered to the biological sample and the analyte binding moiety is allowed to bind the target analyte (e.g., protein) before the templated ligation probes are delivered. In some embodiments, the analyte capture agents are delivered to the biological sample and the analyte capture sequence is blocked (e.g., blocked by any of the methods described herein). In some embodiments, the analyte capture sequence of the analyte capture agents is unblocked (e.g., unblocked by any of the methods described herein) before, concurrently, or after the templated ligation probes (e.g., RNA templated ligation probes) are delivered and/or before, concurrently, or after the templated ligation probes are ligated together.

Thus, provided herein are methods for determining the spatial location of a nucleic acid and a protein from a biological sample including: a) providing a spatial array including a first and second plurality of capture probes where each plurality includes a spatial barcode and a capture domain, b) contacting the spatial array with a biological sample, c) contacting the biological sample with (i) a plurality of analyte capture agents, where an analyte capture agent includes an analyte binding moiety and an oligonucleotide including an analyte binding moiety barcode and an analyte capture sequence, where the analyte capture sequence includes a sequence complementary to a second plurality of capture domains, and (ii) a plurality of templated ligation probes, where one of the templated ligation probes includes a sequence complementary a first plurality of capture domains, d) binding the analyte binding moiety of the analyte capture agent to a target protein, e) hybridizing the templated ligation probes to a target nucleic acid and ligating the probes to produce ligation products, f) hybridizing the ligation products to the first plurality of capture domains and the analyte capture sequences of the bound analyte capture agents to the second plurality of capture domains on the spatial array, and g) determining the sequence or a portion thereof of a captured ligation product, or a complement thereof, and the sequence of the spatial barcode of the capture probe, or a complement thereof, that is associated with the ligation product, and the sequence of the analyte binding moiety barcode, or a complement thereof, of the bound analyte capture agent, thereby determining the spatial location of a nucleic acid and the protein from the biological sample.

Also provided herein are methods for determining the spatial location of a nucleic acid and a protein in a diseased biological sample including: a) providing a spatial array including a first and a second plurality of capture probes where each plurality includes a spatial barcode and a capture domain, b) contacting the diseased biological sample with the spatial array, c) contacting the diseased biological sample with: (i) a plurality of analyte capture agents, where an analyte capture agent includes an analyte binding moiety and an oligonucleotide including an analyte binding moiety barcode and an analyte capture sequence, where the analyte capture sequence includes a sequence complementary to a second plurality of capture domains, and (ii) a plurality of templated ligation probes, where one of the templated ligation probes includes a sequence complementary a first plurality of capture domains, d) binding the analyte binding moiety of the analyte capture agent to a target protein, e) hybridizing the templated ligation probes to a target RNA and ligating the probes to produce templated ligation products, f) hybridizing the templated ligation products to the first plurality of capture domains and the analyte capture sequences of the bound analyte capture agents to the second plurality of capture domains on the spatial array, and g) determining the sequence or a portion thereof of a captured ligation product, or a complement, and the sequence of the spatial barcode of the capture probe, or a complement thereof, that is associated with the ligation product, and the sequence of the analyte binding moiety barcode, or a complement thereof, of the bound analyte capture agent, thereby determining the spatial location of a nucleic acid and the protein in the diseased biological sample.

In some embodiments, the nucleic acid is RNA. In some embodiments, the RNA is mRNA. In some embodiments, the nucleic acid is DNA.

In some embodiments, the diseased biological sample is a cancerous biological sample. In some embodiments, the cancerous biological sample is an ovarian cancer biological sample or a breast cancer biological sample. In some embodiments, the breast cancer sample is triple positive breast cancer. In some embodiments, the breast cancer is invasive ductal cell carcinoma breast cancer. In some embodiments, the invasive ductal cell carcinoma is grade II invasive ductal carcinoma. In some embodiments, the invasive ductal cell carcinoma is grade III invasive ductal carcinoma. In some embodiments, the breast cancer is invasive lobular carcinoma. In some embodiments, the cancerous biological sample is lung cancer. In some embodiments, the cancerous biological sample is melanoma. In some embodiments, the cancerous biological sample is colon cancer. In some embodiments, the cancerous biological sample is glioblastoma. In some embodiments, the cancerous biological sample is prostate cancer.

In some embodiments, the capture probes include unique molecular identifiers, functional sequences, or combinations thereof.

In some embodiments, the first plurality of capture domains are homopolymeric sequences. In some embodiments, the first plurality of capture domains comprise poly (T) sequences. In some embodiments, the first plurality of capture domains are defined non-homopolymeric sequences. In some embodiments, the first plurality of capture domains includes a degenerate sequence. In some embodiments, the first plurality of capture domains includes a fixed sequence. For example, the first plurality of capture domains can comprises one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some embodiments, the second plurality of capture domains are homopolymeric sequences. In some embodiments, the second plurality of capture domains are defined non-homopolymeric sequences. In some embodiments, the second plurality of capture domains comprise poly(T) sequences. In some embodiments, the second plurality of capture domains includes a degenerate sequence. In some embodiments, the second plurality of capture domains includes a fixed sequence. For example, the second plurality of capture domains can comprise one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some embodiments, the first plurality of capture domains and the second plurality of capture domains include the same sequence. In some embodiments, the first plurality of capture domains and the second plurality of capture domains include different sequences.

Generally, the methods of the present disclosure can be used with any biological sample (e.g., any biological sample described herein). In some embodiments, the biological sample is a tissue section. In some embodiments, the biological sample is a tissue sample. In some embodiments, the biological sample is a fresh-frozen biological sample. In some embodiments, the biological sample is a fixed biological sample (e.g., formalin-fixed paraffin embedded (FFPE), paraformaldehyde, acetone, or methanol). In some embodiments, the biological sample is an FFPE sample. In some embodiments, the biological sample is an FFPE tissue section. In some embodiments, the tissue sample is a tumor sample. In some embodiment, the tissue section is a tumor tissue section. In some embodiments, the tumor tissue section is a fixed tumor tissue section (e.g., a formal-fixed paraffin-embedded tumor tissue section). In some embodiments, the tumor sample comprises one or more cancer tumors. Numerous types of cancer are known in the art. In some embodiments, the tissue sample is derived from a biopsy sample. In some embodiments, the tissue sample is derived from a whole rodent embryo. In some embodiments, the tissue is selected from, but not limited to, brain tissue, breast tissue, colon tissue, heart tissue, lung tissue, spleen tissue, testes tissue, inflamed tonsil tissue, cervix tissue, and lymph node tissue.

In some embodiments, an FFPE sample is deparaffinized and decrosslinked prior to delivering a plurality of templated ligation probes (e.g., RNA templated ligation probes) and analyte capture agents. In some embodiments, an FFPE biological sample is deparaffinized and decrosslinked before step (b). For example, the paraffin-embedding material can be removed (e.g., deparaffinization) from the biological sample (e.g., tissue section) by incubating the biological sample in an appropriate solvent (e.g., xylene), followed by a series of rinses (e.g., ethanol of varying concentrations), and rehydration in water. In some embodiments, the biological sample can be dried following deparaffinization. In some embodiments, after the step of drying the biological sample, the biological sample can be stained (e.g., H&E stain, any of the variety of stains described herein).

In some embodiments, the method includes staining the biological sample. In some embodiments, the staining includes the use of hematoxylin and eosin. In some embodiments, a biological sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin.

The biological sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the staining includes the use of a detectable label selected from the group consisting of a radioisotope, a fluorophore, a chemiluminescent compound, a bioluminescent compound, or a combination thereof.

In some embodiments, the biological sample is imaged after staining the biological sample. In some embodiments, the biological sample is imaged prior to staining the biological sample. In some embodiments, the biological sample is visualized or imaged using bright field microscopy. In some embodiments, the biological sample is visualized or imaged using fluorescence microscopy. Additional methods of visualization and imaging are known in the art. Non-limiting examples of visualization and imaging include expansion microscopy, bright field microscopy, dark field microscopy, phase contrast microscopy, electron microscopy, fluorescence microscopy, reflection microscopy, interference microscopy and confocal microscopy. In some embodiments, the sample is stained and imaged prior to adding the first and/or second primer to the biological sample on the array.

After a fixed (e.g., FFPE, PFA, acetone, methanol) biological sample has undergone deparaffinization, the fixed (e.g., FFPE, PFA) biological sample can be further processed. For example, fixed (e.g., FFPE, PFA) biological samples can be treated to remove crosslinks (e.g., formaldehyde-induced crosslinks (e.g., decrosslinking)). In some embodiments, decrosslinking the crosslinks (e.g., formaldehyde-induced crosslinks) in the fixed (e.g., FFPE, PFA) biological sample can include treating the sample with heat. In some embodiments, decrosslinking the formaldehyde-induced crosslinks can include performing a chemical reaction. In some embodiments, decrosslinking the formaldehyde-induced crosslinks, can include treating the sample with a permeabilization reagent. In some embodiments, decrosslinking the formaldehyde-induced crosslinks can include heat, a chemical reaction, and/or permeabilization reagents.

In some embodiments, decrosslinking crosslinks (e.g., formaldehyde-induced crosslinks) can be performed in the presence of a buffer. In some embodiments, the buffer is Tris-EDTA (TE) buffer (e.g., TE buffer for FFPE biological samples). In some embodiments, the buffer is citrate buffer (e.g., citrate buffer for FFPE biological samples). In some embodiments, the buffer is Tris-HCl buffer (e.g., Tris-HCl buffer for PFA fixed biological samples). In some embodiments, the buffer (e.g., TE buffer, Tris-HCl buffer) has a pH of about 5.0 to about 10.0 and a temperature between about 60° C. to about 100° C.

In some embodiments, the biological sample is permeabilized (e.g., permeabilized by any of the methods described herein). In some embodiments, the permeabilization is an enzymatic permeabilization. In some embodiments, the permeabilization is a chemical permeabilization. In some embodiments, the biological sample is permeabilized before delivering the RNA templated ligation probes and analyte capture agents to the biological sample. In some embodiments, the biological sample is permeabilized at the same time as the RNA templated ligation probes and analyte capture agents are delivered to the biological sample. In some embodiments, the biological sample is permeabilized after the RNA templated ligation probes and analyte capture agents are delivered to the biological sample. In some embodiments, hybridizing the RNA templated ligation products to the second capture domains and the analyte capture sequences of the bound analyte capture agents to the first capture domains further comprises permeabilizing the biological sample.

In some embodiments, the biological sample is permeabilized from about 30 to about 120 minutes, from about 40 to about 110 minutes, from about 50 to about 100 minutes, from about 60 to about 90 minutes, or from about 70 to about 80 minutes. In some embodiments, the biological samples is permeabilized about 30, about 35, about 40, about 45, about 50, about 55, about 60, about 65, about 70, about 75, about 80, about 90, about 95, about 100, about 105, about 110, about 115, or about 130 minutes.

In some embodiments, the permeabilization buffer comprises urea. In some embodiments, the urea is at a concentration of about 0.5M to 3.0M. In some embodiments, the concentration of the urea is about 0.5, 1.0, 1.5, 2.0, 2.5, or about 3.0M. In some embodiments, the permeabilization buffer includes a detergent. In some embodiments, the detergent is sarkosyl. In some embodiments, the sarkosyl is present at about 2% to about 10% (v/v). In some embodiments, the sarkosyl is present at about 3%, 4%, 5%, 6%, 7%, 8%, or 9% (v/v). In some embodiments, the permeabilization buffer comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v).

In some embodiments, the method includes a step of permeabilizing the biological sample (e.g., a tissue section). For example, the biological sample can be permeabilized to facilitate transfer of the extended products to the capture probes on the array. In some embodiments, the permeabilizing includes the use of an organic solvent (e.g., acetone, ethanol, and methanol), a detergent (e.g., saponin, Triton X-100™, Tween-20™, or sodium dodecyl sulfate (SDS)), and an enzyme (an endopeptidase, an exopeptidase, a protease), or combinations thereof. In some embodiments, the permeabilizing includes the use of an endopeptidase, a protease, SDS, polyethylene glycol tert-octylphenyl ether, polysorbate 80, and polysorbate 20, N-lauroylsarcosine sodium salt solution, saponin, Triton X100™, Tween-20™, or combinations thereof. In some embodiments, the endopeptidase is pepsin. In some embodiments, the endopeptidase is Proteinase K. Additional methods for sample permeabilization are described, for example, in Jamur et al., Method Mol. Biol. 588:63-66, 2010, the entire contents of which are incorporated herein by reference.

The methods provided herein can also include antibody staining. In some embodiment, antibody staining includes the use of an antibody staining buffer. In some embodiments, the antibody staining buffer (e.g., a PBS-based buffer) includes a detergent (e.g., Tween-20, SDS, sarkosyl). In some embodiments, the antibody staining buffer includes a serum, such as for example, a goat serum. In some embodiments, the goat serum is from about 1% to about 10% (v/v), from about 2% to about 9% (v/v), from about 3% to about 8% (v/v), or about 4% to about 7% (v/v). In some embodiments, the antibody staining buffer includes dextran sulfate. In some embodiments, the dextran sulfate is at a concentration of about 1 mg/ml to about 20 mg/ml, from about 5 mg/ml to about 15 mg/ml, or from about 8 mg/ml to about 12 mg/ml.

The methods provided herein can also utilize blocking probes to block the non-specific binding (e.g., hybridization) of the analyte capture sequence and the capture domain of a capture probe on an array. In some embodiments, following contact between the biological sample and the array, the biological sample is contacted with a plurality of analyte capture agents, where an analyte capture agent includes an analyte capture sequence that is reversibly blocked with a blocking probe. In some embodiments, the analyte capture sequence is reversibly blocked with more than one blocking probe (e.g., 2, 3, 4, or more blocking probes). In some embodiments, the analyte capture agent is blocked prior to binding the target analyte (e.g., a target protein).

In some embodiments, the oligonucleotide of the analyte capture agent (e.g., analyte capture sequence) is blocked by a blocking probe. In some embodiments, blocking probes are hybridized to the analyte capture sequence of the analyte capture agents before introducing the analyte capture agents to a biological sample. In some embodiments, blocking probes are hybridized to the analyte capture sequence of the analyte capture agents after introducing the analyte capture agents to the biological sample. In such embodiments, the capture domain can also be blocked to prevent non-specific binding, and/or to control the time of binding, between the analyte capture sequence and the capture domain. In some embodiments, the blocking probes can be alternatively or additionally introduced during staining of the biological sample. In some embodiments, the analyte capture sequence is blocked prior to binding to the capture domain, where the blocking probe includes a sequence complementary or substantially complementary to the analyte capture sequence.

In some embodiments, the analyte capture sequence is blocked with one blocking probe. In some embodiments, the analyte capture sequence is blocked with two blocking probes. In some embodiments, the analyte capture sequence is blocked with more than two blocking probes (e.g., 3, 4, 5, or more blocking probes). In some embodiments, a blocking probe is used to block the free 3' end of the analyte capture sequence. In some embodiments, a blocking probe is used to block the 5' end of the analyte capture sequence. In some embodiments, two blocking probes are used to block both 5' and 3' ends of the analyte capture sequence. In some embodiments, both the analyte capture sequence and the capture probe domain are blocked.

In some embodiments, the blocking probes can differ in length and/or complexity. In some embodiments, the blocking probe can include a nucleotide sequence of about 8 to about 24 nucleotides in length (e.g., about 8 to about 22, about 8 to about 20, about 8 to about 18, about 8 to about 16, about 8 to about 14, about 8 to about 12, about 8 to about 10, about 10 to about 24, about 10 to about 22, about 10 to about 20, about 10 to about 18, about 10 to about 16, about 10 to about 14, about 10 to about 12, about 12 to about 24, about 12 to about 22, about 12 to about 20, about 12 to about 18, about 12 to about 16, about 12 to about 14, about 14 to about 24, about 14 to about 22, about 14 to about 20, about 14 to about 18, about 14 to about 16, about 16 to about 24, about 16 to about 22, about 16 to about 20, about 16 to about 18, about 18 to about 24, about 18 to about 22, about 18 to about 20, about 20 to about 24, about 20 to about 22, or about 22 to about 24 nucleotides in length).

In some embodiments, the blocking probe is removed prior to hybridizing the analyte capture sequence of the oligonucleotide of the analyte capture sequence to the first capture domain. For example, once the blocking probe is released from the analyte capture sequence, the analyte capture sequence can bind to the first capture domain on the array. In some embodiments, blocking the analyte capture sequence reduces non-specific background staining. In some embodiments, blocking the analyte capture sequence allows for control over when to allow the binding of the analyte capture sequence to the capture domain of a capture probe during a spatial workflow, thereby controlling the time of capture of the analyte capture sequence on the array. In some embodiments, the blocking probes are reversibly bound, such that the blocking probes can be removed from the analyte capture sequence during or after the time that analyte capture agents are in contact with the biological sample. In some embodiments, the blocking probe can be removed with RNAse treatment (e.g., RNAse H treatment). In some embodiments, the blocking probes are removed by increasing the temperature (e.g., heating) the biological sample. In some embodiments, the blocking probes are removed enzymatically (e.g., cleaved). In some embodiments, the blocking probes are removed by a USER enzyme. In some embodiments, the blocking probes are removed by an endonuclease. In some embodiments, the endonuclease is endonuclease IV. In some embodiments, the endonuclease is endonuclease V.

In some embodiments, the determining in step (g) includes a) extending the captured ligation products and the captured oligonucleotides of the analyte capture agents, wherein the extension products comprise the spatial barcode or a complement thereof, b) releasing the extension products, or complements thereof, from the spatial array, c) producing a library from the released extension products or complements thereof, and d) sequencing the library. In some embodiments, extension (e.g., extension of captured nucleic acid ligation products and the captured oligonucleotides of the analyte capture agents and/or extension of the plurality of captures probes) is performed with a polymerase (e.g., any suitable polymerase, e.g., T4 polymerase).

In some embodiments, the released extension products can be prepared for downstream applications, such as generation of a sequencing library and next-generation sequencing. Producing sequencing libraries are known in the art. For example, the released extension products can be purified and collected for downstream amplification steps. The released extension products can be amplified using PCR, where primer binding sites flank the spatial barcode and ligation product or analyte binding moiety barcode, or complements thereof, generating a library associated with a particular spatial barcode. In some embodiments, the library preparation can be quantitated and/or quality controlled to verify the success of the library preparation steps. The library amplicons are sequenced and analyzed to decode spatial information and the ligation product or analyte binding moiety barcode, or complements thereof.

Alternatively or additionally, the amplicons can then be enzymatically fragmented and/or size-selected in order to provide for desired amplicon size. In some embodiments, when utilizing an Illumina® library preparation methodology, for example, P5 and P7, sequences can be added to the amplicons thereby allowing for capture of the library preparation on a sequencing flowcell (e.g., on Illumina sequencing instruments). Additionally, i7 and i5 can index sequences be added as sample indexes if multiple libraries are to be pooled and sequenced together. Further, Read 1 and Read 2 sequences can be added to the library preparation for sequencing purposes. The aforementioned sequences can be added to a library preparation sample, for example, via End Repair, A-tailing, Adaptor Ligation, and/or PCR. The cDNA fragments can then be sequenced using, for example, paired-end sequencing using TruSeq Read 1 and TruSeq Read 2 as sequencing primer sites, although other methods are known in the art.

In some embodiments, the determining in step (g) can include a pre-amplification step. For example, a complementary strand to the extended RNA ligation products and/or the extension product of the captured oligonucleotides of the analyte capture agents the step can be generated and further include a pre-amplification step of the extension products or complements thereof (e.g., extended products) prior to library production (e.g., RTL library production; captured oligonucleotide of the analyte capture agent production).

Compositions

Figure 26:
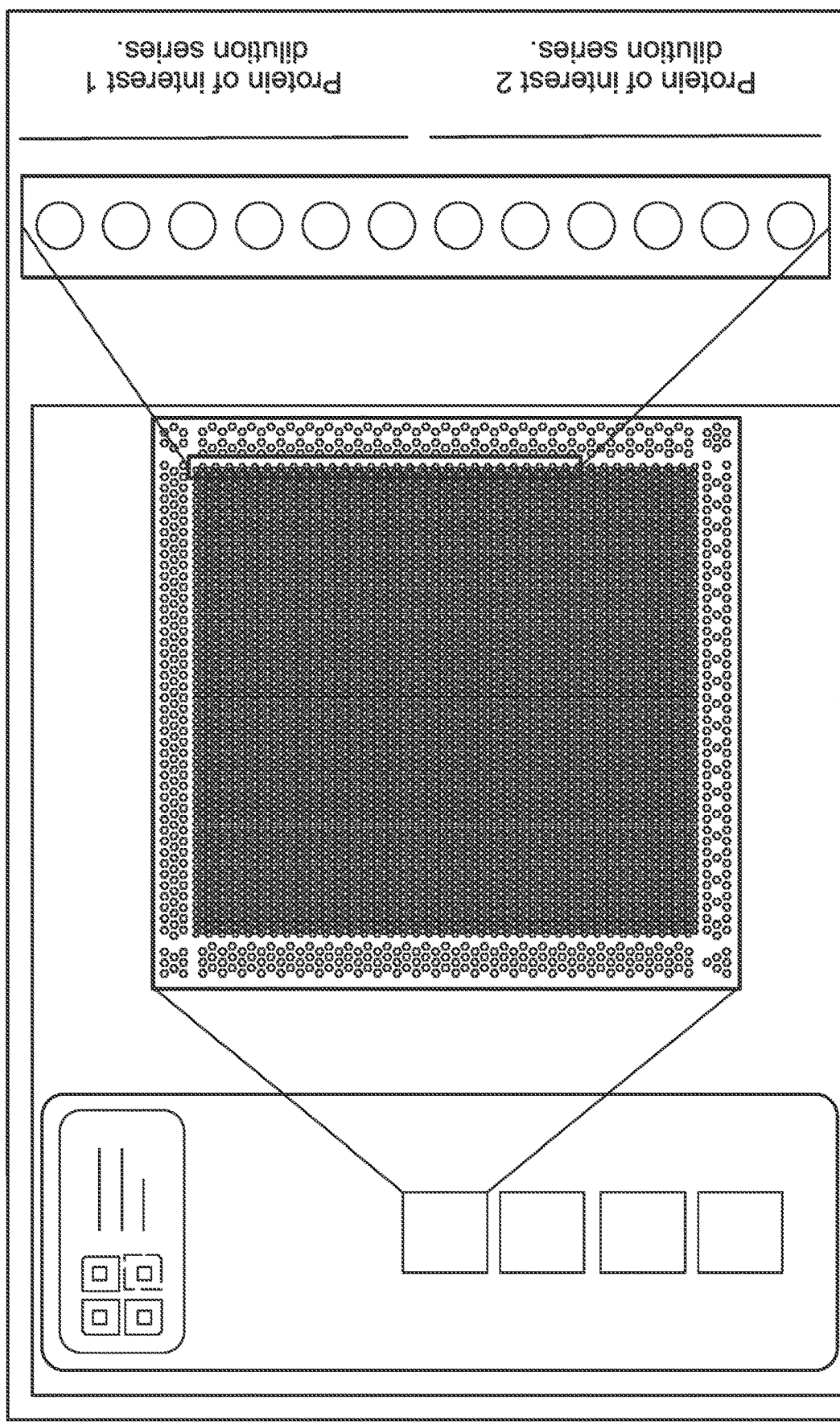
FIG. 26 shows an exemplary spatial array with multiple protein dilution series spotted on the spatial array.

Also provided herein are spatial arrays, including spatial arrays described in the methods herein, that include a dilution series of protein standards directly on the array. In general, protein quantification with antibodies can be difficult due to the varying affinity antibodies have for their protein targets. In order to accurately quantify protein abundance with antibodies, standard curves with the protein of interest (e.g., similar to an ELISA assay) can be applied to a spatial array in parallel with spatial proteomic analysis. In some embodiments, a protein standard is spotted on the array (e.g., on top of the features of the array). In some embodiments, more than one protein standard is spotted on the array (e.g., 2, 3, 4, 5, 6, 7, 8, 9, 10, 11, 12, 13, 14, 15, 16, 17, 18, 19, 20, or more protein standards are spotted on the array). Readout from the internal protein standard series allows for quantification of proteins of interest in parallel from the biological sample (e.g., a tissue section) directly on the array which can lead to increased accuracy when determining protein concentration. FIG. 26 shows an exemplary substrate with an exemplary configuration that includes a dilution series for two different proteins spotted on the margins of a spatial array. FIG. 26 shows a dilution series for two proteins of interest, however, as described herein more than two protein dilution series can be spotted on the spatial array.

Provided herein are compositions such as spatial arrays including a) a plurality of capture probes including spatial barcodes and a first plurality of capture domains hybridized to a plurality of templated ligation products, and b) a plurality of capture probes comprising spatial barcodes and a second plurality of capture domains hybridized to a plurality of oligonucleotides from analyte capture agents, wherein the oligonucleotides comprise an analyte capture sequence and an analyte binding moiety barcode. In some compositions, the analyte capture sequences of the oligonucleotides are hybridized to the second plurality of capture domains.

In some compositions, the capture probes include cleavage domains, unique molecular identifiers, functional sequences, or combinations thereof. In some compositions, the first plurality of capture domains are homopolymeric sequences. In some compositions, the first plurality of capture domains comprise poly(T) sequences. In some compositions, the first plurality of capture domains are defined non-homopolymeric sequences. In some compositions the first plurality of capture domains comprise a degenerate sequence. In some compositions, the first plurality of capture domains comprise a fixed sequence. For example, the first plurality of capture domains can comprise one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some compositions, the second plurality of capture domains are homopolymeric sequences. In some compositions, the second plurality of capture domains are defined non-homopolymeric sequences. In some compositions, the second plurality of capture domains comprise poly(T) sequences. In some compositions the second plurality of capture domains comprise a degenerate sequence. In some compositions, the second plurality of capture domains comprise a fixed sequence. For example, the second plurality of capture domains can comprise one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some compositions, the spatial array comprises one or more protein dilution series.

Kits

Also provided herein are kits including a) a spatial array comprising a plurality of capture probes, where the capture probes include spatial barcodes and wherein the plurality of capture probes comprise a first plurality of first capture domains and a second plurality of second capture domains, b) one or more analyte capture agents, c) one or more RNA templated ligation probe pairs, and d) one or more enzymes and buffers for practicing any of the methods described herein. In some kits, one or more enzymes includes polymerases, RNases, DNases, proteases, lipases, or combinations thereof.

```
SEQUENCE LISTING
Capture Domain 22mer
                                        SEQ ID NO: 1
TTGCTAGGACCGGCCTTAAAGC Capture Domain 21mer
                                        SEQ ID NO: 2
TTGCTAGGACCGGCCTTAAAG Capture Domain 20mer
                                        SEQ ID NO: 3
TTGCTAGGACCGGCCTTAAA Capture Domain 19mer
                                        SEQ ID NO: 4
TTGCTAGGACCGGCCTTAA Capture Domain 18mer
                                        SEQ ID NO: 5
TTGCTAGGACCGGCCTTA Capture Domain 17mer
                                        SEQ ID NO: 6
TTGCTAGGACCGGCCTT Capture Domain 16mer
                                        SEQ ID NO: 7
TTGCTAGGACCGGCCT Capture Domain 15mer
                                        SEQ ID NO: 8
TTGCTAGGACCGGCC Capture Domain 14mer
                                        SEQ ID NO: 9
TTGCTAGGACCGGC Capture Domain 13mer
                                        SEQ ID NO: 10
TTGCTAGGACCGG Capture Domain 12mer
                                        SEQ ID NO: 11
TTGCTAGGACCG
```

EXAMPLES

Example 1. Spatial Proteomics and Gene Expression on FFPE Human Lymph Nodes

Experiments were undertaken to determine whether analyte capture agents could provide for protein expression analysis concurrently with associated gene expression. In these experiments, the analyte capture agent includes an antibody as the analyte binding moiety and the analyte capture sequence that comprises a barcode sequence that identifies the antibody as well as the capture sequence that is complementary to the associated capture probe capture domain on the array.

Templated ligation probes were allowed to hybridize to their target mRNAs and antibody-oligonucleotide conjugates were incubated with the samples wherein the antibodies were allowed to bind to their protein targets (as described in PCT/US2020/66720). Briefly, FFPE human lymph nodes tissues were sectioned, mounted on spatial array slides and deparaffinized using a series of xylene and ethanol washes prior to brightfield imaging. Tissues were washed and decrosslinked by incubating the tissues in TE (pH 9.0) buffer for 1 hr at 70° C. After decrosslinking the tissues, the targeted templated ligation probes were added to the tissues and probe hybridization ran overnight at 50° C. Post hybridization, the probes were ligated together at 37° C. for 1 hr. Following templated ligation probe hybridization the analyte capture agents were added to the tissues, which were incubated in an antibody staining buffer with the tissues overnight at room temperature. The tissue samples were washed four times with the antibody staining buffer without antibodies.

Tissues were permeabilized and the ligated probe products, or ligation products, were allowed to migrate for hybridization to the capture domains of the capture probes on the spatial array surface. The oligonucleotides of the analyte capture agents also migrated in parallel and were captured via their capture sequences that hybridized to capture probe capture domains on the spatial array that are complementary to the capture sequences. As such, the ligation products representing the target mRNAs and the oligonucleotides of the analyte capture agents representing the binding of the antibodies to the targeted proteins were concurrently captured on the array surface. To allow for probe and oligonucleotide release and capture, the tissues were incubated with RNAse H and an associated buffer for 30 min at 37° C., tissues permeabilized using a protease for an additional 40 min., followed by washing to remove the enzymes from the tissues.

The captured ligation products and the analyte binding agent oligonucleotides were extended to create extended products of the captured molecules including the spatial barcode or a complement thereof, the analyte binding moiety barcode if present and other functional sequences from the capture probe. Library preparations were made, the libraries sequenced on an Illumina sequencing instrument, and spatial locations determined using Space Ranger and Loupe Browser (10× Genomics). The antibody sequences (e.g., the complement of the captured oligonucleotide from the analyte binding agents) were amplified with Truseq_pR1 and Truseq_pR2. For protein localization, sequences relating to the analyte binding moiety barcode were used to determine abundance and location of the labeled protein by the analyte binding agents. Spatial expression patterns were determined using SpaceRanger data analysis software and Loupe browser visualization software (10× Genomics).

Figure 4A:
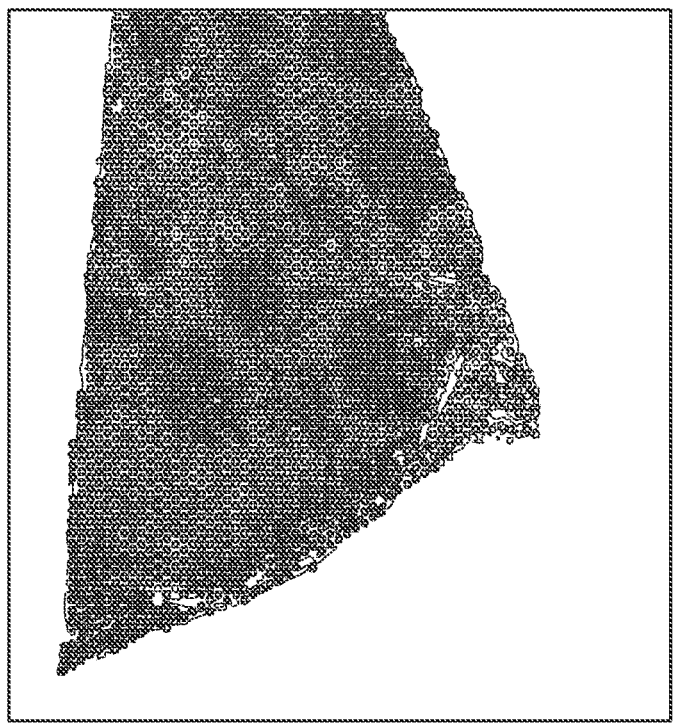
FIGS. 4A-B shows exemplary clustering data for FFPE human lymph node sections using an eight-plex antibody-oligonucleotide conjugate test panel.
Figure 4B:
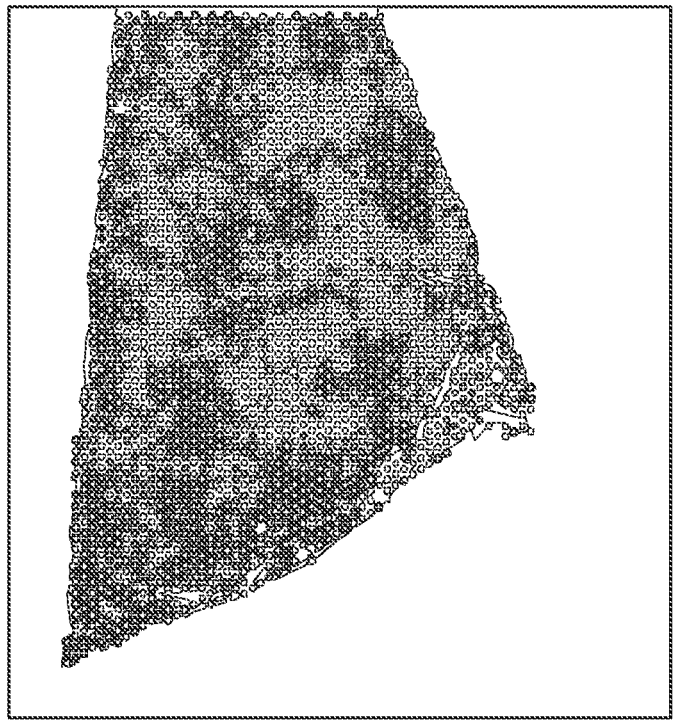

FIGS. 4A-B demonstrates the results of an experiment where analyte capture agents were combined to determine whether multiple targets could be identified concurrently in a tissue. In this experiment, eight different antibodies were conjugated to oligonucleotides comprising analyte binding moiety barcodes and capture sequences targeting eight proteins: NCAM1, Ki67, CD8A, PDL1, CD20, CD11B, CD45RA and CD66B. FIG. 4A (RNA) shows the spatial gene expression clustering of the associated protein in the lymph node tissue sample, whereas FIG. 4B (protein) shows the spatial protein expression clustering of the eight targets. This experiment demonstrates that it is feasible to multiplex different analyte capture agents to concurrently identify the spatial gene and protein expression patterns of multiplex targets in a tissue sample.

Additional experimental results from the multiplexed experiment shown in FIG. 4A included targeting CD20 and CD20 mRNA when only one protein is targeted with an analyte capture agent. These results (data not shown) show a lymph node tissue sample where an antibody directed to CD20 was conjugated to an oligonucleotide for subsequent capture on a spatial array. mRNA from the tissue section was successfully captured and extended thereby providing CD20 spatial gene expression analysis (data not shown). Concurrently, spatially presented protein array demonstrates that the CD20 antibody of the analyte capture agent was able to bind to the CD20 protein followed by oligonucleotide capture on the spatial array, extension and spatial determination of the location of the CD20 protein via the analyte binding moiety barcode (data not shown). Gene expression and protein expression patterns for CD20 overlap and were localized to B-cells in the lymph nodes (data not shown). As such, the methods demonstrate the utility of the analyte capture agents to target a protein of interest and simultaneously detect spatial gene expression and protein expression in a tissue sample.

Additional data was generated with the target CD8A (e.g., using a CD8A antibody) similar to CD20 described above. The spatial gene expression and protein expression patterns were consistent with the targeting of cytotoxic CD8 positive T cells in the lymph node tissue (data not shown), again demonstrating the utility of the methods and analyte binding agents that target specific proteins of interest for simultaneously determining spatial gene and protein expression of a given target.

Example 2. Spatial Proteomics and Gene Expression on FFPE Human Tonsil Tissue

As described above experiments were undertaken to determine whether analyte capture agents could provide for protein expression analysis concurrently with associated gene expression in FFPE human tonsil tissue.

Briefly, FFPE human tonsil tissues were sectioned, mounted on spatial array slides and deparaffinized using a series of xylene and ethanol washes prior to H&E staining and brightfield imaging. Tissues were washed and decrosslinked by incubating the tissues in citrate buffer (pH 6.0) for 1 hour at 90° C. After decrosslinking the tissues, the targeted ligation probes were applied to the tissues and probe hybridization ran overnight at 50° C. Post hybridization, the probes were ligated together at 37° C. for 1 hour to generate ligation products. Following ligation probe hybridization the analyte capture agents were applied to the tissues, which were incubated in an antibody staining buffer (PBS-based buffer, 5% goat serum, salmon sperm DNA and dextran sulfate) with the tissues overnight at 4° C. The tissue samples were washed four times with antibody-free antibody staining buffer.

Tissues were permeabilized and the ligation products were allowed to migrate for capture by hybridization to the capture domains of the capture probes on the spatial array surface. The oligonucleotides of the analyte capture agents complementary to the alternative capture sequences of the second set of capture probes on the array were also captured by hybridization. As such, both ligation products representing the mRNA of the targeted protein and the oligonucleotide of the analyte capture agent representing the binding of the antibody to the targeted protein were concurrently captured on the array surface. To allow for probe and oligonucleotide release and capture, the tissues were incubated with RNase H and an associated buffer, and polyethylene glycol (PEG) for 30 minutes at 37° C. Tissues were permeabilized using a permeabilization buffer comprising a protease (e.g., Proteinase K), PEG, 1M urea, for an additional 60 minutes, followed by washing to remove the enzymes from the tissues.

The captured ligation products and the analyte binding agent oligonucleotides were extended to include the spatial barcode or a complement thereof, the analyte binding moiety barcode or a complement thereof if present and other functional sequences from the capture probe. Additionally, said products were pre-amplified prior to library preparation.

Library preparations were made from the extended products, the libraries sequenced on an Illumina sequencing instrument, and spatial locations determined and visualized. The antibody sequences (e.g., the complement of the captured oligonucleotide from the analyte binding agents) were amplified with Truseq_pR1 and Truseq_pR2. For protein localization, sequences relating to the analyte binding moiety barcode were used to determine abundance and location of the labeled protein by the analyte binding agents. Spatial expression patterns were determined using SpaceRanger data analysis software and Loupe browser visualization software (10× Genomics).

Figure 5:
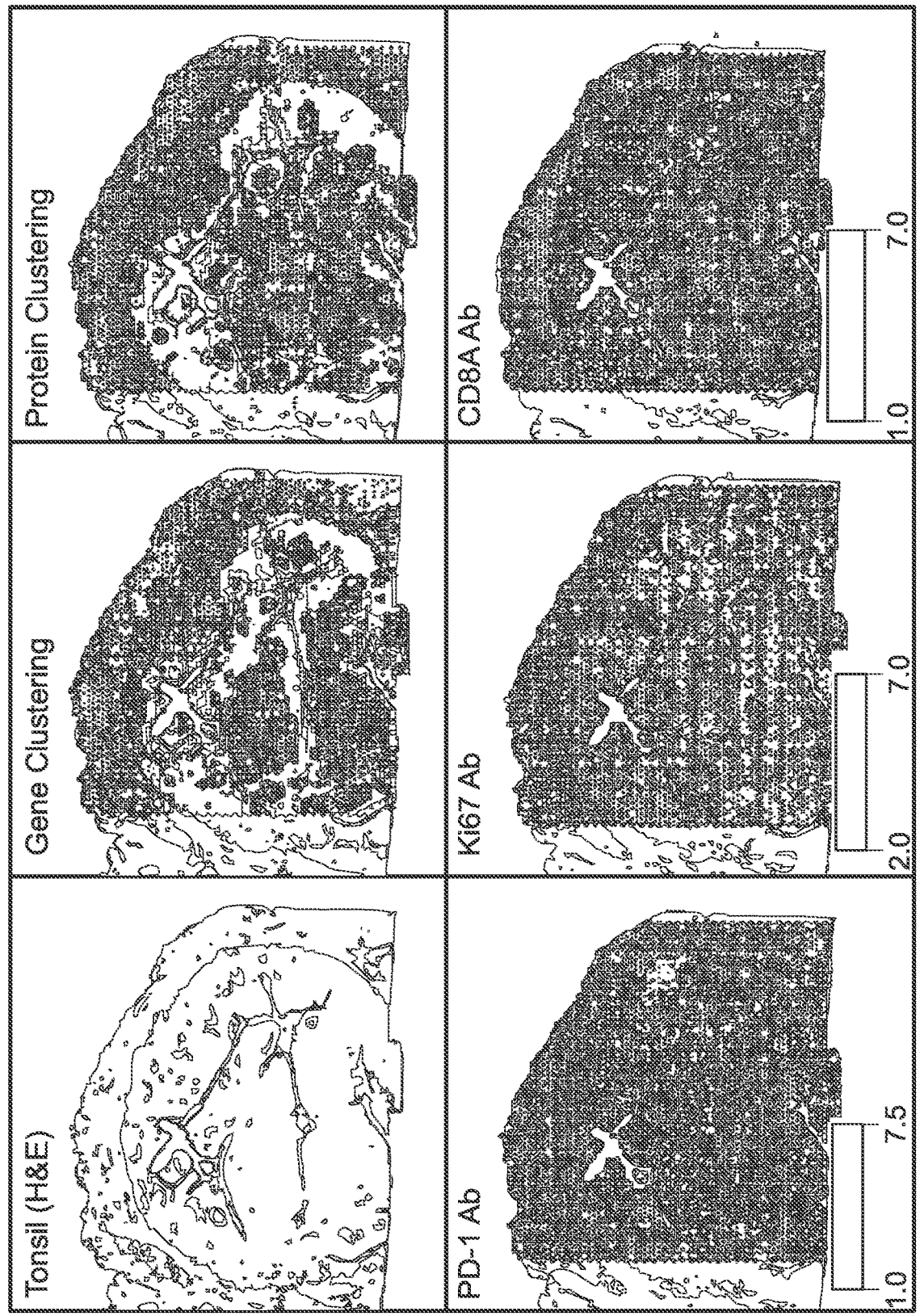
FIG. 5 shows exemplary clustering data of spatial gene (top middle) and protein expression (top right) in FFPE tonsil tissue sections superimposed on the H&E image (top left). Bottom figures show visualization of PD-1, Ki67, and CD8A protein markers labeling the follicular T cells, individual follicles, and suppressor/cytotoxic T cells, respectively.

FIG. 5 shows exemplary clustering data of spatial gene (top middle) and protein expression (top right) in FFPE tonsil tissue sections superimposed on the H&E image (top left). FIG. 5 (bottom) shows visualization of PD-1, Ki67, and CD8A protein markers labeling the follicular T cells, individual follicles, and suppressor/cytotoxic T cells, respectively. The data demonstrate the utility of analyte capture agents to target a protein of interest and simultaneously detect spatial gene expression in FFPE tonsil tissue samples. In addition, the data demonstrate the specificity of the protein markers (e.g., antibodies) to identify different cell types within a heterogeneous tissue section and simultaneously detect spatial gene expression.

In another experiment performed on FFPE tonsil tissue sections exemplary spatial gene and protein expression for a 20-plex antibody-oligonucleotide conjugate targeting proteins of interest and RNA templated probes targeting 18,000 mRNA targets was performed. The FFPE human tonsil tissue section was H&E stained which identified where follicles containing maturing immune cells and the epithelial layer can be seen (data not shown). Representative gene expression cluster data and representative protein expression cluster data align with the macroscopic structures visible in the H&E image shown (data not shown).

The data demonstrate the feasibility of multiplexing different analyte capture agents to concurrently identify the spatial gene and protein expression patterns of multiplex targets in a tissue sample.

Figure 6:
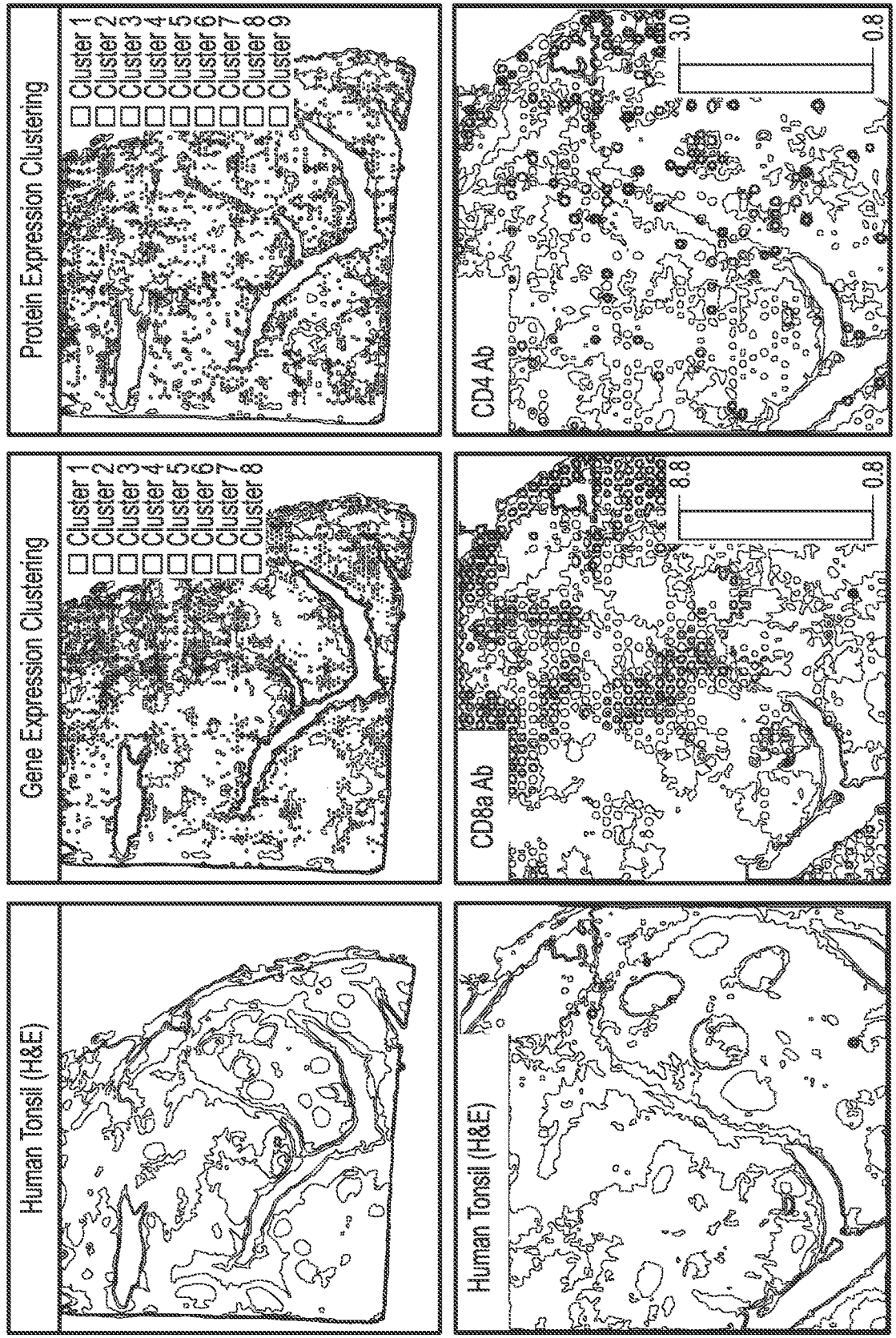
FIG. 6 shows exemplary H&E stained FFPE tonsil tissue section (top left), spatial gene expression data (top middle), and spatial protein expression data (top left).

FIG. 6 shows an exemplary H&E stained FFPE tonsil tissue section and spatial and gene expression data (top). FIG. 6 also shows an expanded view of the H&E stained FFPE tonsil tissue section and clustering of gene expression and protein expression of CD8a and CD4 superimposed on the H&E FFPE tonsil tissue section (bottom). Visualization of the CD8a and CD4 markers coincide with the follicles shown in the H&E staining where CD8a localizes to the edge of the follicles and CD4 localizes outside the follicles.

Additional exemplary clustering data of spatial gene and protein expression was performed on a different FFPE tonsil tissue sections. Spatial gene expression clustering, spatial protein clustering was performed on the FFPE tonsil tissue sample which was also H&E stained (data not shown). The results demonstrate an experiment where analyte capture agents were combined to determine whether multiple targets could be identified concurrently in FFPE tonsil tissue. In this experiment 21 different antibodies were conjugated to oligonucleotides comprising analyte binding moiety barcodes and capture sequences (e.g., analyte capture sequences) targeting 21 proteins (18 shown in FIG. 7): Ki67, NCAM1, BCL, CD138, CD21, CD268, CD11b, LAG3, CD4, CD20, PD-L1, CD45RA, CD68, PanCK, CD66b, PCNA, CD235a/b and CD79a.

Figure 7:
FIG. 7 shows exemplary spatial gene and protein expression from a subset of gene and protein expression data from tonsil tissue. A subset of eighteen different targeted gene and protein expression heat maps are shown.

FIG. 7 shows a panel of 18 of the 21 targeted proteins including specifically genes: Ki67, NCAM1, BCL, CD138, CD21, CD268, CD11b, LAG3, CD4, CD20, PD-L1, CD45RA, CD68, PanCK, CD66b, PCNA, CD235a/b and CD79a. In the panel the top row shows protein expression and the bottom panel shows RNA expression. Expanded views of exemplary spatial gene and protein expression from a subset of seven different targeted gene and protein expression heat maps, including specifically: PanCK, PD-L1, Ki67, CD4, CD68, CD20, and CD11b. Gene expression (RNA) and protein expression for Ki67, NCAM1, BCl, CD138, CD11b, LAG, CD4, CD20, PD-L1, PanCK, CD66b, and CD79a as shown in FIG. 7 overlap, demonstrating the utility of the analyte capture agents to target a protein of interest and simultaneously detect spatial gene expression in FFPE tonsil tissue samples (data not shown).

Figure 8:
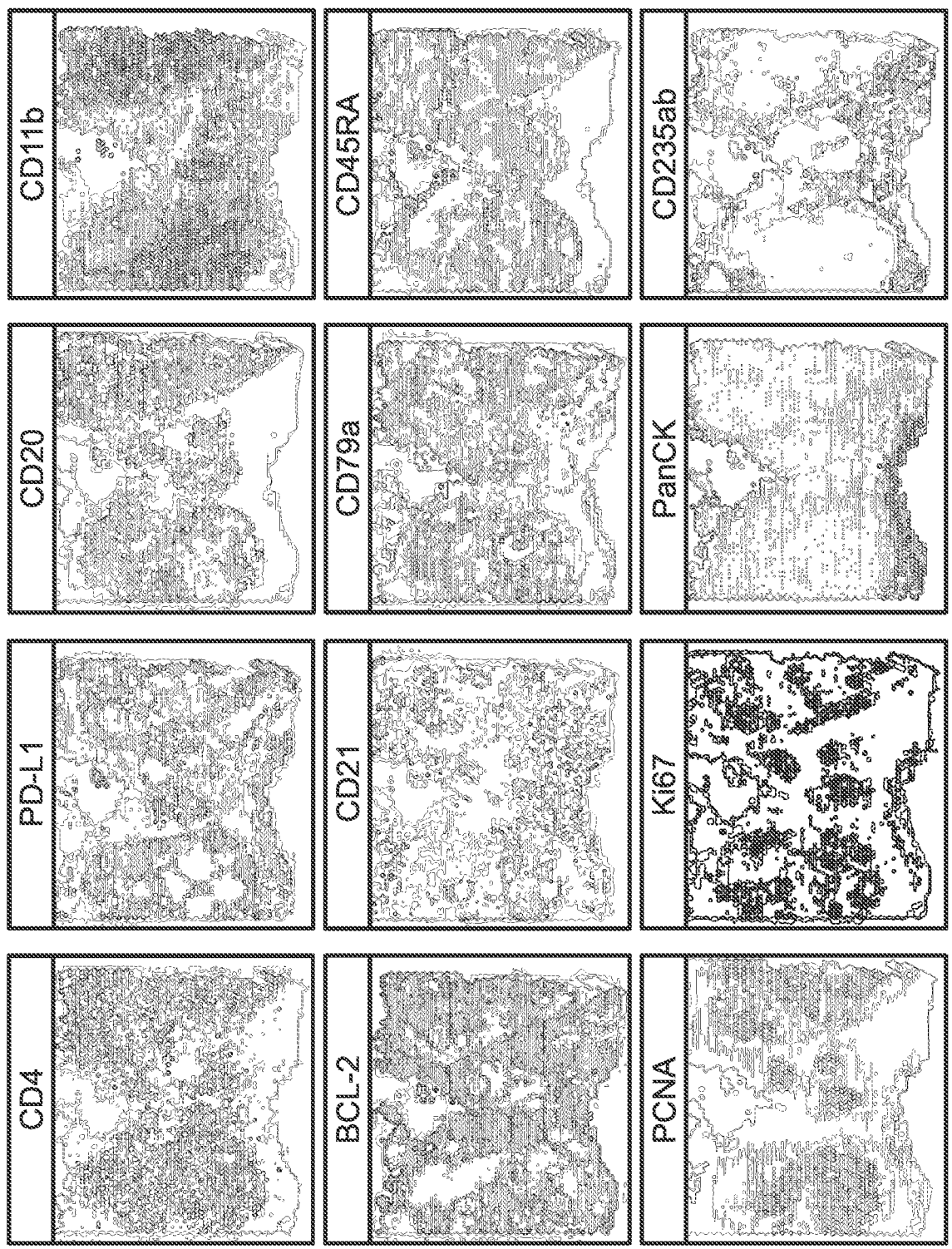
FIG. 8 shows expanded views of exemplary heat map data for FFPE human tonsil tissue section using a 12-plex antibody-oligonucleotide conjugate test panel of several genes shown in FIG. 7.

FIG. 8 shows expanded views of exemplary clustering data for FFPE human tonsil tissue using a 12-plex antibody-oligonucleotide conjugate test panel of nine genes shown in FIG. 7, including specifically: CD4, PD-L1, CD20, CD11b, BCL-2, CD21, CD791, CD45RA, PCNA, Ki67, PanCK, and CD235a/b.

Collectively, the data demonstrate the utility of the methods and analyte binding agents that target specific proteins of interest for simultaneously determining spatial gene and protein expression of a given target.

Example 3. Spatial Proteomics and Gene Expression on FFPE Breast Cancer Tissue

Human Triple Positive Breast Cancer Tissue

As described above experiments were undertaken to determine whether analyte capture agents could provide for protein expression analysis concurrently with associated gene expression in FFPE human triple positive breast cancer tissue.

Briefly, FFPE human triple positive breast cancer tissues were sectioned, mounted on spatial array slides and deparaffinized using a series of xylene and ethanol washes prior to drying at room temperature. Next, the slides were heated at 37° C. for 15 minutes, followed by a series of ethanol washes (100%, 96%, 96%, and 70% ethanol). Next, the tissues were H&E stained and brightfield imaged. Alternatively, tissues can be stained (e.g., immunofluorescence stained) instead of H&E staining.

Tissues were washed and decrosslinked by incubating the tissues in Tris-EDTA (TE) buffer (pH 9.0) for 1 hour at 95° C. followed by a series of washes with 0.1 N HCl. After decrosslinking the tissues, the targeted ligation probes were added to the tissues and probe hybridization ran overnight at 50° C. The tissues were washed in a post-hybridization buffer including 3×SSC, Baker's yeast tRNA, and nuclease free water and followed by a 2×SSC buffer wash. Post-hybridization, the probes were ligated together at 37° C. for 1 hour. Following probe hybridization, the tissues were incubated in an antibody blocking buffer (PBS-based buffer (pH 7.4), goat serum, salmon sperm DNA, Tween-20, an RNase inhibitor, and dextran sulfate) at room temperature for 60 minutes. The blocking buffer was removed from the tissues and the tissues were incubated overnight at 4° C. with the analyte capture agents in an antibody staining mixture (PBS-based buffer (pH 7.4), 5% goat serum, 0.1 µg/µL salmon sperm DNA, 0.1% Tween-20, 1 U/µL RNase inhibitor, blocking oligonucleotides, analyte capture agents (e.g., antibodies with a conjugated oligonucleotide) and 10 mg/mL dextran sulfate)). The tissue samples were washed several times with antibody staining buffer without antibodies.

Tissues were permeabilized and the ligated probes were released for capture by hybridization to the capture domains of the capture probes on the spatial array surface. The oligonucleotides of the analyte capture agents complementary to the alternative capture sequences of the second set of capture probes on the array were also captured by hybridization. As such, both ligation products representing the target mRNA and the oligonucleotide of the analyte capture agent representing the binding of the antibody to the targeted protein were concurrently captured on the array surface. To allow for probe and oligonucleotide release and capture, the tissues were incubated with an RNase (e.g., RNase H), an associated buffer, and polyethylene glycol (PEG) for 30 minutes at 37° C. Tissues were permeabilized using a permeabilization buffer comprising a protease (e.g., Proteinase K), PEG, 3M urea, for an additional 60 minutes, followed by washing to remove the enzymes from the tissues. After permeabilization the tissues were washed in 2×SSC several times.

The captured ligation products and the analyte binding agent oligonucleotides were extended to create extended products of the captured molecules including the complement of the spatial barcode, the analyte binding moiety barcode if present and other functional sequences from the capture probe. Additionally, said products were pre-amplified prior to library preparation.

Library preparations were made from the extended products, sequenced on an Illumina sequencing instrument, and spatial locations were determined and visualized. The antibody sequences (e.g., the complement of the captured oligonucleotide from the analyte binding agents) were amplified with Truseq_pR1 and Truseq_pR2. For protein localization, sequences relating to the analyte binding moiety barcode were used to determine abundance and location of the labeled protein by the analyte binding agents. Spatial expression patterns were determined using SpaceRanger data analysis software and Loupe browser visualization software (10× Genomics).

Figures 9A, 9B, 9C:
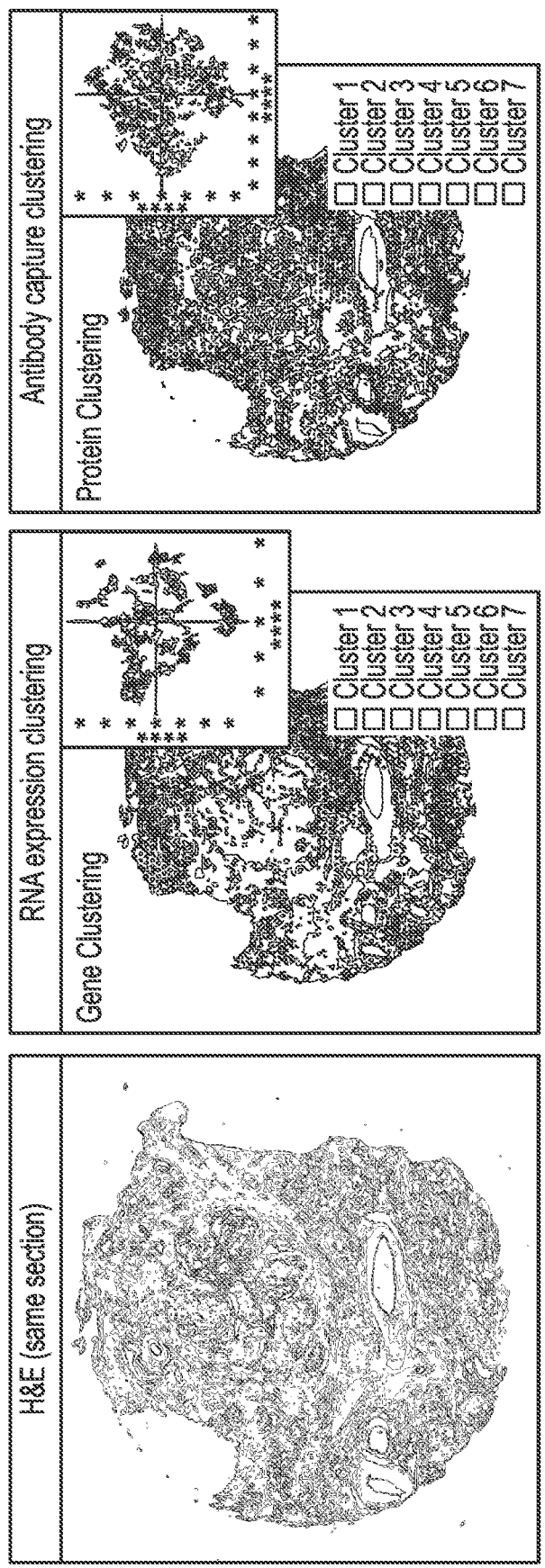
FIGS. 9A-C show exemplary spatial gene and protein expression in FFPE triple positive breast cancer tissue sections.

FIGS. 9A-C demonstrate the results of an experiment where analyte capture agents were combined to determine whether targets could be identified concurrently in grade II FFPE triple positive invasive ductal carcinoma breast cancer tissue. In this experiment 11 different antibodies were conjugated to oligonucleotides comprising analyte binding moiety barcodes and capture sequences (e.g., analyte capture sequences) targeting eleven proteins: Her2, EpCAM, PanCK, N-Cadherin, PCNA, AlphaSMA, Vimentin, CD8a, CD4, CD68, CD20, and HLA-DR. FIG. 9B (RNA) shows the spatial gene expression clustering, whereas FIG. 9C (protein) shows clustering of the associated protein in the FFPE triple positive breast cancer tissue sample. The data demonstrate the feasibility of multiplexing different analyte capture agents to concurrently identify the spatial gene and protein expression clusters patterns of multiplex targets in triple positive breast cancer tissue samples.

Figure 10:
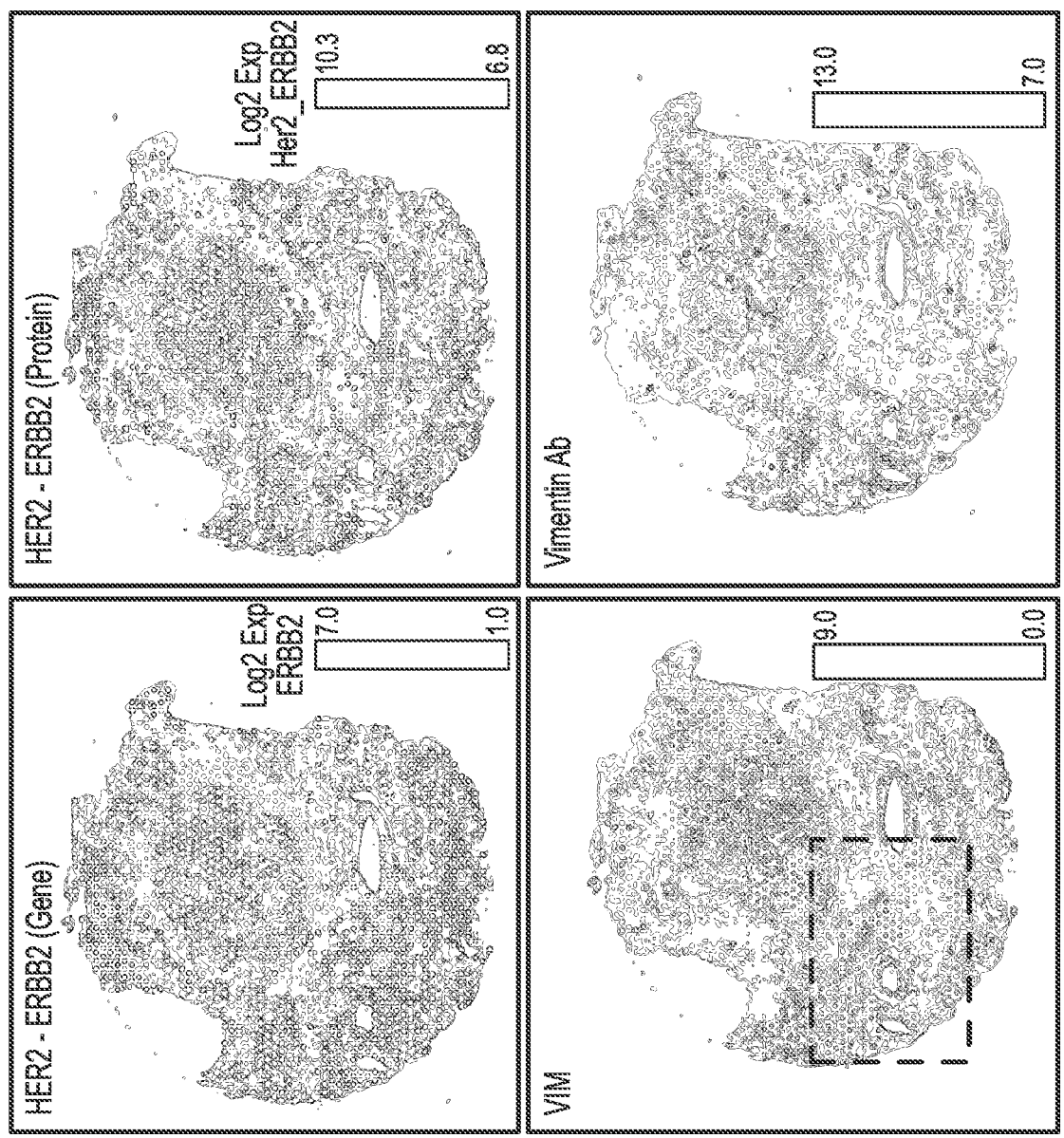
FIG. 10 shows an expanded view of Her2 and Vimentin RNA and protein expression in FFPE invasive ductal carcinoma tissue sections. Adjacent sections were immunofluorescently stained for Her2 (top) and Vimentin (bottom) demonstrating strong signal within the dashed box region of the biopsy sample.

A panel of 11 targeted proteins including specifically genes: Her2, EpCAM, PanCK, N-Cadherin, PCNA, AlphaSMA, Vimentin, CD8a, CD4, CD68, CD20, and HLA-DR was generated where for each target RNA expression and protein expression was generated (data not shown). Exemplary spatial gene and protein expression for KRT10, KRT18, and PanCK Ab was also generated and unbiased clustering of gene and protein expression superimposed on the H&E image demonstrate similar patterns (data not shown). An expanded view of Her2 and Vimentin RNA expression and protein expression is shown in FIG. 10. Adjacent sections were immunofluorescently stained for HER2 (top) and Vimentin (bottom) demonstrating strong signal within the dashed box region of the biopsy sample. Antibody staining for two biomarkers, HER2 and Vimentin, from adjacent tissue sections correlate with tumors in triple positive breast cancer tissue. Gene expression (RNA) and protein expression for Her2, EpCAM, PanCK, N-Cadherin, PCNA, AlphaSMA, Vimentin, CD8a, CD4, CD68, CD20, and HLA-DR also overlap (data not shown) demonstrating the utility of the analyte capture agents to target a protein of interest and simultaneously detect spatial gene expression in triple positive breast cancer tissue samples.

As described above experiments were undertaken to determine whether analyte capture agents could provide for protein expression analysis concurrently with associated gene expression in FFPE invasive ductal carcinoma breast cancer tissue.

Figure 12:
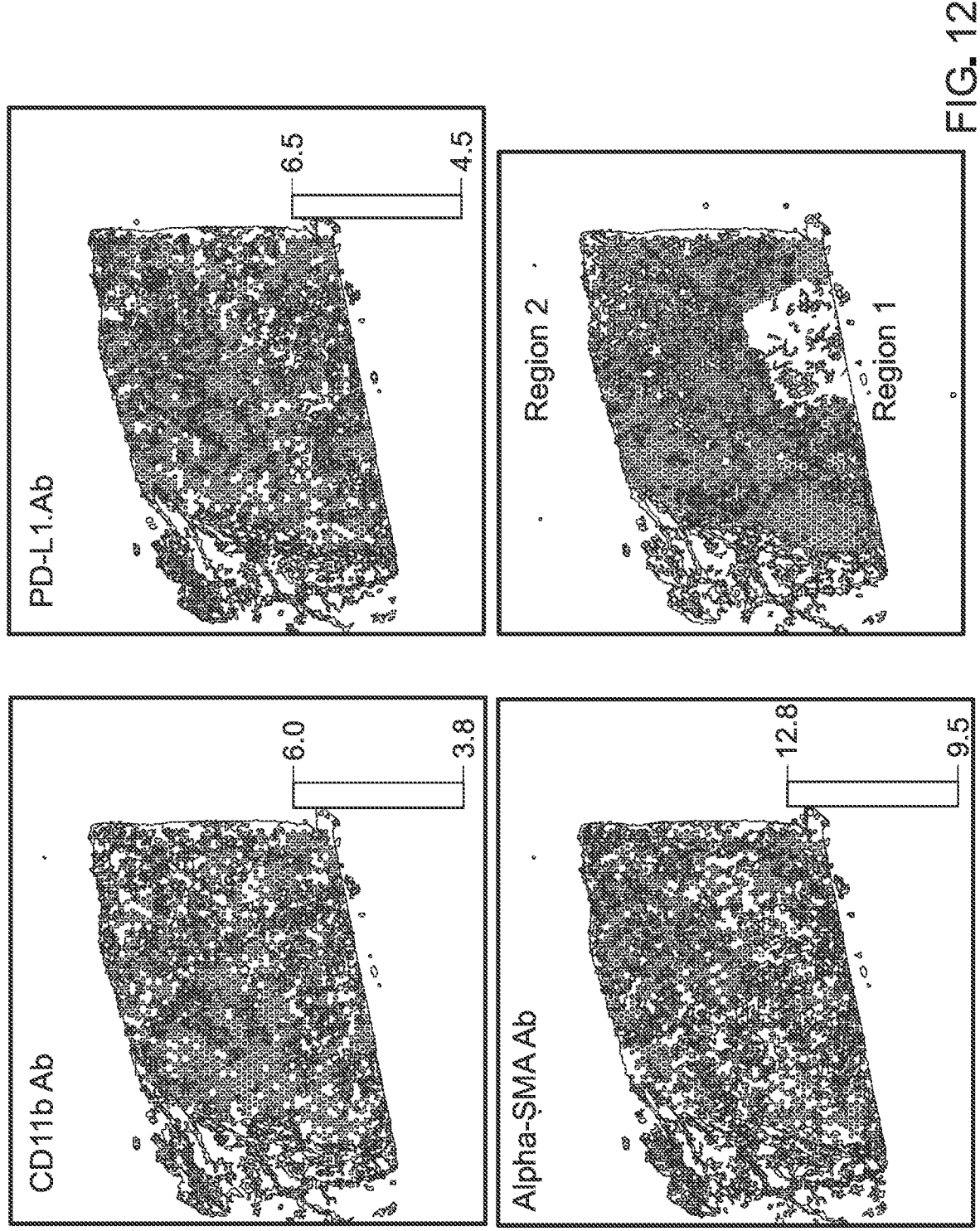
FIG. 12 shows exemplary spatial gene and protein expression from a subset of the gene and protein expression data from FIGS. 11B-C. The biomarkers were used to identify two regions of interest in the invasive ductal carcinoma tissue sample.

The samples were prepared as described above in the FFPE triple positive breast cancer example. FIGS. 11A-C show H&E-stained human invasive ductal carcinoma tissue (FIG. 11A). FIGS. 11B and 11C show gene expression clustering and protein expression clustering, respectively, superimposed on the H&E image with similar patterns. FIG. 12 shows additional examination of different biomarkers: CD11b, PD-L1, and alpha-SMA exhibit regional variation within the tissue sample. These protein biomarkers were used to define the region of interest (e.g., shown as region 1 and region 2). The identified regions of interest specific gene expression patterns were identified with the top 50 highly expressed genes. The data demonstrate the feasibility of multiplexing different analyte capture agents to concurrently identify the spatial gene and protein expression cluster patterns of multiplex targets in invasive ductal carcinoma tissue samples.

Figure 13:
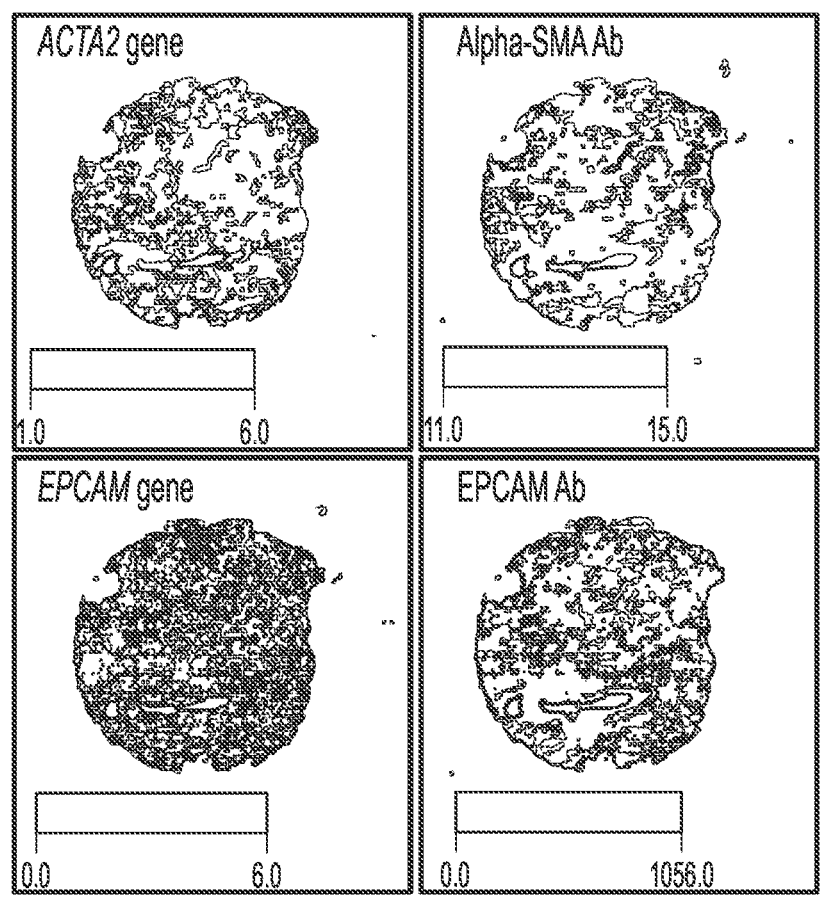
FIG. 13 shows exemplary spatial gene and protein expression in FFPE invasive ductal carcinoma tissue section superimposed on the H&E image of the ACTA2 and Epcam gene and their corresponding proteins.

FIG. 13 shows exemplary spatial gene and protein expression for Acta2 (top) and Epcam (bottom). Unbiased clustering of gene and protein expression superimposed on an H&E image of the same tissue sample demonstrate similar patterns. Plots showing the correlation between Acta2 gene expression and Alpha-SMA protein expression (encoded by the Acta2 gene) and Epcam gene expression and EPCAM protein expression (encoded by the EPCAM gene) were also generated (data not shown). A similar experiment was performed as described in FIG. 13 on a different FFPE invasive ductal carcinoma breast cancer tissue and the exemplary spatial gene and protein expression for Acta2 and separately HLA-DRA (gene) and HLA-DR (protein) correlated with one another (data not shown).

Collectively, the data demonstrate the feasibility of multiplexing different analyte capture agents to concurrently identify the spatial gene and protein expression in triple positive FFPE invasive ductal carcinoma tissue samples.

Example 4. Spatial Proteomics and Gene
Expression on FFPE Mouse Spleen, Brain, Head,
and Torso Sections in a Mouse Embryo Sample Experiments were undertaken to determine whether analyte capture agents could provide for protein expression analysis concurrently with associated gene expression in FFPE mouse tissues, including whole mouse embryos or portions thereof. The following experiments tested spatial gene and protein expression in sandwiching and non-sandwiching formats. In some examples, the alignment of a first substrate with a biological sample and a second substrate with a spatial array thereon is facilitated by a sandwiching process. Accordingly, described herein are methods of sandwiching together the first substrate with a biological sample with a second substrate comprising an array with a plurality of capture probes, where the capture probe includes a spatial barcode and a capture domain.

In a non-limiting example, FFPE mouse spleen samples, FFPE mouse samples, FFPE mouse embryo torso samples, FFPE mouse embryo head samples were placed onto standard slides (for sandwich conditions) or spatial expression (GEx) slides (as non-sandwich conditions). GEx slides include an array of spatially barcoded capture probes. Briefly, tissues were sectioned and mounted on slides and dried overnight in a desiccator. The following day, the tissues were heated to 60° C., followed by deparaffinization and rehydration. Tissues were H&E stained and bright-field imaged. Tissues were destained using HCl and decrosslinked for 1 hour in citrate buffer (pH 6.0) at 95° C. After decrosslinking, tissues were incubated overnight with whole mouse transcriptome (RNA templated ligation) probe sets at 50° C. The following day, tissues were washed to remove un-hybridized probes, then treated with ligase to ligate together the RTL probes. After another wash step, the tissues were blocked with antibody blocking buffer. Tissues were incubated overnight with a library of conjugated antibodies (e.g., a library comprising a plurality of analyte capture agents, each comprising an antigen specific antibody conjugated to an oligonucleotide). The following day, tissues were subjected to sandwiching or non-sandwich conditions as follows.

Tissues placed on standard slides for the sandwiching conditions were washed with PBS-T, subjected to an eosin stain, and washed with SSC. The tissues were subjected to sandwiching conditions. Briefly, the tissue slides were mounted in a sandwiching instrument along with a GEx slide and a reagent solution including an RNAse and Proteinase K. Upon closure in the instrument, the tissue sections were permeabilized for 30 min. allowing the ligation products and the oligonucleotides from the analyte capture agents to migrate to the GEx slide for capture by the capture probes. Following permeabilization and capture, the GEx slides were removed from the instrument.

Tissues placed on GEx slides for non-sandwiching conditions were washed with PBS-T and SSC. The tissues were subjected to a 30 min probe release step with an RNase, followed by permeabilization with a permeabilization buffer including Proteinase K. Accordingly, the ligation products and analyte capture agents were captured by the capture probes on the GEx slide.

Regardless of conditions, GEx slides were washed twice with 2xSSC, and subjected to probe extension, denaturation, and pre-amplification followed by amplification and sequencing of the templated ligation and analyte capture agent libraries.

After sequencing, the quality, sensitivity, and detection under each condition (sandwiching and non-sandwiching conditions) was evaluated. As shown in Table 1, the quality, sensitivity, and detection of globally-detected transcripts (i.e., mRNA) and proteins were comparable across the sandwich and non-sandwich conditions.

TABLE 1

| | Metric | Sandwiching Conditions | Non-Sandwiching Conditions |
| --- | --- | --- | --- |
| Templated Ligation Quality | Valid barcodes | 99.00% | 98.90% |
| | Fraction reads on target | 85.60% | 82.10% |
| | Fraction reads usable | 79.80% | 78.70% |
| | Fraction reads in spots | 81.60% | 81.00% |
| | Fraction reads unmapped | 0.90% | 1.00% |
| Templated Ligation Sensitivity | Median genes (20K prps) | 4856 | 4705 |
| | Median UMIs (20K prps) | 16966 | 15156 |
| Protein Detection using Analyte Capture Agents | Fraction reads usable | 75.20% | 67.10% |
| | Fraction reads in spot | 78.70% | 70.10% |
| | Fraction unknown | 3.70% | 3.60% |
| | Median UMIs per spot (5K reads usable per spot) | 4632 | 4114 |
| | Correlation of selected Templated Ligation/Analyte Capture Agent | 0.77 | 0.76 |

Figure 14A:
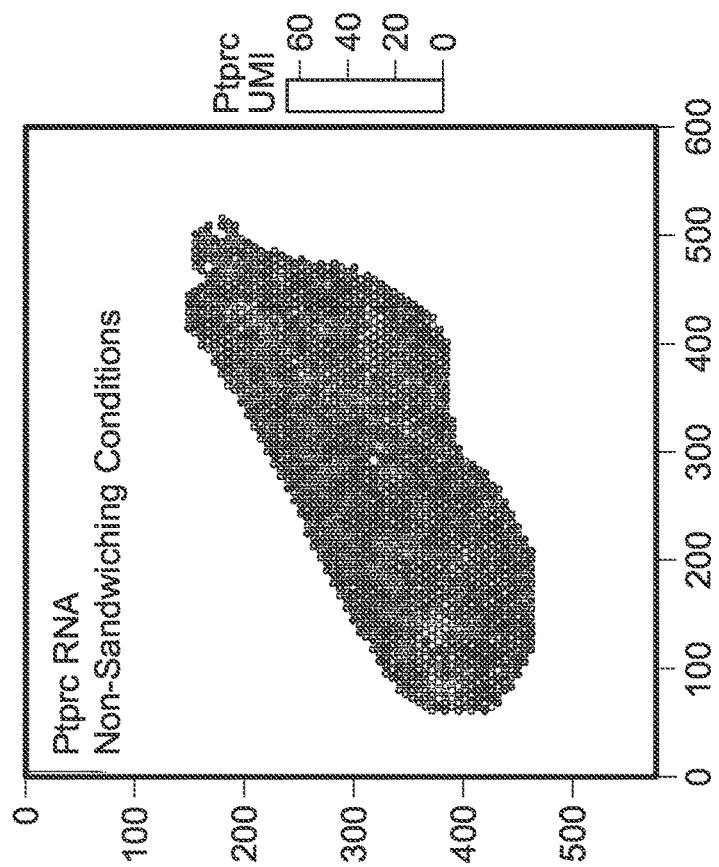
FIG. 14A shows an exemplary image of spatially-resolved information of gene expression of protein tyrosine phosphatase receptor type C (Ptprc) RNA using ligated probes in FFPE mouse spleen tissue under sandwich configuration conditions.
Figure 14B:
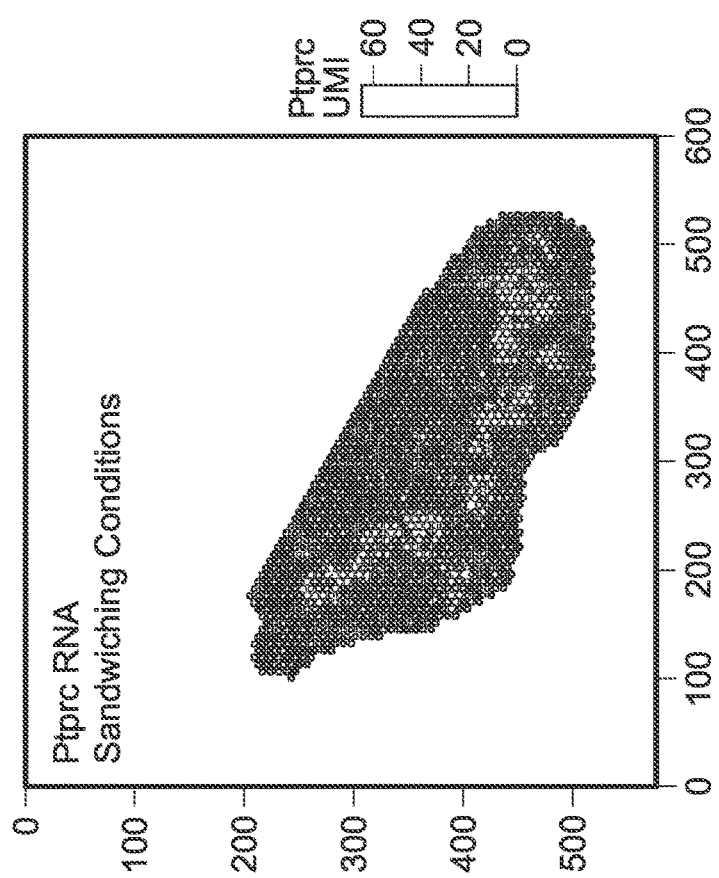
FIG. 14B shows an exemplary image of spatially-resolved information of gene expression of Ptprc RNA using ligated probes in FFPE spleen tissue under non-sandwich configuration control conditions
Figures 14C, 14D:
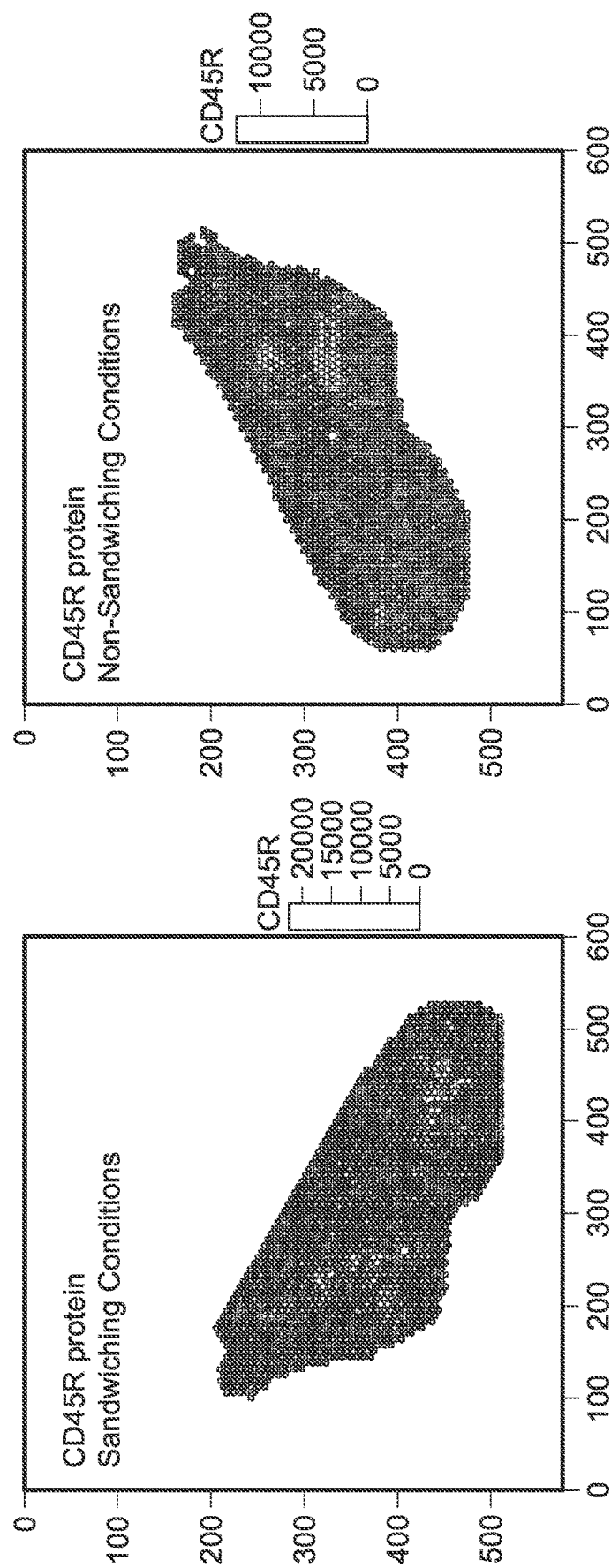
FIG. 14C shows an exemplary image of spatially-resolved information of protein expression of CD45R using analyte capture agents in FFPE mouse spleen tissue under sandwich configuration conditions.
FIG. 14D shows an exemplary image of spatially-resolved information of protein expression of CD45R using analyte capture agents in FFPE mouse spleen tissue under non-sandwich configuration control conditions.

Images were generated to evaluate the overlap of gene expression and gene protein profiles in mouse spleen tissue and mouse brain tissue for individual biomarkers. As shown in FIG. 14A (sandwiching conditions) and FIG. 14B (non-sandwiching conditions), tyrosine phosphatase receptor type C (Ptprc; e.g., Ensembl: ENSMUSG00000026395) mRNA expression was detected in a spleen tissue sample. Further, gene product (e.g., protein) CD45R was also detected both in sandwiching conditions (FIG. 14C) and in non-sandwiching conditions (FIG. 14D). CD45R is the protein name of Ptprc, and it was determined whether there was overlap of mRNA expression of Ptprc and protein expression of CD45R. As shown in FIGS. 14A-14D, both sandwiching (77% correlation) and non-sandwiching conditions (76% correlation), respectively, demonstrates overlap of transcript and protein, indicating that transcript (i.e., mRNA) and protein detection (1) was identified in similar areas of the tissues and (2) was comparable across the sandwich and non-sandwich conditions in mouse spleen samples.

The quality, sensitivity, and detection under each condition (sandwiching and non-sandwiching conditions) were evaluated globally in mouse brain samples. As shown in Table 2, the quality, sensitivity, and detection of globally-detected transcripts (i.e., mRNA) and proteins were comparable across the sandwich and non-sandwich conditions in mouse brain samples.

TABLE 2

| Metric | | Sandwiching Conditions | Non-Sandwiching Conditions |
|---|---|---|---|
| Templated Ligation Quality | Valid barcodes | 99.00% | 98.90% |
| | Fraction reads on target | 92.00% | 87.30% |
| | Fraction reads usable | 88.80% | 72.30% |
| | Fraction reads in spots | 91.80% | 79.10% |
| | Fraction reads unmapped | 1.10% | 1.90% |
| Templated Ligation Sensitivity | Median genes (10K prps) | 4405 | 3185 |
| | Median UMIs (10K prps) | 9386 | 5553 |
| Protein Detection using Analyte Capture Agents | Fraction reads usable | 80.70% | 62.30% |
| | Fraction reads in spot | 84.40% | 65.10% |
| | Fraction unknown | 3.70% | 3.70% |
| | Median UMIs per spot (5K reads usable per spot) | 3232 | 3221 |
| | Correlation of selected Templated Ligation/Analyte Capture Agent | 0.63 | 0.63 |

Figures 15A, 15B:
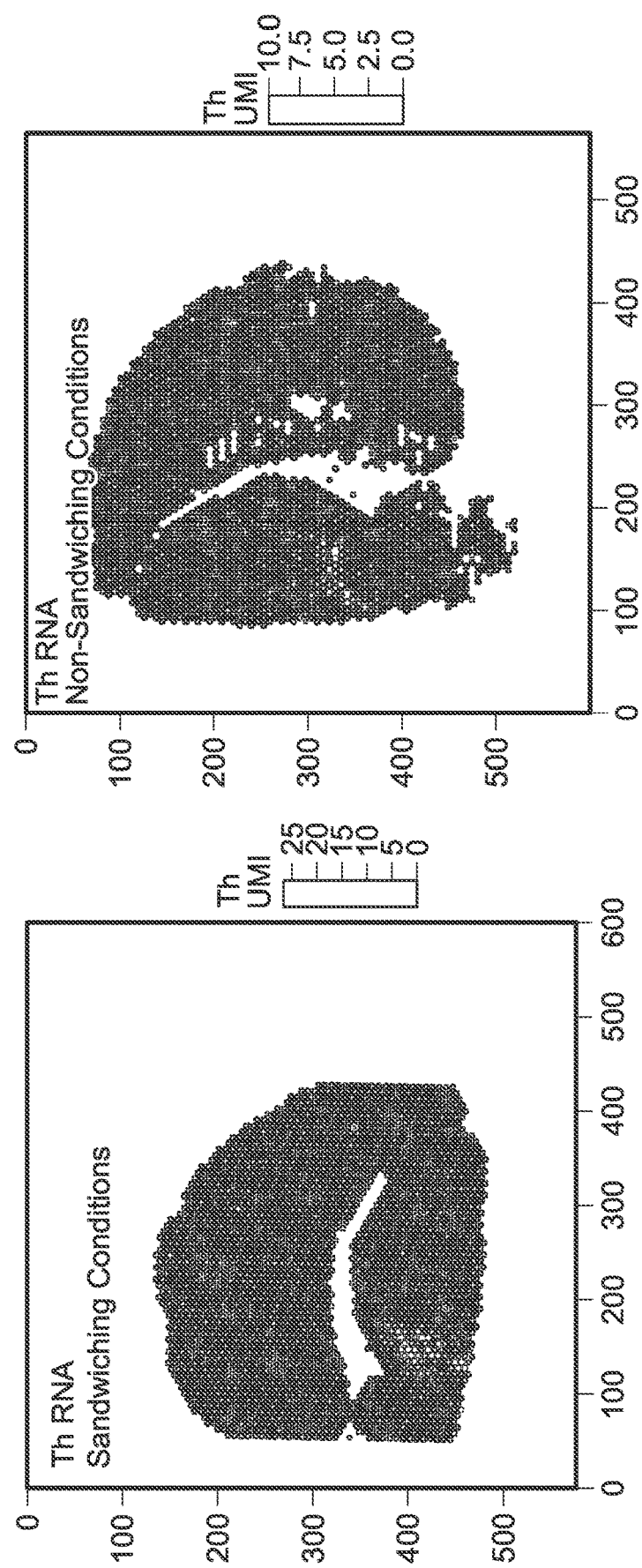
FIG. 15A shows an exemplary image of spatially-resolved information of gene expression of tyrosine hydroxylase (Th) RNA using ligated probes in FFPE mouse brain tissue under sandwich configuration conditions.
FIG. 15B shows an exemplary image of spatially-resolved information of gene expression of Th RNA using ligated probes in FFPE mouse brain tissue under non-sandwich configuration control conditions.

Similar to the mouse spleen sample images described above, individual gene expression and protein products were evaluated in mouse brain samples. As shown in FIG. 15A (sandwiching conditions) and FIG. 15B (non-sandwiching conditions), tyrosine hydroxylase (Th; e.g., Ensembl: ENSMUSG00000000214) mRNA expression was detected in brain. Further, the gene product (e.g., protein) TH was also detected in sandwiching conditions (FIG. 15C) and non-sandwiching conditions (FIG. 15D). Since TH is the protein made by Th, it was determined whether there was overlap of mRNA expression of Th and protein expression of TH. As shown in FIGS. 15A-15D, both sandwiching (63% correlation) and non-sandwiching conditions (63% correlation), respectively, saw overlap of transcript and protein, demonstrating that transcript (i.e., mRNA) and protein detection was comparable across the sandwich and non-sandwich conditions in mouse brain samples.

Experiments using the same methods (i.e., testing sandwiching conditions versus non-sandwiching conditions while detecting both RNA and protein) were performed on whole mouse embryo torso and head sections. In addition to conditions in which both RNA and protein were detected, a third condition was included as a control. This third condition (Condition 3 in Tables 3 and 4) detected the presence and abundance of only RNA. In each condition, RNA was detected using templated ligation as previously described. For Conditions 1 and 2 as shown in Tables 3 and 4 below, protein was also detected using analyte capture agent methods as previously described. The quality, sensitivity, and detection under each condition (sandwiching versus non-sandwiching conditions) were evaluated in mouse embryo torso and head samples. As shown in Tables 3 and 4, the quality, sensitivity, and detection of globally-detected transcripts (i.e., mRNA) and proteins were comparable across the sandwich and non-sandwich conditions in mouse embryo torso and head/upper torso samples. Further, the quality, sensitivity, and detection of globally-detected transcripts (i.e., mRNA) was roughly the same between Conditions 1 and 3, demonstrating that both protein capture and sandwiching methods did not interfere with RNA capture using templated ligation methods.

TABLE 3

Whole Mouse Embryo Torso Sample Data

| | Metric | Condition 1: Sandwiching Conditions Detecting both RNA and Protein | Condition 2: Non-Sandwiching Conditions Detecting both RNA and Protein | Condition 3: Non-Sandwiching Conditions Detecting RNA |
|---|---|---|---|---|
| Templated Ligation Quality | Valid barcodes | 98.9% | 99.0% | 98.5% |
| | Fraction reads on target | 88.5% | 88.5% | 87.9% |
| | Fraction reads usable | 81.5% | 77.7% | 84.8% |
| | Fraction reads in spots | 84.0% | 79.9% | 88.4% |
| | Fraction reads unmapped | 1.0% | 1.0% | 1.4% |
| Templated Ligation Sensitivity | Median genes (10K prps) | 4144 | 4356 | 3562 |
| | Median UMIs (10K prps) | 8767 | 8176 | 6121 |
| Protein Detection using Analyte Capture Agents | Fraction reads usable | 77.3% | 72.6% | — |
| | Fraction reads in spot | 80.8% | 75.9% | — |
| | Fraction unknown | 3.7% | 3.7% | — |
| | Median UMIs per spot (5K reads usable per spot) | 3358 | 3264 | — |
| | Correlation of selected Templated Ligation/Analyte Capture Agent | 0.90 | 0.80 | — |

TABLE 4

Whole Mouse Embryo Head/Upper Torso Sample Data

| | Metric | Condition 1: Sandwiching Conditions Detecting both RNA and Protein | Condition 2: Non-Sandwiching Conditions Detecting both RNA and Protein | Condition 3: Non-Sandwiching Conditions Detecting RNA |
|---|---|---|---|---|
| Templated Ligation Quality | Valid barcodes | 99.0% | 99.0% | 98.5% |
| | Fraction reads on target | 89.1% | 89.4% | 89.0% |
| | Fraction reads usable | 86.7% | 82.9% | 82.2% |
| | Fraction reads in spots | 89.5% | 85.2% | 85.2% |
| | Fraction reads unmapped | 1.0% | 1.0% | 1.5% |
| Templated Ligation Sensitivity | Median genes (10K prps) | 4400 | 4708 | 3562 |
| | Median UMIs (10K prps) | 9077 | 8431 | 6571 |
| Protein Detection using Analyte Capture Agents | Fraction reads usable | 84.3% | 77.9% | — |
| | Fraction reads in spot | 88.2% | 81.5% | — |
| | Fraction unknown | 3.7% | 3.8% | — |
| | Median UMIs per spot (5K reads usable per spot) | 3358 | 3349 | — |
| | Correlation of selected Templated Ligation/Analyte Capture Agent | 0.72 | 0.59 | — |

Figures 16A, 16B:
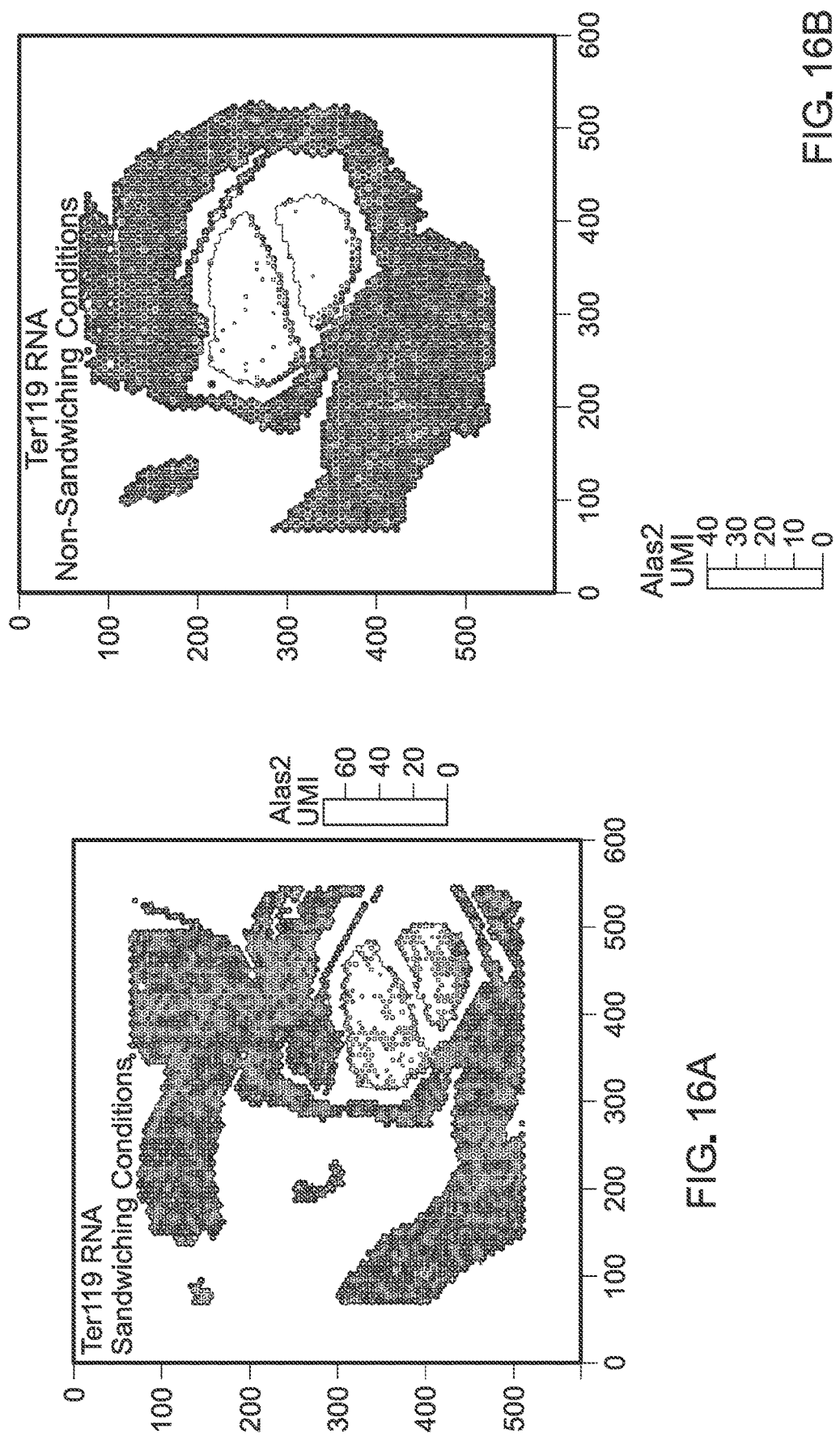
FIG. 16A shows an exemplary image of spatially-resolved information of gene expression of Ter119 RNA using ligated probes in FFPE mouse embryo torso tissue under sandwich configuration conditions.
FIG. 16B shows an exemplary image of spatially-resolved information of gene expression of Ter119 RNA using ligated probes in FFPE mouse embryo torso tissue under non-sandwich configuration conditions.
Figure 17B:
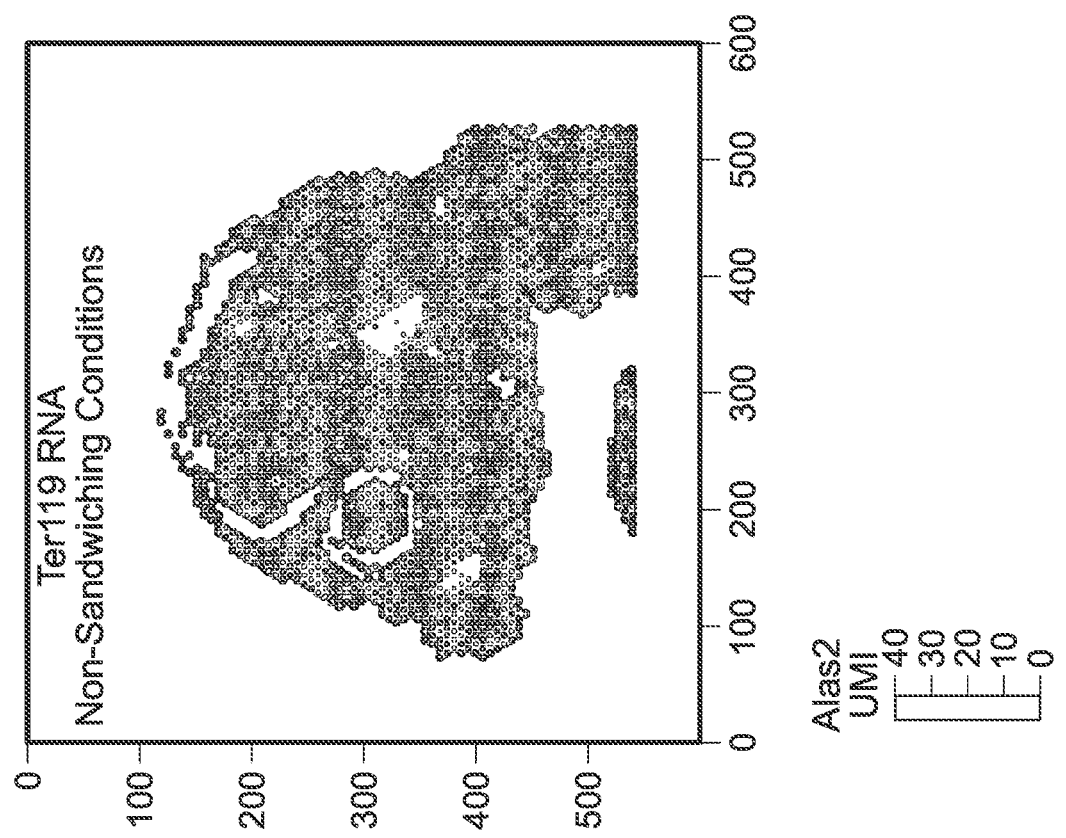
FIG. 17B shows an exemplary image of spatially-resolved information of gene expression of Ter119 RNA using ligated probes in FFPE mouse embryo head and upper torso tissue under non-sandwich configuration conditions.
Figure 17A:
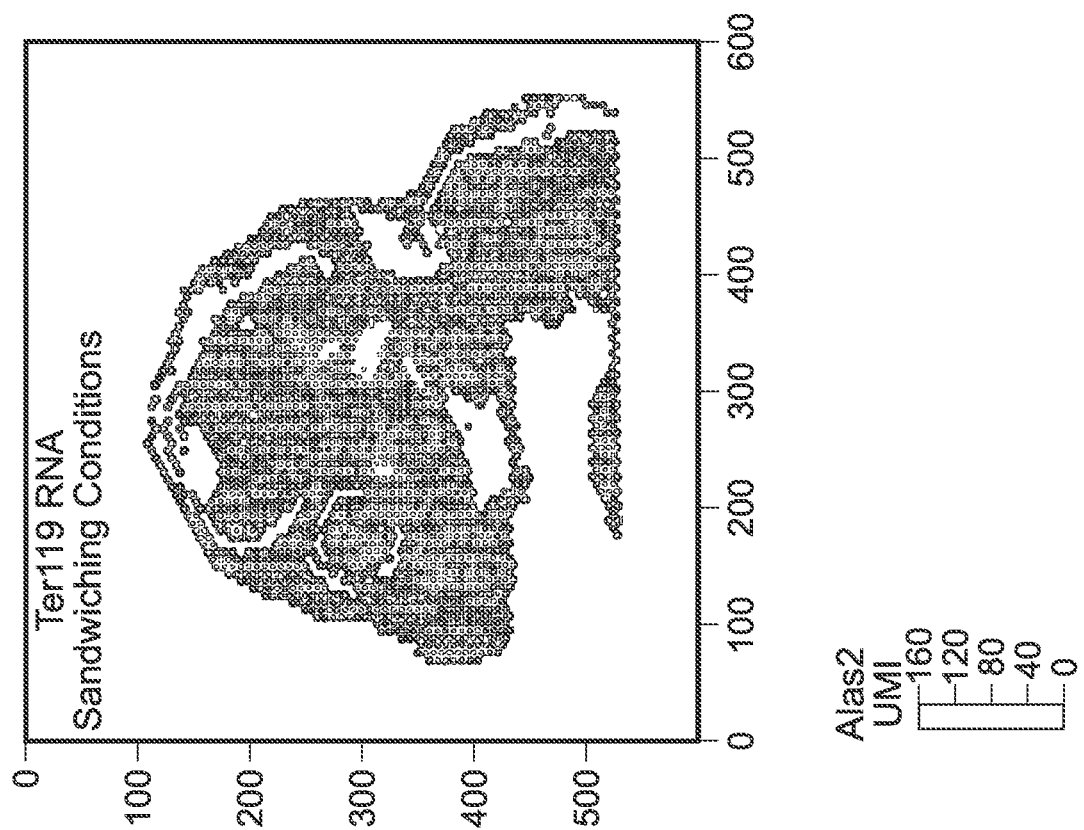
FIG. 17A shows an exemplary image of spatially-resolved information of gene expression of Ter119 RNA using ligated probes in FFPE mouse embryo head and upper torso tissue under sandwich configuration conditions.
Figure 17D:
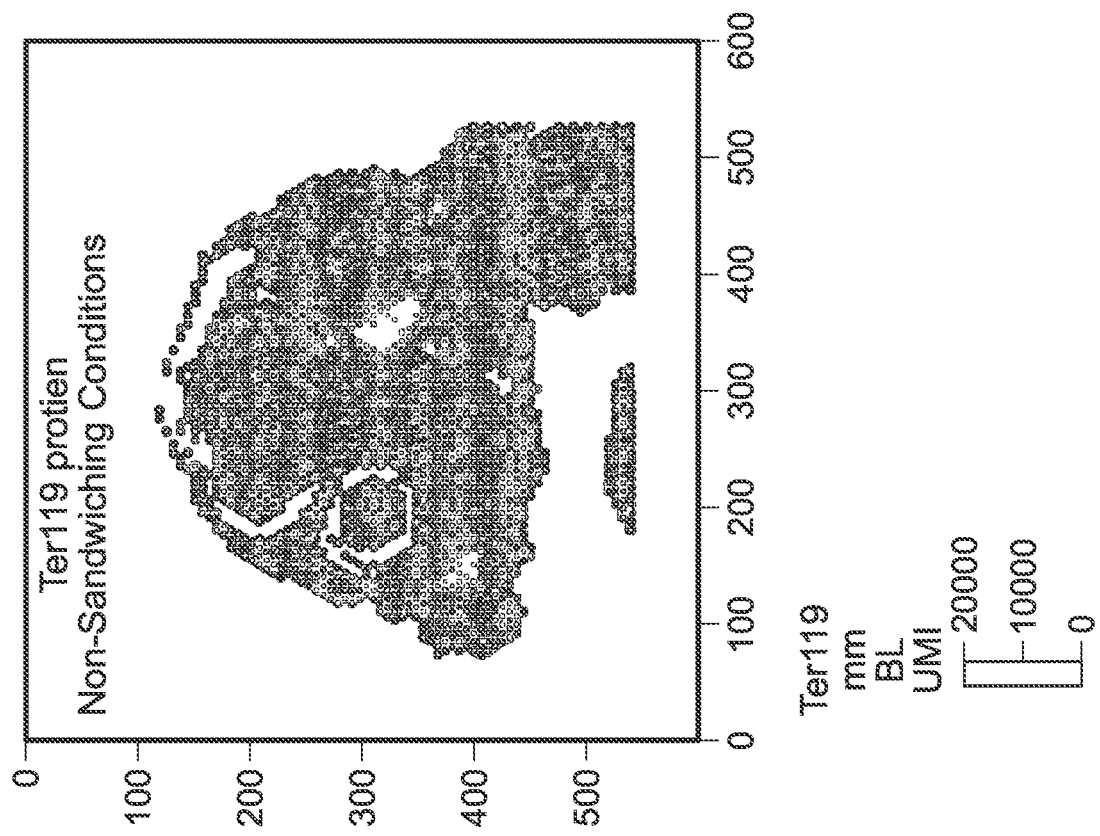
FIG. 17D shows an exemplary image of spatially-resolved information of protein expression of Ter119 using an analyte capture agent in FFPE mouse embryo head and upper torso tissue using non-sandwich configuration conditions.
Figure 17C:
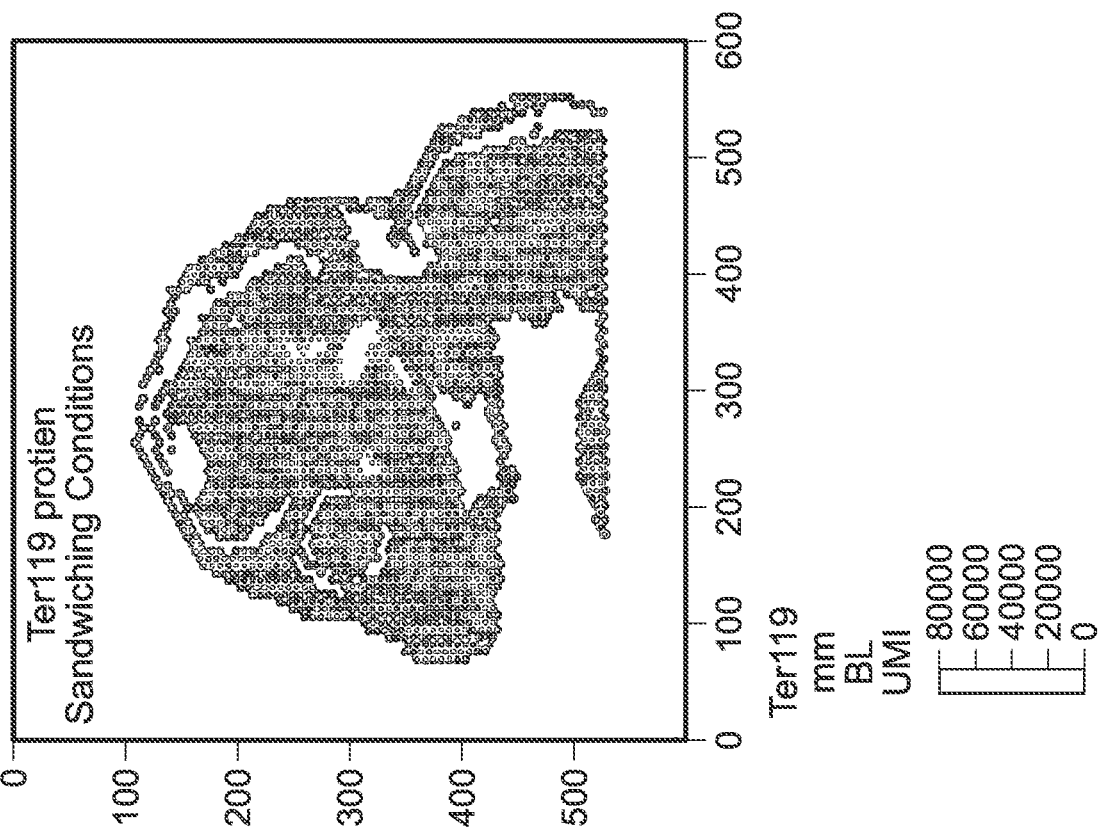
FIG. 17C shows an exemplary image of spatially-resolved information of protein expression of Ter119 using analyte capture agents in FFPE mouse embryo head and upper torso tissue under sandwich configuration conditions.
Figure 19H:
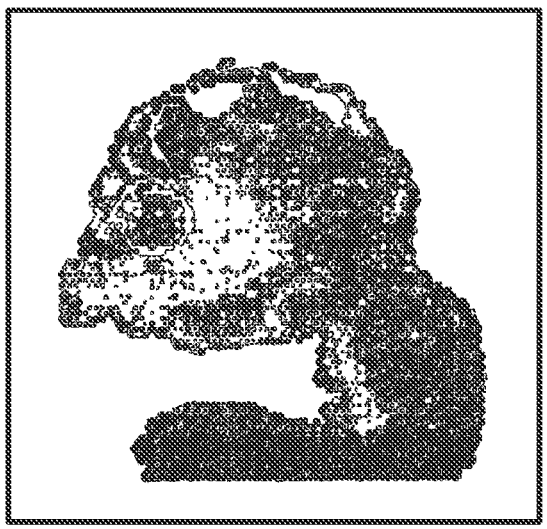
Figure 19I:
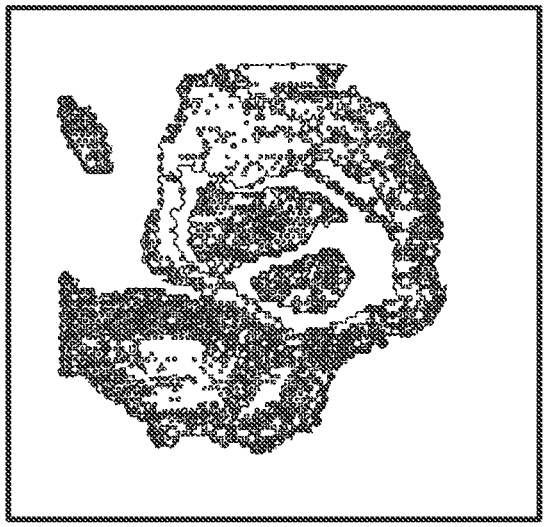
Figure 22A:
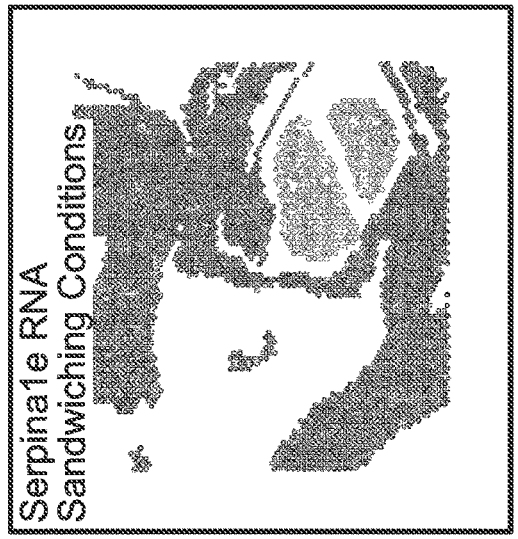
Figure 22B:
Figure 22C:
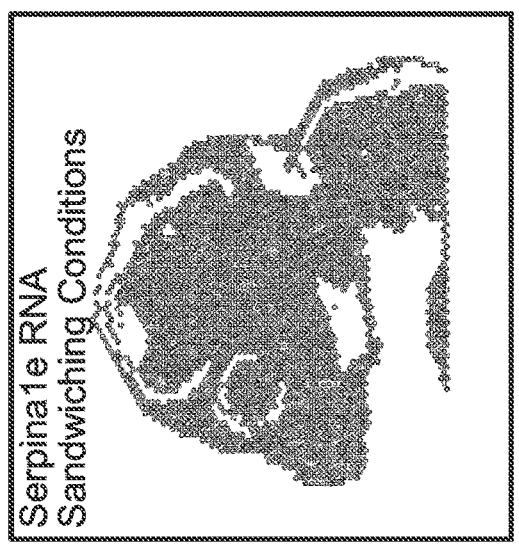
Figure 22D:
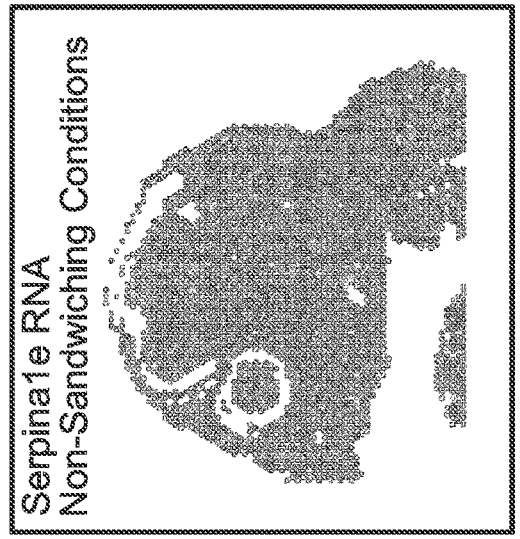
Figure 22I:
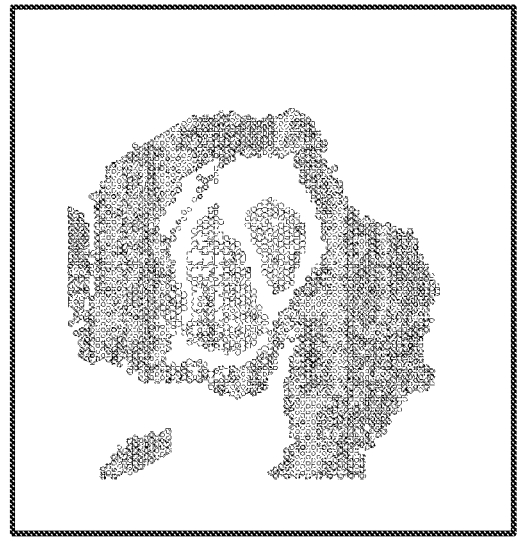
Figure 22H:
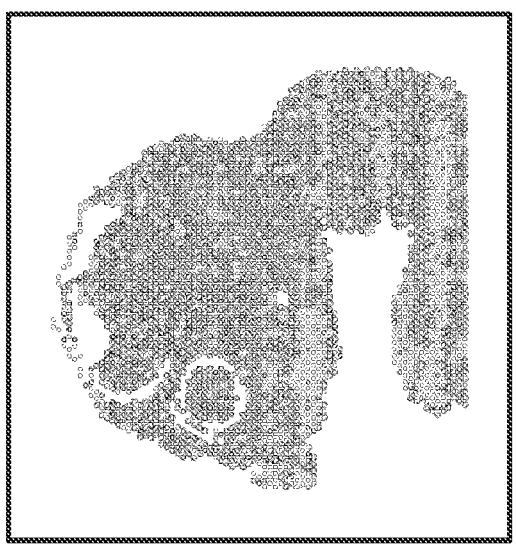

In addition to performing global expression analysis on each group, individual targets were analyzed for the location and abundance of spatial gene expression (e.g., mRNA) and spatial protein expression of single targets in the mouse embryo torso and head/upper torso samples. FIGS. 16A and 16C show mRNA (FIG. 16A) and protein (FIG. 16C) detection of lymphocyte antigen 76 (Ter119) (e.g., NCBI Gene ID: 104231), of mouse embryo torso samples in Condition 1 (i.e., in sandwiching conditions). FIGS. 16B and 16D show mRNA (FIG. 16B) and protein (FIG. 16D) detection of Ter119 of mouse embryo torso samples in Condition 2 (i.e., in non-sandwiching conditions). FIGS. 17A and 17C show mRNA (FIG. 17A) and protein (FIG. 17C) detection of Ter119 of mouse embryo head samples in Condition 1 (i.e., in sandwiching conditions). FIGS. 17B and 17D show mRNA (FIG. 17B) and protein (FIG. 17D) detection of Ter119 of mouse embryo head samples in Condition 2 (i.e., in non-sandwiching conditions). As shown in FIGS. 17A-17D, Ter119 mRNA and protein was readily detected with considerable overlap of mRNA and protein detection in both sandwiching conditions and non-sandwiching conditions, demonstrating the adaptability and reproducibility of the methods regardless of condition.

Additional single biomarkers were analyzed in the mouse embryo torso and head samples. As shown in FIGS. 18A-18I, metallophosphoesterase domain containing 1 (Mpped1; Ensembl: ENSMUSG00000041708) mRNA and protein was analyzed. Mpped1 was readily detected in the brain region of mouse embryo head samples. FIG. 18A shows detection of Mpped1 RNA in a mouse embryo head sample using sandwiching conditions (Condition 1 of Tables 3 and 4). FIG. 18E shows detection of Mpped1 protein in a mouse embryo head sample using sandwiching conditions (Condition 1 of Tables 3 and 4). However, Mpped1 RNA was not readily detected in a mouse embryo torso sample (FIG. 18B). Consistent with these observations, Mpped1 has metallophosphoesterase activity, which could have a role in brain development, as such was expected to be present in the embryo head sample and not in the embryo torso sample. Consistent with the sandwiching conditions data, Mpped1 mRNA and protein was detected in non-sandwiching conditions in the head (FIG. 18C (mRNA) and FIG. 18F (protein)) but not in the torso (FIG. 18D (mRNA) and FIG. 18G (protein)). Similarly, in non-sandwiching conditions in which only RNA was detected, Mpped1 RNA was detected in the head (FIG. 18H) but not in the torso (FIG. 18I). As such, regardless of conditions, both gene and protein expression, down to the single biomarker level, can be detected concurrently in the same sample.

Four additional biomarkers—troponin C1, slow skeletal and cardiac type (Tnnc1; e.g., Ensembl: ENSMUSG00000091898); fibroblast growth factor 15 (Fgf15; e.g., Ensembl: ENSMUSG00000031073); epiphycan (Epyc e.g., Ensembl: ENSMUSG00000019936); and serine (or cysteine) peptidase inhibitor, Glade A, member 1E (Serpina1e; e.g., Ensembl: ENSMUSG00000072849) were examined in head/upper torso and torso mouse embryo samples under Conditions 1, 2, and 3 from Tables 3 and 4. See FIGS. 19A-22I. Tnnc1 is involved in muscle contraction regulation and its expression was readily detected in all samples under each Condition. See FIGS. 19A-19I. Fgf15 functions in retinal neurogenesis and as a cell fate determination factor. Indeed, its expression was found in the eye of the embryo in each head sample, but was not detected in the torso. See FIGS. 20A-20I. Epyc functions in bone formation and in cartilage structure and was detected in each sample (head and torso). See FIGS. 21A-21I. Finally, Serpina1e is active in the liver as it functions in alpha-1 antitrypsin protein production. As shown in FIGS. 22A-22I, Serpina1e was detected in the torso of mouse embryos but was not detected in the head/upper torso samples. Consistent among each of these biomarker images, the non-sandwiching methods readily detected individual mRNA and protein biomarkers compared to sandwiching methods.

As such, using sandwiching or non-sandwiching conditions, both gene and protein expression, down to the single biomarker level, can be detected concurrently across multiple tissue types using the methods described herein.

Example 5. Spatial Proteomics, Spatial Gene Expression, and Immune Cell Identification in FFPE Cancer Tissue Sections Experiments were undertaken to determine whether analyte capture agents could provide for spatial protein and gene expression analysis in FFPE cancer tissue sections. Additionally, experiments were undertaken to identify various types of immune cells in breast cancer FFPE tissue sections and ovarian cancer FFPE tissue sections. The tissue sections were prepared and analysis was performed by the methods described in Example 4.

Invasive Ductal Carcinoma Breast Cancer

Figure 23A:
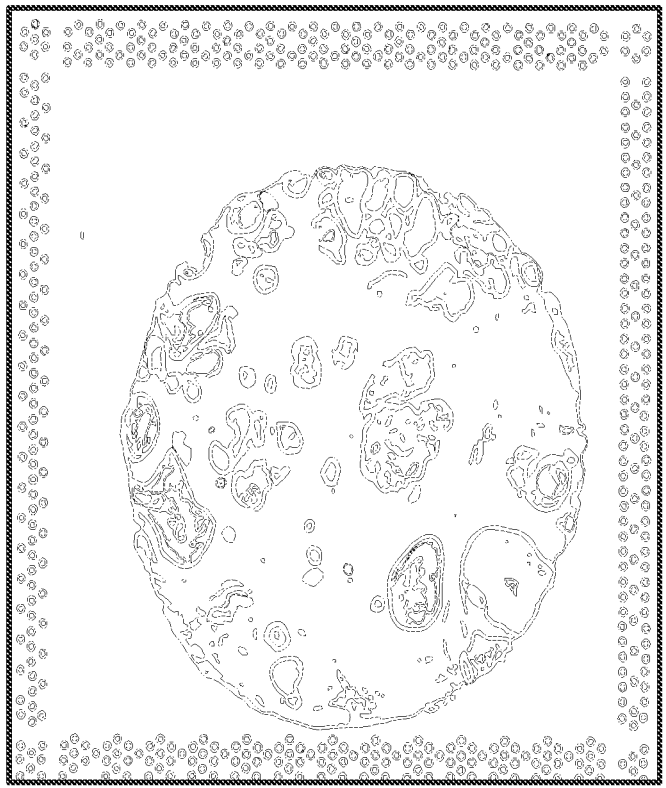
Figure 23B:
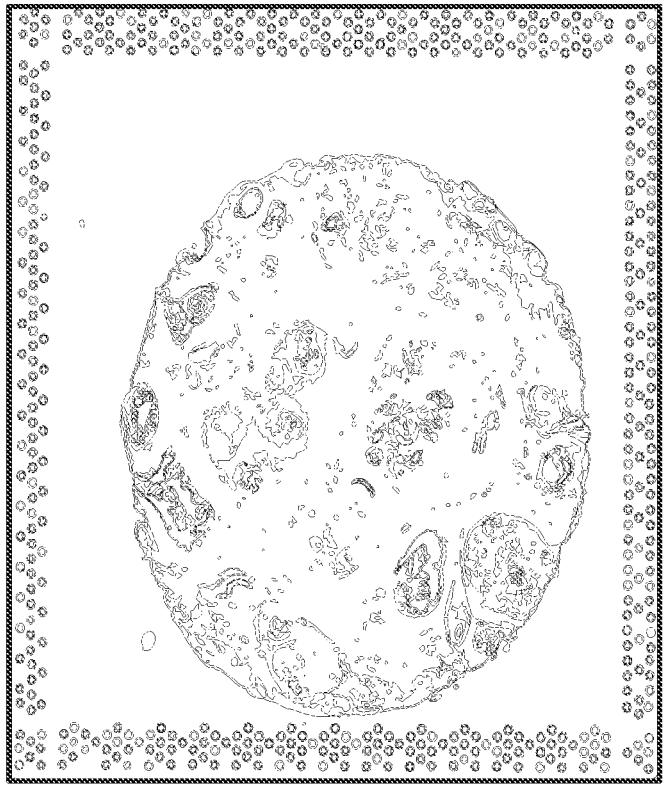

As shown in FIGS. 23A-E a 25-plex antibody panel was used to study the tumor microenvironment and show spatial immune cell infiltration in a breast cancer FFPE tissue section. The data shown in FIGS. 23A-E are from cored samples from larger tissue sections which demonstrated consistent spatial gene and spatial protein expression as shown in FIGS. 23C-E and described herein (data not shown). FIG. 23A shows an H&E stained human invasive ductal carcinoma grade III breast cancer FFPE tissue section and FIG. 23B shows the H&E image of FIG. 23A annotated by a pathologist. The pathologist annotations are outlined in the image and correspond to either Blood Vessel, DCIS (ductal carcinoma in situ), Immune Cells, Invasive Carcinoma, Necrosis, or Normal Gland. The pathologist identified ductal carcinoma in situ as well as areas of tissue with immune cell infiltrates.

The spatial gene and spatial protein expression clustering superimposed on the H&E stained image shown in FIG. 23A demonstrated similar expression patterns delineating the tumor and stromal region (data not shown). More specifically, protein immune markers were used to identify infiltrating immune cells. For example, FIG. 23C shows spatial protein expression of CD3 (e.g., a marker for T cells) and FIG. 23D shows spatial protein expression of CD8A (e.g., a marker for cytotoxic T cells). Moreover, within an infiltrate, spatial orientation of different types of immune cells were distinguishable. An example of this is shown in FIG. 23E where an accumulation of cytotoxic T cells expressing human leukocyte antigen-DR isotype (HLA-DR) (e.g., a marker of T cell activation) were observed.

Additionally, spatial gene and protein expression of additional genes and proteins were examined from the same tissue section shown in FIG. 23A. More specifically, gene ACTA2 and its corresponding protein, alpha-smooth muscle actin (SMA), demonstrated similar expression patterns with positive gene-protein UMI count correlations (data not shown). Further examination of cytokeratin gene, KRT18, also demonstrated similar patterns to a PanCK antibody and again positive gene-protein UMI correlations were observed (data not shown).

In a different grade II invasive ductal carcinoma FFPE breast cancer tissue section the tissue section was H&E stained and spatial protein expression of PanCK and HLA-DR within the tissue section. Manual selection of the HLA- DR and PanCK positive regions was performed with the 10× Loupe Browser showing contrasting regions within the tissue section. Local differential expression analysis of both regions generated the top 50 genes associated with expression in the HLA-DR or PanCK selected regions identified and are shown in Table 5.

tation for invasive carcinoma and immune cells in an H&E stained ovarian cancer FFPE tissue section. The pathologist annotations are outlined in the image and correspond to either Blood Vessel, DCIS (ductal carcinoma in situ), Immune Cells, Invasive Carcinoma, or Necrosis.

TABLE 5

| Marker ID | Marker Name | HLA-DR Average | HLA-DR Log2 Fold Change | HLA-DR P-Value | PanCK Average | PanCK Log2 Fold Change | PanCK P-Value |
|---|---|---|---|---|---|---|---|
| ENSG00000106483 | SFRP4 | 11.59067363 | 2.58736286 | 3.34E−49 | 1.926061057 | −2.58736286 | 3.34E−49 |
| ENSG00000168685 | IL7R | 3.519297315 | 2.433061874 | 1.02E−40 | 0.650696303 | −2.433061874 | 1.02E−40 |
| ENSG00000011465 | DCN | 29.40019273 | 2.218895222 | 4.74E−39 | 6.307770284 | −2.218895222 | 4.74E−39 |
| ENSG00000091986 | CCDC80 | 3.432380045 | 2.310230989 | 7.36E−39 | 0.691066033 | −2.310230989 | 7.36E−39 |
| ENSG00000139329 | LUM | 33.17683334 | 2.178290672 | 9.94E−38 | 7.321262975 | −2.178290672 | 9.94E−38 |
| ENSG00000197614 | MFAP5 | 3.117091908 | 2.247513206 | 2.12E−36 | 0.655476929 | −2.247513206 | 2.12E−36 |
| ENSG00000211772 | TRBC2 | 4.483908589 | 2.20449644 | 3.84E−36 | 0.971529419 | −2.20449644 | 3.84E−36 |
| ENSG00000087245 | MMP2 | 9.819947279 | 2.17666454 | 3.84E−36 | 2.169341797 | −2.17666454 | 3.84E−36 |
| ENSG00000182326 | C1S | 7.999797384 | 2.155136429 | 4.02E−36 | 1.793797074 | −2.155136429 | 4.02E−36 |
| ENSG00000108821 | COL1A1 | 150.9804112 | 2.114722952 | 4.02E−36 | 34.81889197 | −2.114722952 | 4.02E−36 |
| ENSG00000136235 | GPNMB | 5.620650143 | 2.161589748 | 2.39E−34 | 1.254648708 | −2.161589748 | 2.39E−34 |
| ENSG00000090382 | LYZ | 5.075286879 | 2.204681169 | 3.37E−34 | 1.099543957 | −2.204681169 | 3.37E−34 |
| ENSG00000064205 | CCN5 | 3.718695759 | 2.138373605 | 4.86E−34 | 0.843514881 | −2.138373605 | 4.86E−34 |
| ENSG00000211751 | TRBC1 | 4.436189304 | 2.185129984 | 7.54E−34 | 0.974185322 | −2.185129984 | 7.54E−34 |
| ENSG00000164692 | COL1A2 | 97.7921546 | 2.041795601 | 8.18E−34 | 23.72199689 | −2.041795601 | 8.18E−34 |
| ENSG00000277734 | TRAC | 4.685011293 | 2.099070424 | 4.58E−33 | 1.092107428 | −2.099070424 | 4.58E−33 |
| ENSG00000211592 | IGKC | 190.0999999 | 2.203176006 | 9.62E−33 | 41.23342956 | −2.203176006 | 9.62E−33 |
| ENSG00000271503 | CCL5 | 4.115788386 | 2.085695324 | 1.34E−32 | 0.968342335 | −2.085695324 | 1.34E−32 |
| ENSG00000158747 | NBL1 | 8.572428812 | 2.007423552 | 1.09E−31 | 2.129503248 | −2.007423552 | 1.09E−31 |
| ENSG00000106624 | AEBP1 | 24.52600855 | 1.986108768 | 1.64E−31 | 6.183474011 | −1.986108768 | 1.64E−31 |
| ENSG00000169442 | CD52 | 2.54616474 | 2.103282373 | 1.85E−31 | 0.59173525 | −2.103282373 | 1.85E−31 |
| ENSG00000168542 | COL3A1 | 55.19587513 | 1.945997239 | 8.85E−31 | 14.30841332 | −1.945997239 | 8.85E−31 |
| ENSG00000163520 | FBLN2 | 4.983256828 | 1.994115903 | 8.85E−31 | 1.249336902 | −1.994115903 | 8.85E−31 |
| ENSG00000172724 | CCL19 | 4.214635477 | 2.569106092 | 1.13E−30 | 0.709126175 | −2.569106092 | 1.13E−30 |
| ENSG00000145423 | SFRP2 | 12.30135013 | 1.975672819 | 1.40E−30 | 3.123873435 | −1.975672819 | 1.40E−30 |
| ENSG00000140937 | CDH11 | 6.69433407 | 1.973568341 | 1.57E−30 | 1.702434001 | −1.973568341 | 1.57E−30 |
| ENSG00000106565 | TMEM176B | 2.784761169 | 2.020982234 | 4.69E−30 | 0.685223046 | −2.020982234 | 4.69E−30 |
| ENSG00000172061 | LRRC15 | 6.252930678 | 1.96380266 | 5.20E−30 | 1.600978496 | −1.96380266 | 5.20E−30 |
| ENSG00000166741 | NNMT | 3.541452698 | 1.979047111 | 1.90E−29 | 0.897164127 | −1.979047111 | 1.90E−29 |
| ENSG00000184347 | SLIT3 | 2.425162266 | 2.012530816 | 3.18E−29 | 0.600234141 | −2.012530816 | 3.18E−29 |
| ENSG00000107562 | CXCL12 | 6.52390805 | 1.925167509 | 5.56E−29 | 1.715713517 | −1.925167509 | 5.56E−29 |
| ENSG00000149131 | SERPING1 | 7.503857666 | 1.912104472 | 5.56E−29 | 1.991396278 | −1.912104472 | 5.56E−29 |
| ENSG00000123500 | COL10A1 | 6.305762744 | 1.924239545 | 7.60E−29 | 1.659408368 | −1.924239545 | 7.60E−29 |
| ENSG00000140285 | FGF7 | 1.174235279 | 2.165189314 | 8.22E−29 | 0.261340883 | −2.165189314 | 8.22E−29 |
| ENSG00000115594 | IL1R1 | 2.104761348 | 2.001816916 | 1.23E−28 | 0.524806488 | −2.001816916 | 1.23E−28 |
| ENSG00000159403 | C1R | 10.59027289 | 1.895587338 | 2.40E−28 | 2.842878868 | −1.895587338 | 2.40E−28 |
| ENSG00000165507 | DEPP1 | 5.92741698 | 2.006365507 | 2.68E−28 | 1.473495138 | −2.006365507 | 2.68E−28 |
| ENSG00000142871 | CCN1 | 11.35378146 | 1.8940456 | 3.90E−28 | 3.051101685 | −1.8940456 | 3.90E−28 |
| ENSG00000143196 | DPT | 2.212129741 | 1.984447325 | 3.90E−28 | 0.558270869 | −1.984447325 | 3.90E−28 |
| ENSG00000213886 | UBD | 1.508270278 | 2.211600224 | 3.90E−28 | 0.325082561 | −2.211600224 | 3.90E−28 |
| ENSG00000186340 | THBS2 | 6.307467004 | 1.90036637 | 3.90E−28 | 1.687560943 | −1.90036637 | 3.90E−28 |
| ENSG00000060718 | COL11A1 | 5.138344506 | 1.953199093 | 1.11E−27 | 1.325295736 | −1.953199093 | 1.11E−27 |
| ENSG00000197747 | S100A10 | 6.643206264 | 1.86886665 | 1.72E−27 | 1.816307842 | −1.86886665 | 1.72E−27 |
| ENSG00000132386 | SERPINF1 | 11.63498439 | 1.853278452 | 1.80E−27 | 3.216298869 | −1.853278452 | 1.80E−27 |
| ENSG00000118523 | CCN2 | 16.70174997 | 1.860743031 | 3.07E−27 | 4.593119128 | −1.860743031 | 3.07E−27 |
| ENSG00000127083 | OMD | 1.624159972 | 2.000597227 | 4.93E−27 | 0.40529084 | −2.000597227 | 4.93E−27 |
| ENSG00000084636 | COL16A1 | 3.253432724 | 1.891287213 | 6.63E−27 | 0.875916901 | −1.891287213 | 6.63E−27 |
| ENSG00000180447 | GAS1 | 2.45413469 | 1.901572191 | 2.20E−26 | 0.65600811 | −1.901572191 | 2.20E−26 |
| ENSG00000163430 | FSTL1 | 10.87829286 | 1.80177238 | 6.32E−26 | 3.116436906 | −1.80177238 | 6.32E−26 |
| ENSG00000227507 | LTB | 2.731929102 | 1.888847173 | 8.98E−26 | 0.736747569 | −1.888847173 | 8.98E−26 |

The data demonstrate that spatial protein expression can identify immune cell infiltration in breast cancer FFPE tissue sections and moreover the spatial protein expression correlates with annotations by a pathologist which demonstrates the utility of the methods described herein in identifying immune cells within a tumor microenvironment can be used as a diagnostic tool.

Ovarian Carcinoma

Figure 24A:
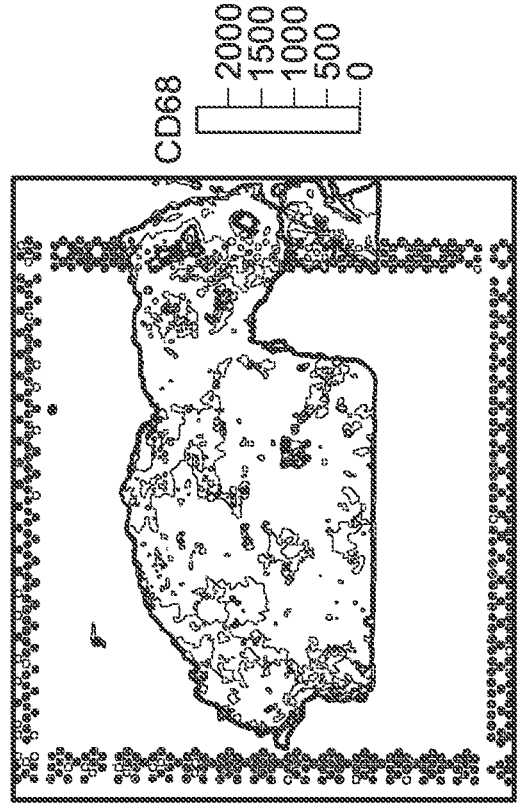
FIGS. 24A-D show spatial immune cell infiltration in an ovarian cancer FFPE tissue section correlates with pathologist annotations.
Figure 24B:
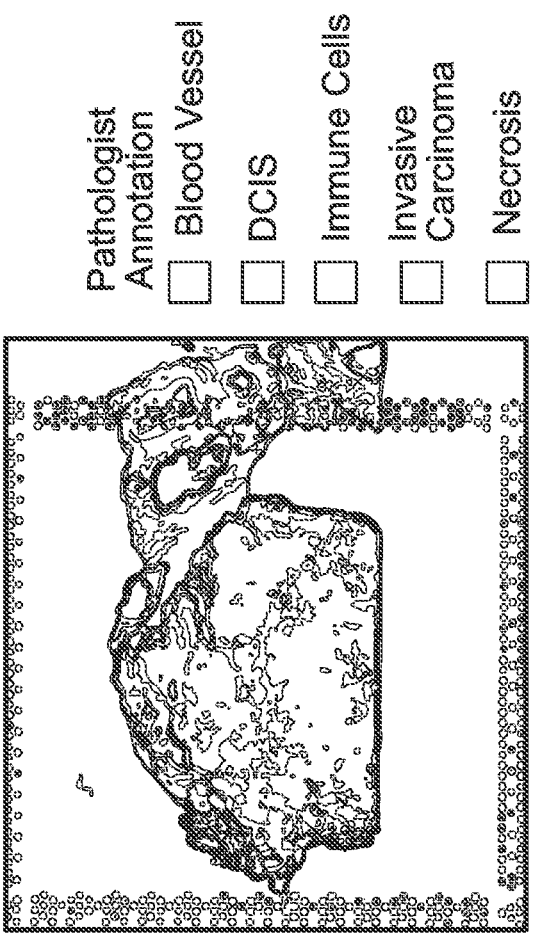
Figure 24C:
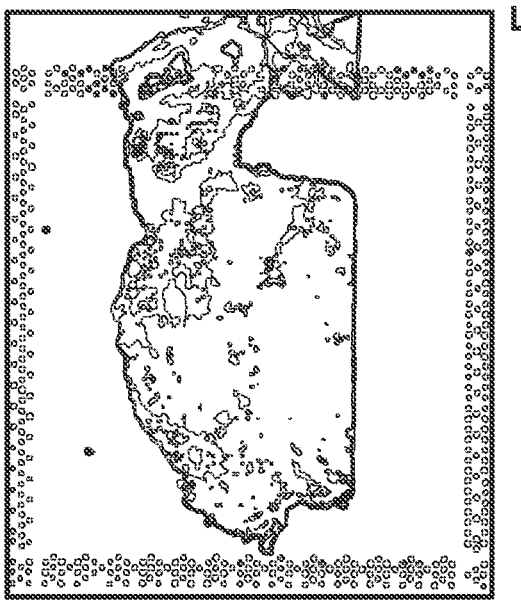
Figure 24D:
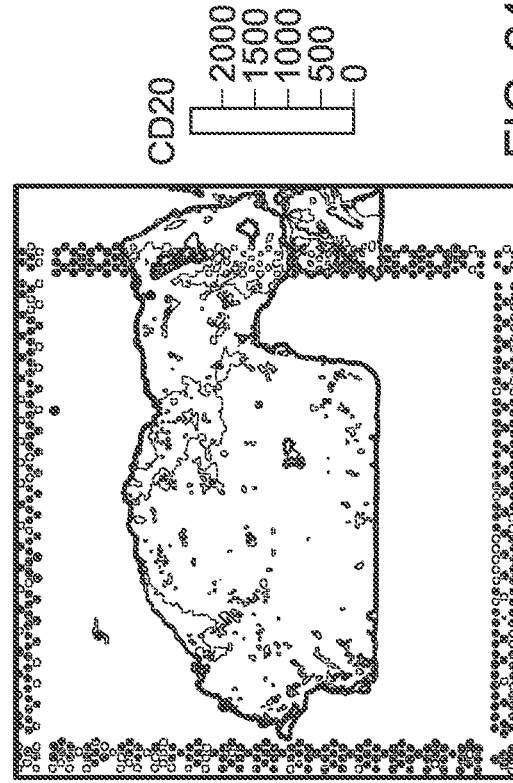

As shown in FIGS. 24A-D a 25-plex antibody panel was used to study an FFPE ovarian cancer (e.g., carcinoma) tissue section and show spatial immune cell infiltration. The antibody panel included antibodies for both intracellular and extracellular markers. FIG. 24A shows a pathologist's anno- The 25-plex antibody panel included antibodies for protein immune markers which confirmed the presence of immune cells within the ovarian cancer FFPE tissue section. Further, the antibody panel distinguished (e.g., subtyped) the immune cells based on their characteristic surface markers. For example, FIG. 24B shows spatial protein expression of CD20 (e.g., a marker for B cells) and FIG. 24C shows spatial protein expression of CD68 (e.g., a marker for monocytes). FIG. 24D shows spatial protein expression of CD8A (e.g., a marker for cytotoxic T cells) and a small region of the ovarian carcinoma includes cytotoxic T cell infiltration (arrow) while the larger carcinoma does not.

Figure 25A:
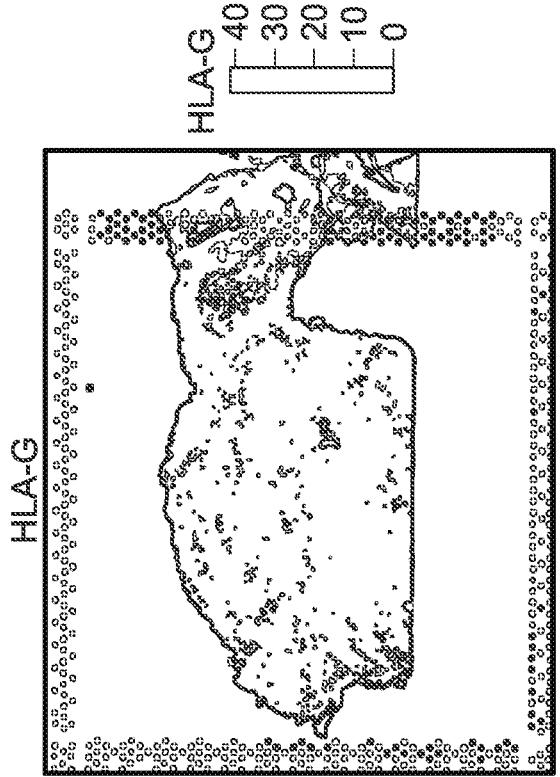
FIGS. 25A-D show differential spatial cytotoxic T cell infiltration within different regions of an ovarian cancer FFPE tissue section.
Figure 25C:
Figure 25B:
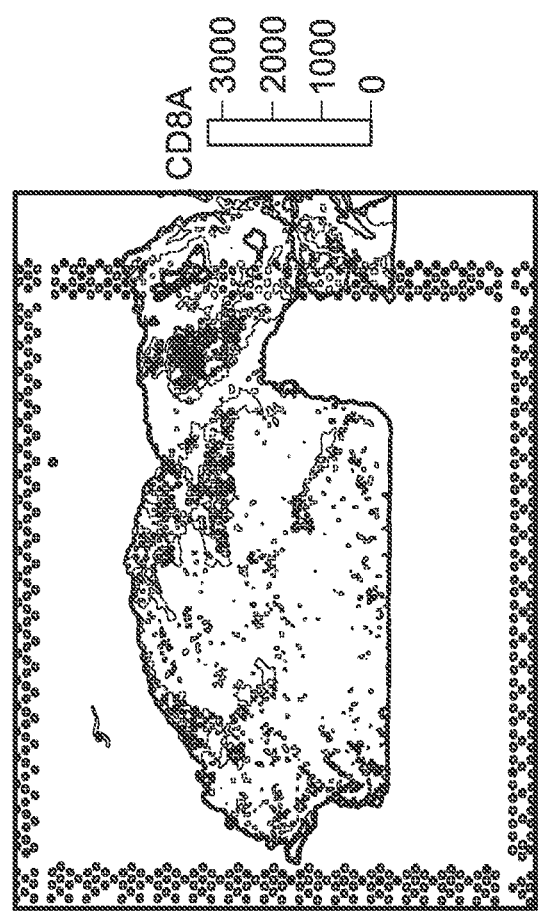
Figure 25D:
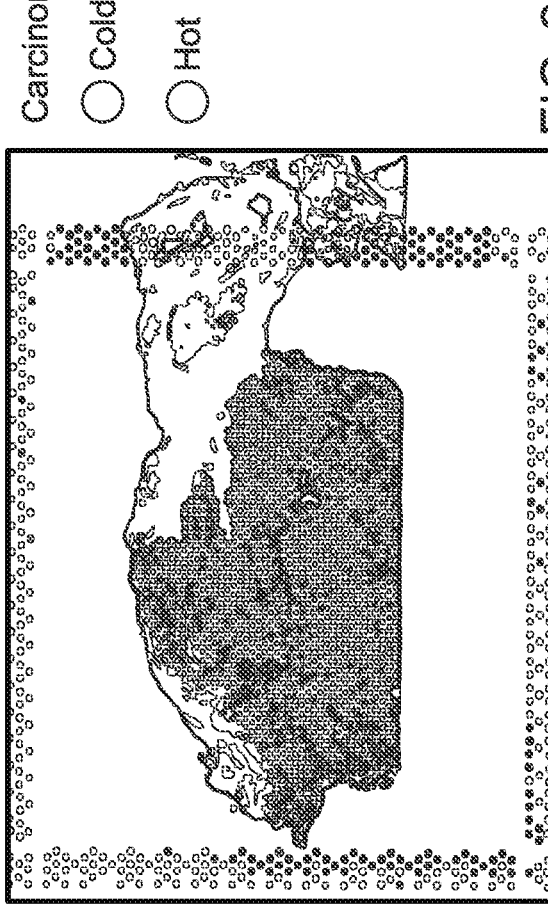

FIGS. 25A-D show differential spatial cytotoxic T cell infiltration within different regions of an ovarian cancer FFPE tissue section. Gene expression profiles of the large and small carcinoma regions were compared to find differences that may be correlated to varying immune cell infiltration observed in the protein expression data. FIG. 25A shows spatial protein expression of CD8A (e.g., a marker for cytotoxic T cells) and FIG. 25B shows highly infiltrated ("hot") and non-infiltrated ("cold") areas of the ovarian cancer FFPE tissue section. The infiltration mapping is based on protein detection of CD3 protein expression for the "hot" or high cytotoxic T cell infiltration, and CD8 protein expression for the "cold" or minimal to no cytotoxic T cell infiltration. FIGS. 25C and 25D show spatial gene expression of immune response genes. For example, FIG. 25C shows spatial gene expression of HLA class I histocompatibility antigen, alpha chain G (HLA-G; also known as human leukocyte antigen G) in the small carcinoma which correlates with protein expression data and FIG. 25D shows spatial gene expression in the large carcinoma of interphotoreceptor matrix proteoglycan 2 (IMPG2), which is known to be involved in tumor growth, which also correlates with protein expression data. The data demonstrate that spatial protein expression can identify immune cell infiltration in ovarian cancer FFPE tissues sections and moreover the spatial protein expression correlates with annotations by a pathologist and with gene expression data which demonstrates the utility of the methods described herein in identifying immune cells within a tumor microenvironment. The methods described herein can also be used as a diagnostic tool and/or screening method. Additionally, spatial gene expression correlating to different ovarian carcinomas within a tissue section are distinguishable by the methods described herein.

Example 6. Spatial Proteomics and Spatial Gene Expression in FFPE Cancer Tissue Sections Experiments were undertaken to determine whether analyte capture agents could provide for spatial protein and gene expression analysis in FFPE cancer tissue sections. The tissue sections were prepared and analysis was performed by the methods described in Example 4.

Lung Cancer

Figure 27A:
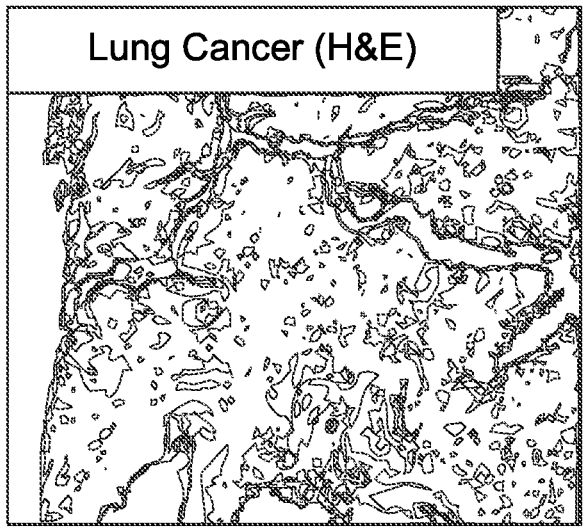
FIGS. 27A-D show exemplary spatial gene (FIG. 27B) and protein expression (FIG. 27C) expression in lung cancer FFPE tissue.
Figure 27B:
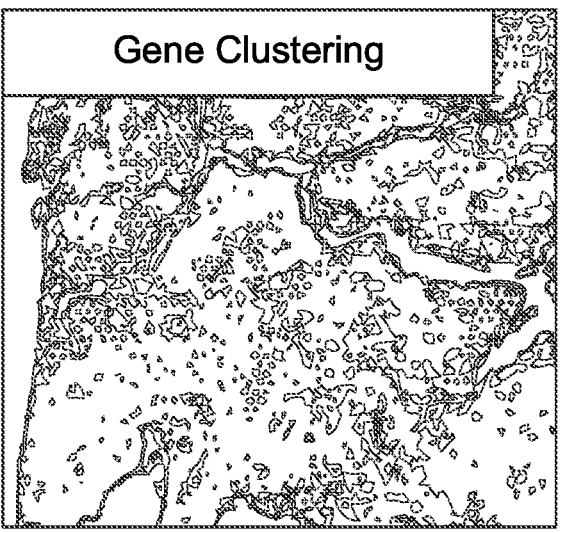
Figure 27C:
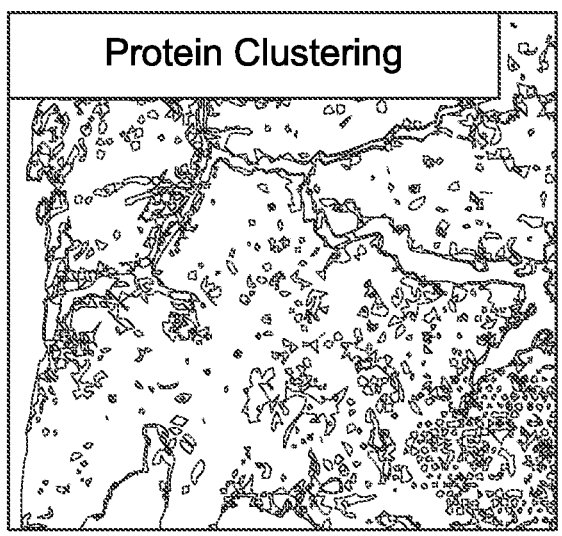
Figure 27D:
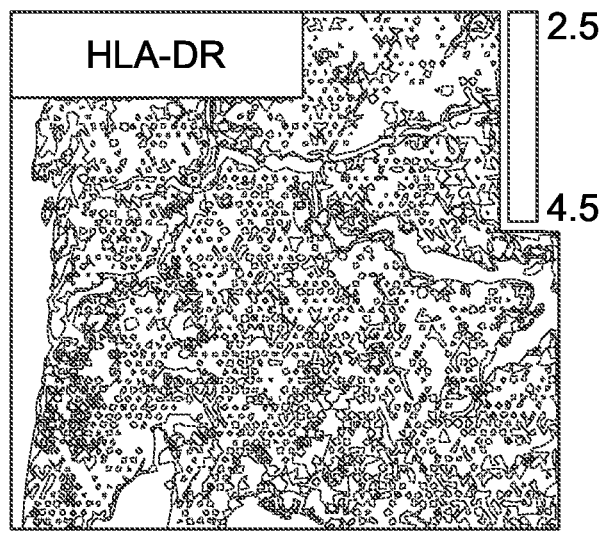

As shown in FIGS. 27A-D spatial gene and spatial protein expression analysis in a FFPE lung cancer tissue section. FIG. 27A shows an H&E stained lung cancer FFPE tissue section and FIGS. 27B and 27C, show spatial gene expression clustering (FIG. 27B) and spatial protein expression clustering (FIG. 27C), respectively. FIG. 27D shows a HLA-DR protein spatial UMI plot. As described herein, HLA-DR is a marker of T cell activation and FIG. 27D The data demonstrate that spatial gene and spatial protein expression correlate with each other which demonstrates the utility of the methods described herein in identifying spatial gene and protein expression in lung cancer FFPE tissue sections which can be used as a diagnostic tool.

Melanoma

Figure 28A:
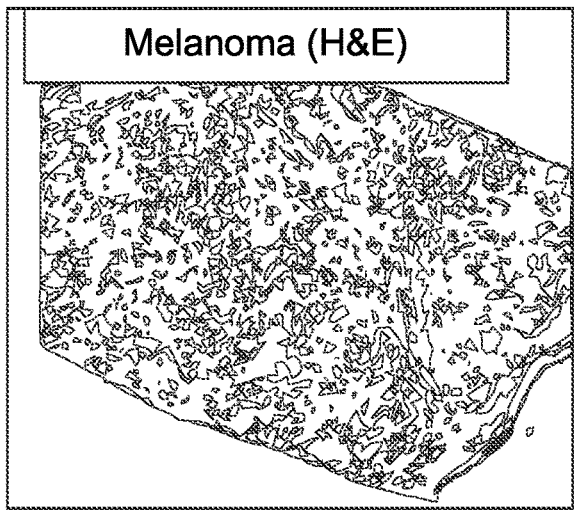
FIGS. 28A-D show exemplary spatial gene (FIG. 28B) and protein expression (FIG. 28C) expression in melanoma FFPE tissue.
Figure 28B:
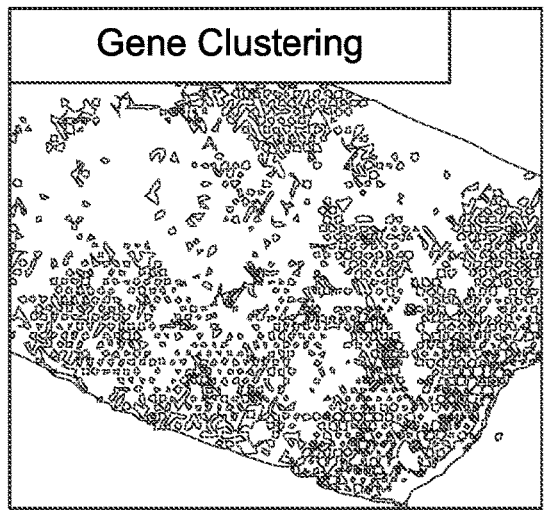
Figure 28C:
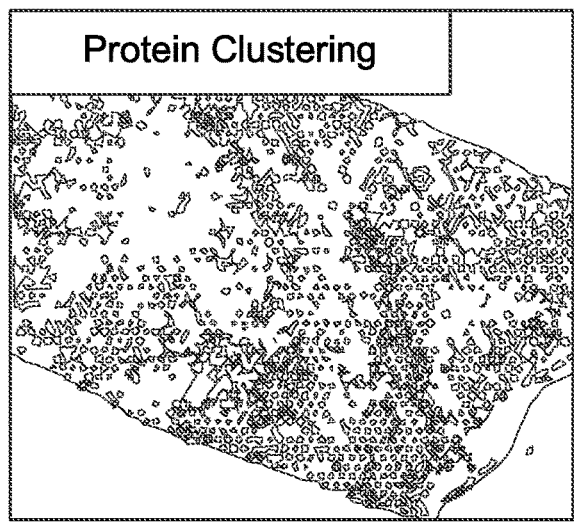
Figure 28D:
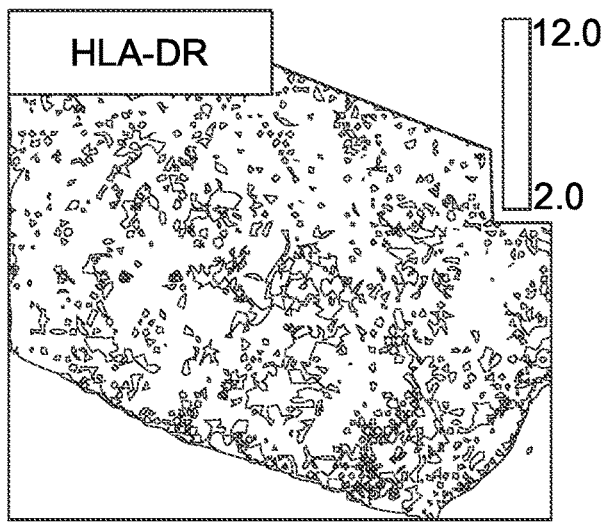

As shown in FIGS. 28A-D spatial gene and spatial protein expression analysis in a FFPE melanoma tissue section. FIG. 28A shows an H&E stained lung cancer FFPE tissue section and FIGS. 28B and 28C, show spatial gene expression clustering (FIG. 28B) and spatial protein expression clustering (FIG. 28C), respectively. FIG. 28D shows HLA-DR protein spatial UMI plot. As described herein, HLA-DR is a marker of T cell activation and FIG. 28D The data demonstrate that spatial gene and spatial protein expression correlate with each other which demonstrates the utility of the methods described herein in identifying spatial gene and protein expression in melanoma FFPE tissue sections which can be used as a diagnostic tool.

Other Tissues Assayed

In addition to the various FFPE tissue sections assayed as described herein, other tissue types were assayed including: healthy brain tissue, breast cancer invasive lobular carcinoma tissue, healthy breast tissue, colon cancer tissue, healthy colon tissue, glioblastoma tissue, heart tissue, healthy lung tissue, prostate cancer tissue, healthy spleen tissue, testes tissue, inflamed tonsil tissue, cervix tissue, and lymph node tissue (data not shown).

Figure 29A:
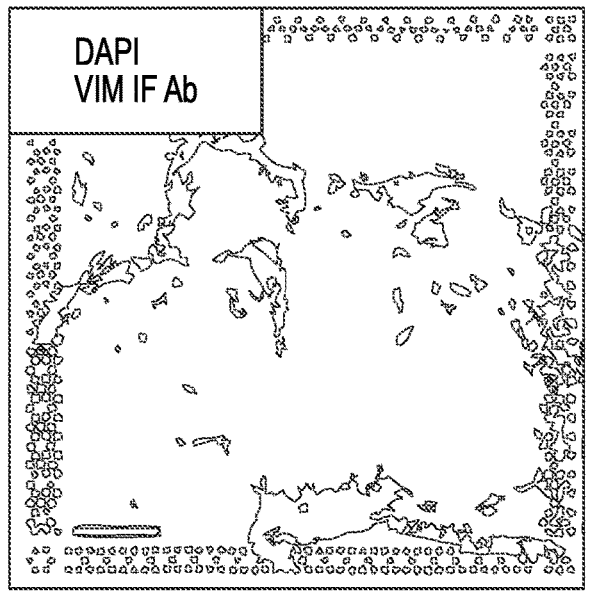
FIGS. 29A-C show exemplary Vimentin antibody immunofluorescence staining and DAPI staining (FIG. 29A), exemplary spatial protein expression (FIG. 29B), and exemplary Vimentin spatial protein expression (FIG. 29C) in a grade II invasive ductal carcinoma FFPE breast cancer tissue section.
Figure 29B:
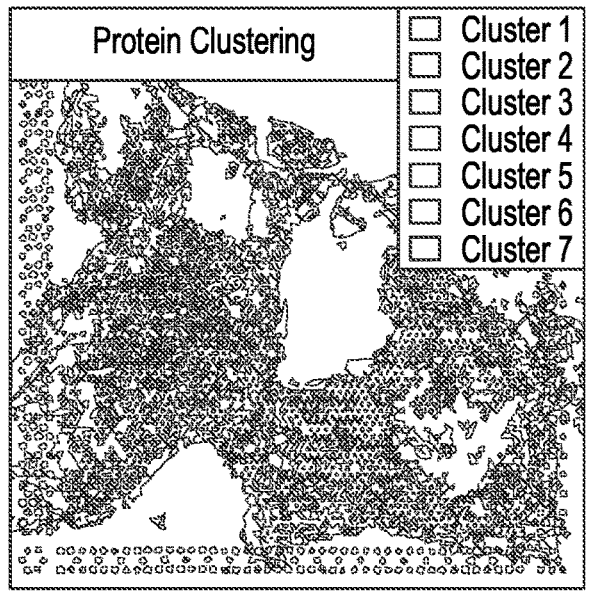
Figure 29C:
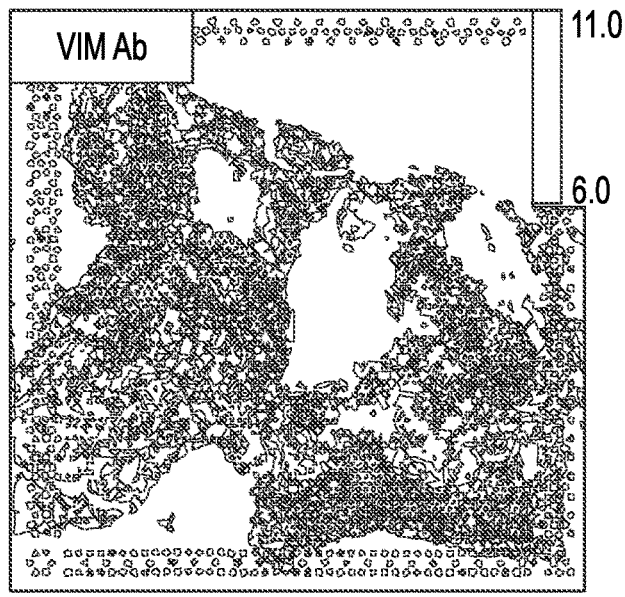

Example 7. Spatial Protein Expression Correlates with Immunofluorescence Staining FIGS. 29A-C show Vimentin (VIM) antibody immunofluorescence staining (FIG. 29A) and DAPI staining in a grade II invasive ductal carcinoma FFPE breast cancer tissue section. FIG. 29B shows spatial protein expression superimposed on the fluorescent image in FIG. 29A. FIG. 29C shows spatial protein expression with a VIM specific analyte capture agent in the same tissue section. The data demonstrate a similar spatial distribution between Vimentin antibody immunofluorescent staining (FIG. 29A) and spatial protein expression with a VIM specific analyte capture agent (FIG. 29C) and demonstrates the utility of the methods described herein to recapitulate spatial protein expression with analyte capture agents relative to immunofluorescent antibody staining.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the spatial location of a nucleic acid and a protein from a biological sample comprising:
    a) providing a spatial array comprising a first and second plurality of capture probes wherein each of the first and second plurality of capture probes comprises a spatial barcode and a capture domain,
    b) contacting the biological sample with
        (i) a plurality of analyte capture agents, wherein an analyte capture agent comprises an analyte binding moiety and an oligonucleotide comprising an analyte binding moiety barcode and an analyte capture sequence, wherein the analyte capture sequence comprises a sequence complementary to a second plurality of capture domains, and
        (ii) a plurality of templated ligation probe pairs, wherein one of the templated ligation probes in the probe pair comprises a sequence complementary to a first plurality of capture domains,
    c) binding the analyte binding moiety of the analyte capture agent to a target protein,
    d) hybridizing the templated ligation probe pairs to a target nucleic acid and ligating the probe pairs to produce ligation products,
    e) hybridizing the ligation products to the first plurality of capture domains and the analyte capture sequences of the bound analyte capture agents to the second plurality of capture domains on the spatial array, and
    f) determining the sequence or a portion thereof of (i) the ligation product, or a complement thereof, (ii) the spatial barcode of the capture probe hybridized to the ligation product, or a complement thereof, (iii) the analyte binding moiety barcode of the analyte capture agent bound to the target protein, or a complement thereof, and (iv) the spatial barcode of the capture probe hybridized to the oligonucleotide comprising the analyte binding moiety barcode the analyte capture sequence, thereby determining the spatial location of the nucleic acid and the protein from the biological sample.

2. The method of claim 1, wherein the biological sample is placed on the spatial array prior to step b).

3. The method of claim 1, wherein the biological sample is on a substrate without a spatial array, and wherein prior to step e) the ligation products and the analyte capture sequences of the bound analyte capture agents are migrated to the spatial array.

4. The method of claim 1, wherein the capture domains of the first plurality of capture probes are non-homopolymeric capture sequences or homopolymeric sequences, and the capture domains of the second plurality of capture probes are non-homopolymeric sequences or homopolymeric capture sequences.

5. The method of claim 4, wherein the capture domains of the first plurality of capture probes are different from the capture domains of the second plurality of capture probes.

6. The method of claim 4, wherein the homopolymeric sequences comprise a polyT sequence and the non-homopolymeric sequences comprise a fixed sequence.

7. The method of claim 6, wherein the fixed sequence comprises at least one sequence selected from SEQ ID NO: 1 through SEQ ID NO: 11.

8. The method of claim 1, wherein the biological sample is a tissue sample, and wherein the tissue sample is a fresh-frozen tissue sample or a fixed tissue sample, wherein the fixed tissue sample is a formalin-fixed tissue sample, an acetone fixed tissue sample, a paraformaldehyde tissue sample, or a methanol fixed tissue sample.

9. The method of claim 8, wherein the tissue sample is obtained from a normal tissue sample, a tissue biopsy sample, a diseased tissue sample, or a rodent tissue.

10. The method of claim 1, wherein before step (b) the biological sample is deparaffinized and decrosslinked, and wherein the decrosslinking comprises the use of a buffer.

11. The method of claim 10, wherein the buffer comprises Tris-EDTA buffer at a pH from about 8 to about 10 and a temperature from about 60° C. to about 90° C.

12. The method of claim 10, wherein the buffer comprises citrate buffer at a pH from about 5 to about 7 and a temperature from about 70° C. to about 100° C.

13. The method of claim 1, wherein hybridizing the ligation products to the first plurality of capture domains and hybridizing the analyte capture sequences of the bound analyte capture agents to the second plurality of capture domains comprises permeabilizing the biological sample.

14. The method of claim 1, wherein the analyte capture sequence of the analyte capture agent is blocked prior to binding the analyte capture agent to the target protein.

15. The method of claim 14, wherein the analyte capture sequence of the analyte capture agent is blocked by a blocking probe, and wherein the blocking probe is removed prior to hybridizing the analyte capture sequence of the analyte capture agent to the capture domain of the capture probe.

16. The method of claim 1, wherein the determining in step (f) further comprises:
  g) extending the ligation products and the oligonucleotides of the analyte capture agents, wherein the extension products comprise the spatial barcode or a complement thereof,
  h) releasing the extension products, or complements thereof, from the spatial array,
  i) producing a nucleic acid library from the released extension products or complements thereof; and
  j) sequencing the library.

17. The method of claim 16, wherein prior to step (i) the method further comprises pre-amplifying the extension products, or complements thereof.

18. The method of claim 16, wherein the complement of the oligonucleotide of the analyte capture agent comprises an analyte binding moiety barcode specific to the analyte binding moiety of the analyte capture agent.

19. The method of claim 1, wherein the first and second plurality of capture probes further comprise a cleavage domain, one or more functional domains, a unique molecular identifier, and combinations thereof.

20. The method of claim 1, wherein the method further comprises imaging the biological sample.

21. The method of claim 20, wherein the imaging comprises one or more of expansion microscopy, bright field microscopy, dark field microscopy, phase contrast microscopy, electron microscopy, fluorescence microscopy, reflection microscopy, interference microscopy and confocal microscopy.

22. The method of claim 1, wherein the method further comprises staining the biological sample, wherein the staining comprises hematoxylin and eosin, or the use of a detectable label selected from the group consisting of a radioisotope, a fluorophore, a chemiluminescent compound, a bioluminescent compound, or a combination thereof.

23. The method of claim 1, wherein the spatial array further comprises one or more protein dilution series.

* * * * *

UNITED STATES PATENT AND TRADEMARK OFFICE
CERTIFICATE OF CORRECTION

PATENT NO. : 11,739,381 B2
APPLICATION NO. : 17/867223
DATED : August 29, 2023
INVENTOR(S) : Jennifer Chew et al.

Page 1 of 1

It is certified that error appears in the above-identified patent and that said Letters Patent is hereby corrected as shown below:

In the Claims

Column 47, Line 62, in Claim 1, before "the" insert -- of --.

Signed and Sealed this
Thirty-first Day of October, 2023

Katherine Kelly Vidal
*Director of the United States Patent and Trademark Office*

SEQUENCE LISTING

```
Sequence total quantity: 11
SEQ ID NO: 1            moltype = DNA   length = 22
FEATURE                 Location/Qualifiers
misc_feature            1..22
                        note = Capture Domain 22mer
source                  1..22
                        mol_type = other DNA
                        organism = synthetic construct
```

```
SEQUENCE: 1
ttgctaggac cggccttaaa gc                                              22

SEQ ID NO: 2           moltype = DNA  length = 21
FEATURE                Location/Qualifiers
misc_feature           1..21
                       note = Capture Domain 21mer
source                 1..21
                       mol_type = other DNA
                       organism = synthetic construct
SEQUENCE: 2
ttgctaggac cggccttaaa g                                               21

SEQ ID NO: 3           moltype = DNA  length = 20
FEATURE                Location/Qualifiers
misc_feature           1..20
                       note = Capture Domain 20mer
source                 1..20
                       mol_type = other DNA
                       organism = synthetic construct
SEQUENCE: 3
ttgctaggac cggccttaaa                                                 20

SEQ ID NO: 4           moltype = DNA  length = 19
FEATURE                Location/Qualifiers
misc_feature           1..19
                       note = Capture Domain 19mer
source                 1..19
                       mol_type = other DNA
                       organism = synthetic construct
SEQUENCE: 4
ttgctaggac cggccttaa                                                  19

SEQ ID NO: 5           moltype = DNA  length = 18
FEATURE                Location/Qualifiers
misc_feature           1..18
                       note = Capture Domain 18mer
source                 1..18
                       mol_type = other DNA
                       organism = synthetic construct
SEQUENCE: 5
ttgctaggac cggcctta                                                   18

SEQ ID NO: 6           moltype = DNA  length = 17
FEATURE                Location/Qualifiers
misc_feature           1..17
                       note = Capture Domain 17mer
source                 1..17
                       mol_type = other DNA
                       organism = synthetic construct
SEQUENCE: 6
ttgctaggac cggcctt                                                    17

SEQ ID NO: 7           moltype = DNA  length = 16
FEATURE                Location/Qualifiers
misc_feature           1..16
                       note = Capture Domain 16mer
source                 1..16
                       mol_type = other DNA
                       organism = synthetic construct
SEQUENCE: 7
ttgctaggac cggcct                                                     16

SEQ ID NO: 8           moltype = DNA  length = 15
FEATURE                Location/Qualifiers
misc_feature           1..15
                       note = Capture Domain 15mer
source                 1..15
                       mol_type = other DNA
                       organism = synthetic construct
SEQUENCE: 8
ttgctaggac cggcc                                                      15

SEQ ID NO: 9           moltype = DNA  length = 14
FEATURE                Location/Qualifiers
misc_feature           1..14
                       note = Capture Domain 14mer
source                 1..14
                       mol_type = other DNA
```

-continued

```
                        organism = synthetic construct
SEQUENCE: 9
ttgctaggac cggc                                                         14

SEQ ID NO: 10           moltype = DNA  length = 13
FEATURE                 Location/Qualifiers
misc_feature            1..13
                        note = Capture Domain 13mer
source                  1..13
                        mol_type = other DNA
                        organism = synthetic construct
SEQUENCE: 10
ttgctaggac cgg                                                          13

SEQ ID NO: 11           moltype = DNA  length = 12
FEATURE                 Location/Qualifiers
misc_feature            1..12
                        note = Capture Domain 12mer
source                  1..12
                        mol_type = other DNA
                        organism = synthetic construct
SEQUENCE: 11
ttgctaggac cg                                                           12
```